US008552255B2

(12) United States Patent
Chardonnens et al.

(10) Patent No.: US 8,552,255 B2
(45) Date of Patent: Oct. 8, 2013

(54) NUCLEIC ACID SEQUENCES ENCODING PROTEINS ASSOCIATED WITH ABIOTIC STRESS RESPONSE

(75) Inventors: Agnes Chardonnens, Berlin (DE); Piotr Puzio, Berlin (DE)

(73) Assignee: BASF Plant Science GmbH, Ludwigshafen (DE)

( * ) Notice: Subject to any disclaimer, the term of this patent is extended or adjusted under 35 U.S.C. 154(b) by 0 days.

(21) Appl. No.: 13/097,265

(22) Filed: Apr. 29, 2011

(65) Prior Publication Data

US 2011/0321196 A1    Dec. 29, 2011

Related U.S. Application Data

(63) Continuation of application No. 10/523,362, filed as application No. PCT/EP03/06994 on Jul. 1, 2003, now abandoned.

(30) Foreign Application Priority Data

Aug. 7, 2002    (EP) .................................... 02017671

(51) Int. Cl.
*C12N 15/82*    (2006.01)
*C12N 15/63*    (2006.01)

(52) U.S. Cl.
USPC ........................................ 800/278; 435/468

(58) Field of Classification Search
None
See application file for complete search history.

(56) References Cited

U.S. PATENT DOCUMENTS 7,847,159 B2    12/2010 Puzio et al.

FOREIGN PATENT DOCUMENTS

| WO | WO-99/04013 A2 | | 1/1999 |
|---|---|---|---|
| WO | WO-00/14239 A2 | | 3/2000 |
| WO | WO 00/36126 | * | 6/2000 |
| WO | WO-00/36126 A1 | | 6/2000 |
| WO | WO-00/49165 A1 | | 8/2000 |
| WO | WO-00/58453 A2 | | 10/2000 |
| WO | WO-00/63417 A2 | | 10/2000 |
| WO | WO-02/053589 A2 | | 7/2002 |
| WO | WO-02/064766 | | 8/2002 |
| WO | WO-2004/092398 A2 | | 10/2004 |

OTHER PUBLICATIONS

Wells, Biochemistry 29:8509-8517, 1990.*
Ngo et al., (The Protein Folding Problem and Tertiary Structure Prediction, K. Merz., and S. Le Grand (eds.) pp. 492-495,1994).*
Guo et al. (PNAS, 101: 9205-9210, 2004).*
Keskin et al. (Protein Science, 13:1043-1055, 2004).*
Thornton et al. (Nature structural Biology, structural genomics supplement, Nov. 2000).*
Doerks et al., (TIG, 14:248-250, 1998).*
Smith et al. (Nature Biotechnology, 15:1222-1223, 1997).*
Bork et al. (TIG, 12:425-427, 1996).*
Dietrich et al. (GenBank Sequence Accession No. U18922.1; Published Oct. 10, 2000).*
Grant et al. (Biochimica et Biophysica Acta, 1490:33-42, 2000).*
Samuelsen et al. (Plant Physiol., 118:51-58, 1998).*
Stomp et al. (Plant Physiol., 92:1226-1232, 1990).*
McKersie, B.D., et al., "Water-Deficit Tolerance and Field Performance of Transgenic Alfalfa Overexpressing Superoxide Dismutase", Plant Physiol. (1996), vol. 111, pp. 1177-1181.
Broin, M., et al., "The Plastidic 2-Cysteine Peroxiredoxin Is a Target for a Thioredoxin Involved in the Protection of the Photosynthetic Apparatus against Oxidative Damage", The Plant Cell (2002), vol. 14, pp. 1417-1432.
Lee, K.O., et al., "Rice 1Cys-Peroxiredoxin Over-Expressed in Transgenic Tobacco Does not Maintain Dormancy but Enhances Antioxidant Activity", FEBS Letters (2000), vol. 486, pp. 103-106.
Bick, J.-A., et al., "Glutaredoxin Function for the Carboxyl-Terminal Domain of the Plant-Type 5'-Adenylylsulfate Reductase", Proc. Natl. Acad. Sci. USA (1998), vol. 95, pp. 8404-8409.
Minakuchi, K., et al., "Cloning and Sequence Analysis of a cDNA Encoding Rice Glutaredoxin", FEBS Letters (1994), vol. 337, pp. 157-160.
Roxas, V.P., et al., "Stress Tolerance in Transgenic Tobacco Seedlings that Overexpress Glutathione S-Transferase/Glutathione Peroxidase", Plant Cell Physiol. (2000), vol. 4, No. 11, pp. 1229-1234.
Collinson, E.J., et al., "The Yeast Glutaredoxins Are Active as Glutathione Peroxidases", The Journal of Biological Chemistry (2002), vol. 277, No. 19, pp. 16712-16717.
Luikenhuis, S., et al., "The Yeast *Saccharomyces cerevisiae* Contains Two Glutaredoxin Genes That Are Required for Protection Against Reactive Oxygen Species", Molecular Biology of the Cell, 1998, vol. 9, pp. 1081-1091.
"TTR=thioltransferase [*Saccharomyces cerevisiae*, DMY6(Leu), Genomic, 718 nt]", EMBL-EBI Database Accession No. S45268, Feb. 16, 1993.
"*Saccharomyces cerevisiae* Chromosome IV Cosmids 8166, 9787, 9717, and Lambda 3073", EMBL-EBI Database Accession No. U33057, Aug. 6, 1995.
Romero, C., et al., "Expression of the Yeast Trehalose-6-Phosphate Synthase Gene in Transgenic Tobacco Plants: Pleiotropic Phenotypes Include Drought Tolerance", Planta (1997), vol. 201, No. 3, pp. 293-297.
Samuelsen, A.I., et al., "Expression of the Yeast FRE Genes in Transgenic Tobacco", Plant Physiol. (1998), vol. 118, No. 1, pp. 51-58.
Stomp, A.M., et al., "Extended Host Range of *Agrobacterium tumefaciens* in the Genus Pinus", Plant Physiol. (1990), vol. 92, No. 4, pp. 1226-1232.

(Continued)

*Primary Examiner* — Vinod Kumar
(74) *Attorney, Agent, or Firm* — Novak Druce Connolly Bove + Quigg LLP

(57) ABSTRACT

The present invention pertains transgenic plant cells and mature plants comprising Oxidoreductase Stress Related Proteins (ORSRP) resulting in increased tolerance and/or resistance to environmental stress as compared to non-transformed wild type cells and methods of producing such plant cells or plants. Further object of the present invention are isolated ORSRPs or ORSRP encoding nucleic acids from plants.

8 Claims, 7 Drawing Sheets

(56) References Cited

OTHER PUBLICATIONS

Keskin, O., et al., "A New, Structurally Nonredundant, Diverse Data Set of Protein-Protein Interfaces and its Implications", Protein Sci. (2004), vol. 13, No. 4, pp. 1043-1055.

Thornton, J.M., et al., "From Structure to Function: Approaches and Limitations", Nat. Struct. Biol. (2000), vol. 7 Suppl., pp. 991-994.

Guo, H.H., et al., "Protein Tolerance to Random Amino Acid Change", Proc. Natl. Acad. Sci. U S A. (2004), vol. 101, No. 25, pp. 9205-9210.

Gan, Z.R., "Cloning and Sequencing of a Gene Encoding Yeast Thioltransferase", Biochem. Biophys. Res. Commun. (1992), vol. 187, No. 2, pp. 949-955.

Valvekens, D., et al., "*Agrobacterium tumefaciens*-Mediated Transformation of *Arabidopsis thaliana* Root Explants by Using Kanamycin Selection", Proc. Natl. Acad. Sci. U S A. (1988), vol. 85, No. 15, pp. 5536-5540.

Grant, C.M., et al., "Differential Regulation of Glutaredoxin Gene Expression in Response to Stress Conditions in the Yeast *Saccharomyces cerevisiae*", Biochim. Biophys. Acta. (2000), vol. 1490, No. 1-2, pp. 33-42.

Gupta, A.S., et al., "Increased Resistance to Oxidative Stress in Transgenic Plants that Overexpress Chloroplastic Cu/Zn Superoxide Dismutase", Proc. Natl. Acad. Sci. U S A. (1993), vol. 90, No. 4, pp. 1629-1633.

Foyer, C.H., et al., "Overexpression of Glutathione Reductase but not Glutathione Synthetase Leads to Increases in Antioxidant Capacity and Resistance to Photoinhibition in Poplar Trees", Plant Physiol. (1995), vol. 109, No. 3, pp. 1047-1057.

\* cited by examiner

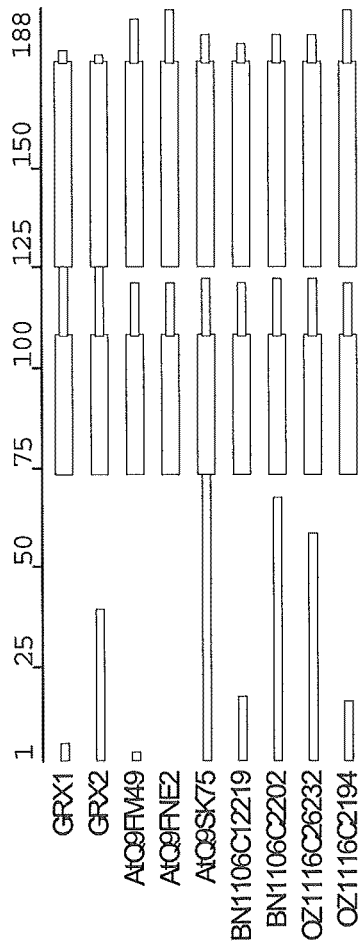

Fig. 4

```
                      125       130       140       150       160       175
GRX1         ( 57) KEGADIQAALYEINGQRTVPNIYINGKHIGGNDDLQELRETGELEELLEPI
GRX2         ( 91) SNGSEIQDALEEISGQKTVPNVYINGKHIGGNSDLETLKKNGKLAEILKPV
AtQ9FM49     ( 51) SDGGEIQSALSEWTGQTTVPNVFIKGNHIGGCDRVMETNKQGKLVPLLTEA
AtQ9FNE2     ( 49) SDGSQIQSGLAEWTGQRTVPNVFIGGNHIGGCDATSNLHKDGKLVPLLTEA
AtQ9SK75     (122) SEGSQLQNVLEKITGQYTVPNVFIGGKHIGGCSDTLQLHNKGELEAILAEA
BN1106C12219 ( 65) SDGGEIQSALSEWTGQSTVPNVFIKGKHIGGCDRVMESNKQGKLVPLLTEA
BN1106C2202  (116) PQGTQLQKVLETLTGQRTVPNVFVGGKHIGGCTDTVNLNRKGELELMLAEA
OZ1116C26232 (107) AQGPQLQKVLERLTGQSTVPNVFIGGKHIGGCTDTVKLHRKGELATMLSEL
OZ1116C2194  ( 64) SDGSELQSALAEWTGQRTVPNVFINGKHIGGCDDTLALNNEGKLVPLLTEA
```

Fig. 7

```
                  87                          100               110               120                139
       THX1 (47)  QYSDAAFYKLDVDEVSDVAQKAEVSSMPTLIFYKGGKEVTRVVGANPAAIKQA
       THX2 (46)  QYPQADFYKLDVDELGDVAQKNEVSAMPTLLLFKNGKEVAKVVGANPAAIKQA
       GRX3 (87)  SNSNVSFLSIDADENSEISELFEISAVPYFIIHKGTILKELSGADPKEYVSL
       GRX4 (52)  RQEDVRFLSIDADEHPEISDLFEIAAVPYFVFIQNGTIVKEISAADPKEFVKS
 BN1106C23043 (49) DFPRAHFFRVEAEEHPEISEAYSVSAVPYFVFFKDGKAVDTLEGADPSSLANK
      AtO65541 (49) DFPRAHFFRVEAEEHPEISEAYSVALVPYFVFFKDGKTVDTLEGADPSSLANK
      AtQ9ZPH2 (49) DFPRAHFFRVEAEEHPEISEAYSVAAVPYFVFFKDGKTVDTLEGADPSSLANK
```

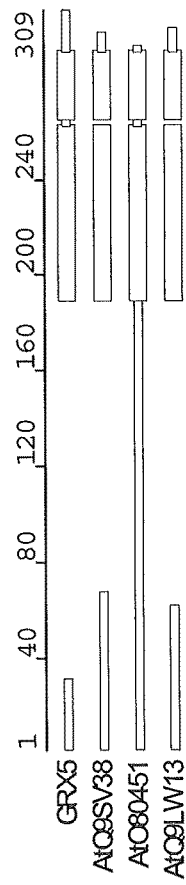

| | | |
|---|---|---|
| GRX5 (30) | 189 | LSTEIRKAIEDAIESAPVVLFMKGTPEFPKCGFSRATIGLIGNQGVDPAKFAAYNVLEDPELREGIKEFSEWP |
| AtQ9SV38 (67) | | LITPQLKDITLEKLVNSEKVVLFMKGIRDFPMCGFSNIVQILKNLNVPFEDVNILENEMLRQGLKEYSNWPTFP |
| AtO80451 (189) | | LTVPLEELIDRLVKESKVVAFIKGSRSAPQQGFSQRVVGILESQGVDYETVDVLDEYNHGIRETLKNYSNWP |
| AtQ9LW13 (61) | | SIDSLKDIVENDVKDNPVMIYMKGVPESPQCGFSSLAVRVLQQYNVPISSRNILEDQELKNAVKSFSHWPIFP |

Fig. 10

| | 265 270 280 291 |
|---|---|
| GRX5 (106) | QLYVNKEFIGGCDVITSMARSGELADL |
| AtQ9SV38 (140) | QLYIGGEFFGGCDITLEAFKTGELQEE |
| AtO80451 (265) | QIFVKGELVGGCDILTSMYENGELANI |
| AtQ9LW13 (134) | QIFIKGEFIGGSDIILNMHKEGELEQK |

Fig. 11

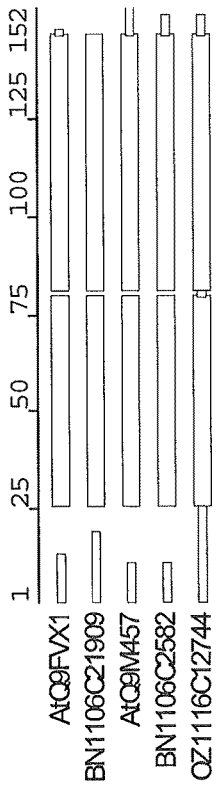

Fig. 12

```
                  26                                                        78
AtQ9FVX1     (13) ALLLFVVLCDLSNSAGAANSVSAFVQNAILSNKIVIFSKSYCPYCLRSKRIFS
BN1106C21909 (19) LLILAVVPSDLSISAGAEKSVAAFVQNAILSNKIVIFSKSYCPYCLRSKRIFR
AtQ9M457     (11) MLLVALVTFISMVSSAASSPEADFVKKTISSHKIVIFSKSYCPYCKKAKSVFR
BN1106C2582  (11) MLIVALVSSISIVSSASSSPEAEFVKKTISSHKIVIFSKSYCPYCRRAKSVFS
OZ1116C12744 (26) AAAALIALAALGSAASGTASKSSFVKSTVKAHDVVIFSKSYCPYCRRAKAVFK
```

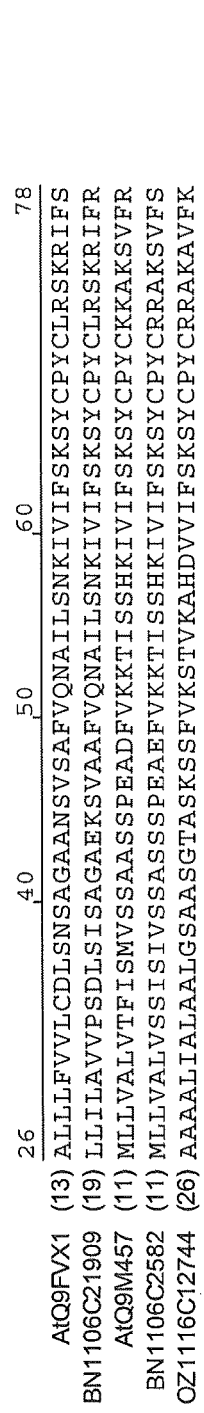

Fig. 13

```
                  81                                                                                145
AtQ9FVX1     (66) QLKEEPFVVELDQREDGDQIQYELLEFVGRRTVPQVFVNGKHIGGSDDLGAALESGQLQKLLAAS
EN1106C21909 (72) ELKEQPFVVELDLREDGDKIQYELLEFVGRRTVPQVFVNGKHIGGSDDLADSVENGQLQKLLAAS
AtQ9M457     (64) ELDQVPYVVELDEREDGWSIQTALGEIVGRRTVPQVFINGKHLGGSDDTVDAYESGELAKLLGVS
EN1106C2582  (64) ELDQVPHVVELDEREDGWNVQSALGEIVGRRTVPQVFINGKHIGGSDDTVEAHESGELAKLLGLS
OZ1116C12744 (81) ELKKEPYVVELDQREDGWEIQDALSDMVGRRTVPQVFVHGKHLGGSDDTVEAYESGKLAKLLNID
```

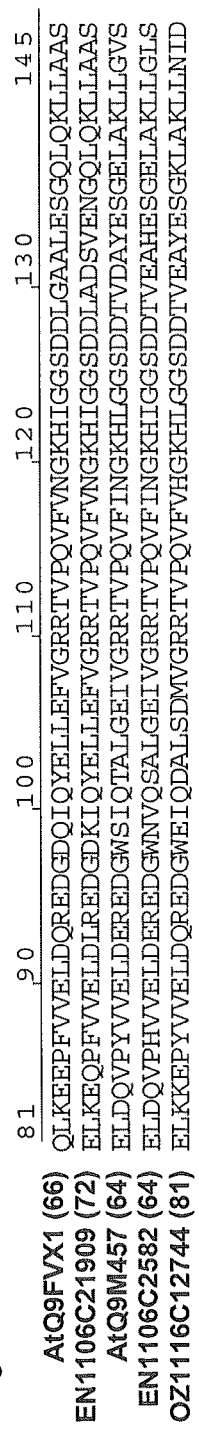

SEQUENCE LISTING

```
<160> NUMBER OF SEQ ID NOS: 67

<210> SEQ ID NO 1
<211> LENGTH: 333
<212> TYPE: DNA
<213> ORGANISM: Saccharomyces cerevisiae
<220> FEATURE:
<221> NAME/KEY: CDS
<222> LOCATION: (1)..(330)
<223> OTHER INFORMATION: GRX1

<400> SEQUENCE: 1 atg gta tct caa gaa act atc aag cac gtc aag gac ctt att gca gaa      48
Met Val Ser Gln Glu Thr Ile Lys His Val Lys Asp Leu Ile Ala Glu
1               5                   10                  15 aac gag atc ttc gtc gca tcc aaa acg tac tgt cca tac tgc cat gca      96
Asn Glu Ile Phe Val Ala Ser Lys Thr Tyr Cys Pro Tyr Cys His Ala
            20                  25                  30 gcc cta aac acg ctt ttt gaa aag tta aag gtt ccc agg tcc aaa gtt     144
Ala Leu Asn Thr Leu Phe Glu Lys Leu Lys Val Pro Arg Ser Lys Val
        35                  40                  45 ctg gtt ttg caa ttg aat gac atg aag gaa ggc gca gac att cag gct     192
Leu Val Leu Gln Leu Asn Asp Met Lys Glu Gly Ala Asp Ile Gln Ala
    50                  55                  60
```

```
gcg tta tat gag att aat ggc caa aga acc gtg cca aac atc tat att      240
Ala Leu Tyr Glu Ile Asn Gly Gln Arg Thr Val Pro Asn Ile Tyr Ile
 65                  70                  75                  80 aat ggt aaa cat att gga ggc aac gac gac ttg cag gaa ttg agg gag      288
Asn Gly Lys His Ile Gly Gly Asn Asp Asp Leu Gln Glu Leu Arg Glu
                 85                  90                  95 act ggt gaa ttg gag gaa ttg tta gaa cct att ctt gca aat taa          333
Thr Gly Glu Leu Glu Glu Leu Leu Glu Pro Ile Leu Ala Asn
            100                 105                 110

<210> SEQ ID NO 2
<211> LENGTH: 110
<212> TYPE: PRT
<213> ORGANISM: Saccharomyces cerevisiae

<400> SEQUENCE: 2

Met Val Ser Gln Glu Thr Ile Lys His Val Lys Asp Leu Ile Ala Glu
 1               5                  10                  15

Asn Glu Ile Phe Val Ala Ser Lys Thr Tyr Cys Pro Tyr Cys His Ala
                20                  25                  30

Ala Leu Asn Thr Leu Phe Glu Lys Leu Lys Val Pro Arg Ser Lys Val
            35                  40                  45

Leu Val Leu Gln Leu Asn Asp Met Lys Glu Gly Ala Asp Ile Gln Ala
 50                  55                  60

Ala Leu Tyr Glu Ile Asn Gly Gln Arg Thr Val Pro Asn Ile Tyr Ile
 65                  70                  75                  80

Asn Gly Lys His Ile Gly Gly Asn Asp Asp Leu Gln Glu Leu Arg Glu
                 85                  90                  95

Thr Gly Glu Leu Glu Glu Leu Leu Glu Pro Ile Leu Ala Asn
            100                 105                 110

<210> SEQ ID NO 3
<211> LENGTH: 432
<212> TYPE: DNA
<213> ORGANISM: Saccharomyces cerevisiae
<220> FEATURE:
<221> NAME/KEY: CDS
<222> LOCATION: (1)..(432)

<400> SEQUENCE: 3 atg gag acc aat ttt tcc ttc gac tcg aat tta att gtt att atc att      48
Met Glu Thr Asn Phe Ser Phe Asp Ser Asn Leu Ile Val Ile Ile Ile
 1               5                  10                  15 atc acg ttg ttt gcc aca aga att att gct aaa aga ttt tta tct act      96
Ile Thr Leu Phe Ala Thr Arg Ile Ile Ala Lys Arg Phe Leu Ser Thr
                20                  25                  30 cca aaa atg gta tcc cag gaa aca gtt gct cac gta aag gat ctg att     144
Pro Lys Met Val Ser Gln Glu Thr Val Ala His Val Lys Asp Leu Ile
            35                  40                  45 ggc caa aag gaa gtg ttt gtt gca gca aag aca tac tgc cct tac tgt     192
Gly Gln Lys Glu Val Phe Val Ala Ala Lys Thr Tyr Cys Pro Tyr Cys
 50                  55                  60 aaa gct act ttg tct acc ctc ttc caa gaa ttg aac gtt ccc aaa tcc     240
Lys Ala Thr Leu Ser Thr Leu Phe Gln Glu Leu Asn Val Pro Lys Ser
 65                  70                  75                  80 aag gcc ctt gtg ttg gaa tta gat gaa atg agc aat ggc tca gag att     288
Lys Ala Leu Val Leu Glu Leu Asp Glu Met Ser Asn Gly Ser Glu Ile
                85                  90                  95 caa gac gct tta gaa gaa atc tcg ggc caa aaa act gta cct aac gta     336
Gln Asp Ala Leu Glu Glu Ile Ser Gly Gln Lys Thr Val Pro Asn Val
            100                 105                 110
```

```
tac atc aat ggc aag cac att ggt ggt aac agc gat ttg gaa act ttg    384
Tyr Ile Asn Gly Lys His Ile Gly Gly Asn Ser Asp Leu Glu Thr Leu
            115                 120                 125 aag aaa aat ggc aag tta gct gaa ata ttg aag ccg gta ttt caa tag    432
Lys Lys Asn Gly Lys Leu Ala Glu Ile Leu Lys Pro Val Phe Gln
    130                 135                 140

<210> SEQ ID NO 4
<211> LENGTH: 143
<212> TYPE: PRT
<213> ORGANISM: Saccharomyces cerevisiae

<400> SEQUENCE: 4

Met Glu Thr Asn Phe Ser Phe Asp Ser Asn Leu Ile Val Ile Ile
1               5                   10                  15

Ile Thr Leu Phe Ala Thr Arg Ile Ile Ala Lys Arg Phe Leu Ser Thr
            20                  25                  30

Pro Lys Met Val Ser Gln Glu Thr Val Ala His Val Lys Asp Leu Ile
        35                  40                  45

Gly Gln Lys Glu Val Phe Val Ala Ala Lys Thr Tyr Cys Pro Tyr Cys
    50                  55                  60

Lys Ala Thr Leu Ser Thr Leu Phe Gln Glu Leu Asn Val Pro Lys Ser
65                  70                  75                  80

Lys Ala Leu Val Leu Glu Leu Asp Glu Met Ser Asn Gly Ser Glu Ile
                85                  90                  95

Gln Asp Ala Leu Glu Glu Ile Ser Gly Gln Lys Thr Val Pro Asn Val
            100                 105                 110

Tyr Ile Asn Gly Lys His Ile Gly Gly Asn Ser Asp Leu Glu Thr Leu
        115                 120                 125

Lys Lys Asn Gly Lys Leu Ala Glu Ile Leu Lys Pro Val Phe Gln
    130                 135                 140

<210> SEQ ID NO 5
<211> LENGTH: 858
<212> TYPE: DNA
<213> ORGANISM: Saccharomyces cerevisiae
<220> FEATURE:
<221> NAME/KEY: CDS
<222> LOCATION: (1)..(855)
<223> OTHER INFORMATION: GRX3

<400> SEQUENCE: 5 atg tgt tct ttt cag gtt cca tct gca ttt tct ttt aac tac acc tcg    48
Met Cys Ser Phe Gln Val Pro Ser Ala Phe Ser Phe Asn Tyr Thr Ser
1               5                   10                  15 tac tgt tat aaa cgc cac caa gca aga tat tac aca gca gca aaa ctt    96
Tyr Cys Tyr Lys Arg His Gln Ala Arg Tyr Tyr Thr Ala Ala Lys Leu
            20                  25                  30 ttt cag gaa atg cct gtt att gaa att aac gat caa gag caa ttt act   144
Phe Gln Glu Met Pro Val Ile Glu Ile Asn Asp Gln Glu Gln Phe Thr
        35                  40                  45 tac cta act acc act gcg gcc ggc gac aag tta atc gtg ctt tat ttc   192
Tyr Leu Thr Thr Thr Ala Ala Gly Asp Lys Leu Ile Val Leu Tyr Phe
    50                  55                  60 cat acc agt tgg gca gaa cca tgc aaa gca tta aag cag gtt ttt gag   240
His Thr Ser Trp Ala Glu Pro Cys Lys Ala Leu Lys Gln Val Phe Glu
65                  70                  75                  80 gcc att agt aat gag cct tcc aat tcc aac gtc tct ttc tta tcc att   288
Ala Ile Ser Asn Glu Pro Ser Asn Ser Asn Val Ser Phe Leu Ser Ile
                85                  90                  95 gat gcg gac gaa aac tcg gaa att tca gaa ctt ttt gaa atc tca gct   336
Asp Ala Asp Glu Asn Ser Glu Ile Ser Glu Leu Phe Glu Ile Ser Ala
```

```
Asp Ala Asp Glu Asn Ser Glu Ile Ser Glu Leu Phe Glu Ile Ser Ala
                100                 105                 110 gtt cca tat ttt atc ata att cac aaa ggg aca atc tta aaa gaa tta      384
Val Pro Tyr Phe Ile Ile Ile His Lys Gly Thr Ile Leu Lys Glu Leu
            115                 120                 125 tcc ggc gcg gat cca aag gag tat gtg tct tta tta gaa gac tgc aag      432
Ser Gly Ala Asp Pro Lys Glu Tyr Val Ser Leu Leu Glu Asp Cys Lys
        130                 135                 140 aac tca gtc aat tcc gga tca tca caa act cat act atg gaa aat gca      480
Asn Ser Val Asn Ser Gly Ser Ser Gln Thr His Thr Met Glu Asn Ala
145                 150                 155                 160 aac gta aat gag ggg agt cat aat gat gaa gac gat gac gac gaa gaa      528
Asn Val Asn Glu Gly Ser His Asn Asp Glu Asp Asp Asp Asp Glu Glu
                165                 170                 175 gag gaa gaa gaa act gag gag caa ata aac gct aga ttg act aaa ttg      576
Glu Glu Glu Glu Thr Glu Glu Gln Ile Asn Ala Arg Leu Thr Lys Leu
            180                 185                 190 gtc aat gcc gcg ccg gta atg tta ttt atg aag ggg agc ccc tct gaa      624
Val Asn Ala Ala Pro Val Met Leu Phe Met Lys Gly Ser Pro Ser Glu
        195                 200                 205 cct aaa tgc ggg ttt tcg aga caa ctt gtg ggt atc ttg aga gaa cat      672
Pro Lys Cys Gly Phe Ser Arg Gln Leu Val Gly Ile Leu Arg Glu His
    210                 215                 220 caa gta aga ttt ggc ttc ttt gat ata tta aga gac gaa tct gtt aga      720
Gln Val Arg Phe Gly Phe Phe Asp Ile Leu Arg Asp Glu Ser Val Arg
225                 230                 235                 240 caa aac ttg aaa aag ttt tct gaa tgg cca act ttc cct caa ctt tat      768
Gln Asn Leu Lys Lys Phe Ser Glu Trp Pro Thr Phe Pro Gln Leu Tyr
                245                 250                 255 ata aat ggg gag ttt caa ggc ggt tta gac att atc aag gaa tcc ttg      816
Ile Asn Gly Glu Phe Gln Gly Gly Leu Asp Ile Ile Lys Glu Ser Leu
            260                 265                 270 gag gaa gac cct gat ttt ttg cag cat gct ctc caa tct taa              858
Glu Glu Asp Pro Asp Phe Leu Gln His Ala Leu Gln Ser
        275                 280                 285

<210> SEQ ID NO 6
<211> LENGTH: 285
<212> TYPE: PRT
<213> ORGANISM: Saccharomyces cerevisiae

<400> SEQUENCE: 6

Met Cys Ser Phe Gln Val Pro Ser Ala Phe Ser Phe Asn Tyr Thr Ser
1               5                   10                  15

Tyr Cys Tyr Lys Arg His Gln Ala Arg Tyr Tyr Thr Ala Ala Lys Leu
            20                  25                  30

Phe Gln Glu Met Pro Val Ile Glu Ile Asn Asp Gln Gly Gln Phe Thr
        35                  40                  45

Tyr Leu Thr Thr Thr Ala Ala Gly Asp Lys Leu Ile Val Leu Tyr Phe
    50                  55                  60

His Thr Ser Trp Ala Glu Pro Cys Lys Ala Leu Lys Gln Val Phe Glu
65                  70                  75                  80

Ala Ile Ser Asn Glu Pro Ser Asn Ser Asn Val Ser Phe Leu Ser Ile
                85                  90                  95

Asp Ala Asp Glu Asn Ser Glu Ile Ser Glu Leu Phe Glu Ile Ser Ala
                100                 105                 110

Val Pro Tyr Phe Ile Ile Ile His Lys Gly Thr Ile Leu Lys Glu Leu
            115                 120                 125

Ser Gly Ala Asp Pro Lys Glu Tyr Val Ser Leu Leu Glu Asp Cys Lys
```

```
                130                 135                 140
Asn Ser Val Asn Ser Gly Ser Ser Gln Thr His Thr Met Glu Asn Ala
145                 150                 155                 160

Asn Val Asn Glu Gly Ser His Asn Asp Glu Asp Asp Asp Glu Glu
                165                 170                 175

Glu Glu Glu Glu Thr Glu Glu Gln Ile Asn Ala Arg Leu Thr Lys Leu
            180                 185                 190

Val Asn Ala Ala Pro Val Met Leu Phe Met Lys Gly Ser Pro Ser Glu
                195                 200                 205

Pro Lys Cys Gly Phe Ser Arg Gln Leu Val Gly Ile Leu Arg Glu His
        210                 215                 220

Gln Val Arg Phe Gly Phe Phe Asp Ile Leu Arg Asp Glu Ser Val Arg
225                 230                 235                 240

Gln Asn Leu Lys Lys Phe Ser Glu Trp Pro Thr Phe Pro Gln Leu Tyr
                245                 250                 255

Ile Asn Gly Glu Phe Gln Gly Gly Leu Asp Ile Ile Lys Glu Ser Leu
                260                 265                 270

Glu Glu Asp Pro Asp Phe Leu Gln His Ala Leu Gln Ser
            275                 280                 285

<210> SEQ ID NO 7
<211> LENGTH: 735
<212> TYPE: DNA
<213> ORGANISM: Saccharomyces cerevisiae
<220> FEATURE:
<221> NAME/KEY: CDS
<222> LOCATION: (1)..(732)
<223> OTHER INFORMATION: GRX4

<400> SEQUENCE: 7 atg act gtg gtt gaa ata aaa agc cag gac caa ttt acg caa cta acc       48
Met Thr Val Val Glu Ile Lys Ser Gln Asp Gln Phe Thr Gln Leu Thr
1               5                   10                  15 act aca aac gct gct aat aaa ctc att gtc tta tat ttt aaa gct caa       96
Thr Thr Asn Ala Ala Asn Lys Leu Ile Val Leu Tyr Phe Lys Ala Gln
            20                  25                  30 tgg gct gat cct tgc aaa act atg agc cag gtg cta gaa gct gtt agt      144
Trp Ala Asp Pro Cys Lys Thr Met Ser Gln Val Leu Glu Ala Val Ser
        35                  40                  45 gaa aaa gtt agg caa gag gat gtc cgg ttt tta tca ata gat gca gac      192
Glu Lys Val Arg Gln Glu Asp Val Arg Phe Leu Ser Ile Asp Ala Asp
    50                  55                  60 gaa cat cca gaa ata tca gac ctt ttt gag att gca gcc gta cca tac      240
Glu His Pro Glu Ile Ser Asp Leu Phe Glu Ile Ala Ala Val Pro Tyr
65                  70                  75                  80 ttc gtc ttc att caa aat ggt act att gta aaa gaa ata tca gcc gca      288
Phe Val Phe Ile Gln Asn Gly Thr Ile Val Lys Glu Ile Ser Ala Ala
                85                  90                  95 gat cct aag gag ttt gtg aaa agc tta gaa att ctt tcg aat gct tct      336
Asp Pro Lys Glu Phe Val Lys Ser Leu Glu Ile Leu Ser Asn Ala Ser
            100                 105                 110 gcc tca cta gcg aac aat gcc aag ggt cct aaa tct acg tct gat gag      384
Ala Ser Leu Ala Asn Asn Ala Lys Gly Pro Lys Ser Thr Ser Asp Glu
        115                 120                 125 gaa agc agc ggg tct tcc gat gat gaa gag gac gaa act gaa gaa gaa      432
Glu Ser Ser Gly Ser Ser Asp Asp Glu Glu Asp Glu Thr Glu Glu Glu
    130                 135                 140 ata aat gct agg ctg gtg aag cta gta caa gct gca cct gtg atg cta      480
Ile Asn Ala Arg Leu Val Lys Leu Val Gln Ala Ala Pro Val Met Leu
145                 150                 155                 160
```

```
ttc atg aaa gga agc cca tca gaa cct aaa tgc gga ttt tct aga cag    528
Phe Met Lys Gly Ser Pro Ser Glu Pro Lys Cys Gly Phe Ser Arg Gln
            165                 170                 175 tta gtt ggt atc ctc aga gaa cac caa ata agg ttc gga ttt ttt gat    576
Leu Val Gly Ile Leu Arg Glu His Gln Ile Arg Phe Gly Phe Phe Asp
        180                 185                 190 ata tta aga gac gaa aac gtt aga caa agc ttg aag aag ttt tct gat    624
Ile Leu Arg Asp Glu Asn Val Arg Gln Ser Leu Lys Lys Phe Ser Asp
            195                 200                 205 tgg cct act ttt cct cag tta tat atc aat ggg gag ttc cag gga ggt    672
Trp Pro Thr Phe Pro Gln Leu Tyr Ile Asn Gly Glu Phe Gln Gly Gly
        210                 215                 220 ttg gat att atc aag gaa tct ata gaa gaa gat cct gaa tat ttc caa    720
Leu Asp Ile Ile Lys Glu Ser Ile Glu Glu Asp Pro Glu Tyr Phe Gln
225                 230                 235                 240 cat gct cta cag taa                                                735
His Ala Leu Gln
```

<210> SEQ ID NO 8
<211> LENGTH: 244
<212> TYPE: PRT
<213> ORGANISM: Saccharomyces cerevisiae

<400> SEQUENCE: 8

```
Met Thr Val Val Glu Ile Lys Ser Gln Asp Gln Phe Thr Gln Leu Thr
1               5                   10                  15

Thr Thr Asn Ala Ala Asn Lys Leu Ile Val Leu Tyr Phe Lys Ala Gln
            20                  25                  30

Trp Ala Asp Pro Cys Lys Thr Met Ser Gln Val Leu Glu Ala Val Ser
        35                  40                  45

Glu Lys Val Arg Gln Glu Asp Val Arg Phe Leu Ser Ile Asp Ala Asp
    50                  55                  60

Glu His Pro Glu Ile Ser Asp Leu Phe Glu Ile Ala Ala Val Pro Tyr
65                  70                  75                  80

Phe Val Phe Ile Gln Asn Gly Thr Ile Val Lys Glu Ile Ser Ala Ala
                85                  90                  95

Asp Pro Lys Glu Phe Val Lys Ser Leu Glu Ile Leu Ser Asn Ala Ser
            100                 105                 110

Ala Ser Leu Ala Asn Asn Ala Lys Gly Pro Lys Ser Thr Ser Asp Glu
        115                 120                 125

Glu Ser Ser Gly Ser Ser Asp Asp Glu Glu Asp Glu Thr Glu Glu Glu
    130                 135                 140

Ile Asn Ala Arg Leu Val Lys Leu Val Gln Ala Ala Pro Val Met Leu
145                 150                 155                 160

Phe Met Lys Gly Ser Pro Ser Glu Pro Lys Cys Gly Phe Ser Arg Gln
                165                 170                 175

Leu Val Gly Ile Leu Arg Glu His Gln Ile Arg Phe Gly Phe Phe Asp
            180                 185                 190

Ile Leu Arg Asp Glu Asn Val Arg Gln Ser Leu Lys Lys Phe Ser Asp
        195                 200                 205

Trp Pro Thr Phe Pro Gln Leu Tyr Ile Asn Gly Glu Phe Gln Gly Gly
    210                 215                 220

Leu Asp Ile Ile Lys Glu Ser Ile Glu Glu Asp Pro Glu Tyr Phe Gln
225                 230                 235                 240

His Ala Leu Gln
```

<210> SEQ ID NO 9
<211> LENGTH: 453
<212> TYPE: DNA
<213> ORGANISM: Saccharomyces cerevisiae
<220> FEATURE:
<221> NAME/KEY: CDS
<222> LOCATION: (1)..(450)
<223> OTHER INFORMATION: GRX5

<400> SEQUENCE: 9

```
atg ttt ctc cca aaa ttc aat ccc ata agg tca ttt tcc ccc atc ctc      48
Met Phe Leu Pro Lys Phe Asn Pro Ile Arg Ser Phe Ser Pro Ile Leu
1               5                   10                  15 cgg gct aag act ctt ctt cgt tac caa aat cgg atg tat ttg agc aca      96
Arg Ala Lys Thr Leu Leu Arg Tyr Gln Asn Arg Met Tyr Leu Ser Thr
            20                  25                  30 gag ata aga aaa gct att gaa gat gcc atc gaa tcg gct cca gtg gtt     144
Glu Ile Arg Lys Ala Ile Glu Asp Ala Ile Glu Ser Ala Pro Val Val
        35                  40                  45 ctt ttc atg aaa ggt act cct gaa ttt ccc aag tgt gga ttt tca aga     192
Leu Phe Met Lys Gly Thr Pro Glu Phe Pro Lys Cys Gly Phe Ser Arg
    50                  55                  60 gca acc att gga tta tta gga aat caa ggc gtt gac ccg gcc aaa ttt     240
Ala Thr Ile Gly Leu Leu Gly Asn Gln Gly Val Asp Pro Ala Lys Phe
65                  70                  75                  80 gcg gct tat aat gtt tta gaa gac cca gag cta cgt gaa ggt atc aaa     288
Ala Ala Tyr Asn Val Leu Glu Asp Pro Glu Leu Arg Glu Gly Ile Lys
                85                  90                  95 gag ttt tca gaa tgg cca act att cca cag tta tat gta aac aaa gaa     336
Glu Phe Ser Glu Trp Pro Thr Ile Pro Gln Leu Tyr Val Asn Lys Glu
            100                 105                 110 ttc att ggt gga tgt gat gtt att aca agt atg gca cgc tct ggt gaa     384
Phe Ile Gly Gly Cys Asp Val Ile Thr Ser Met Ala Arg Ser Gly Glu
        115                 120                 125 ttg gcc gat ttg cta gaa gag gca cag gca ttg gta cct gaa gaa gaa     432
Leu Ala Asp Leu Leu Glu Glu Ala Gln Ala Leu Val Pro Glu Glu Glu
    130                 135                 140 gaa gaa acc aaa gat cgt tga                                          453
Glu Glu Thr Lys Asp Arg
145                 150
```

<210> SEQ ID NO 10
<211> LENGTH: 150
<212> TYPE: PRT
<213> ORGANISM: Saccharomyces cerevisiae

<400> SEQUENCE: 10

```
Met Phe Leu Pro Lys Phe Asn Pro Ile Arg Ser Phe Ser Pro Ile Leu
1               5                   10                  15

Arg Ala Lys Thr Leu Leu Arg Tyr Gln Asn Arg Met Tyr Leu Ser Thr
            20                  25                  30

Glu Ile Arg Lys Ala Ile Glu Asp Ala Ile Glu Ser Ala Pro Val Val
        35                  40                  45

Leu Phe Met Lys Gly Thr Pro Glu Phe Pro Lys Cys Gly Phe Ser Arg
    50                  55                  60

Ala Thr Ile Gly Leu Leu Gly Asn Gln Gly Val Asp Pro Ala Lys Phe
65                  70                  75                  80

Ala Ala Tyr Asn Val Leu Glu Asp Pro Glu Leu Arg Glu Gly Ile Lys
                85                  90                  95

Glu Phe Ser Glu Trp Pro Thr Ile Pro Gln Leu Tyr Val Asn Lys Glu
            100                 105                 110
```

```
        Phe Ile Gly Gly Cys Asp Val Ile Thr Ser Met Ala Arg Ser Gly Glu
                115                 120                 125

Leu Ala Asp Leu Leu Glu Glu Ala Gln Ala Leu Val Pro Glu Glu Glu
            130                 135                 140

Glu Glu Thr Lys Asp Arg
        145                 150

<210> SEQ ID NO 11
<211> LENGTH: 539
<212> TYPE: DNA
<213> ORGANISM: Saccharomyces cerevisiae
<220> FEATURE:
<221> NAME/KEY: CDS
<222> LOCATION: (1)..(312)
<223> OTHER INFORMATION: THX1

<400> SEQUENCE: 11 atg gtc act caa tta aaa tcc gct tct gaa tac gac agt gct tta gca       48
Met Val Thr Gln Leu Lys Ser Ala Ser Glu Tyr Asp Ser Ala Leu Ala
1               5                   10                  15 tct ggc gac aag tta gtc gtt gtt gac ttt ttt gcc aca tgg tgt ggg       96
Ser Gly Asp Lys Leu Val Val Val Asp Phe Phe Ala Thr Trp Cys Gly
                20                  25                  30 cca tgt aaa atg att gca cca atg att gaa aag ttt gca gaa caa tat      144
Pro Cys Lys Met Ile Ala Pro Met Ile Glu Lys Phe Ala Glu Gln Tyr
            35                  40                  45 tct gac gct gct ttt tac aag ttg gat gtt gat gaa gtc tca gat gtt      192
Ser Asp Ala Ala Phe Tyr Lys Leu Asp Val Asp Glu Val Ser Asp Val
        50                  55                  60 gct caa aaa gct gaa gtt tct tcc atg cct acc cta atc ttc tac aag      240
Ala Gln Lys Ala Glu Val Ser Ser Met Pro Thr Leu Ile Phe Tyr Lys
65                  70                  75                  80 ggc ggt aag gag gtt acc aga gtc gtc ggt gcc aac cca gct gct atc      288
Gly Gly Lys Glu Val Thr Arg Val Val Gly Ala Asn Pro Ala Ala Ile
                85                  90                  95 aag caa gct att gct tcc aac gta tagttgccgg tatattaacg ctacgtaaag     342
Lys Gln Ala Ile Ala Ser Asn Val
                100 tacatcatgt ttaccagttt aaataaacaa ttttaaaaag aaactctatt acatctatct    402 atcattattt tcttcattgt ctattgtata tttcatcatc ggtgtaacca agaatgtata    462 aaatgtcagt catgctcttg gtattcaact tacaaggtgc agctttctgc acctttggct    522 tggcgttcca tgcgatc                                                  539

<210> SEQ ID NO 12
<211> LENGTH: 104
<212> TYPE: PRT
<213> ORGANISM: Saccharomyces cerevisiae

<400> SEQUENCE: 12

Met Val Thr Gln Leu Lys Ser Ala Ser Glu Tyr Asp Ser Ala Leu Ala
1               5                   10                  15

Ser Gly Asp Lys Leu Val Val Val Asp Phe Phe Ala Thr Trp Cys Gly
                20                  25                  30

Pro Cys Lys Met Ile Ala Pro Met Ile Glu Lys Phe Ala Glu Gln Tyr
            35                  40                  45

Ser Asp Ala Ala Phe Tyr Lys Leu Asp Val Asp Glu Val Ser Asp Val
        50                  55                  60

Ala Gln Lys Ala Glu Val Ser Ser Met Pro Thr Leu Ile Phe Tyr Lys
65                  70                  75                  80
```

```
Gly Gly Lys Glu Val Thr Arg Val Val Gly Ala Asn Pro Ala Ala Ile
            85                  90                  95

Lys Gln Ala Ile Ala Ser Asn Val
            100

<210> SEQ ID NO 13
<211> LENGTH: 313
<212> TYPE: DNA
<213> ORGANISM: Saccharomyces cerevisiae
<220> FEATURE:
<221> NAME/KEY: CDS
<222> LOCATION: (1)..(309)
<223> OTHER INFORMATION: THX2

<400> SEQUENCE: 13 atg gtt act caa ttc aaa act gcc agc gaa ttc gac tct gca att gct      48
Met Val Thr Gln Phe Lys Thr Ala Ser Glu Phe Asp Ser Ala Ile Ala
1               5                   10                  15 caa gac aag cta gtt gtc gta gat ttc tac gcc act tgg tgc ggt cca      96
Gln Asp Lys Leu Val Val Val Asp Phe Tyr Ala Thr Trp Cys Gly Pro
            20                  25                  30 tgt aaa atg att gct cca atg att gaa aaa ttc tct gaa caa tac cca     144
Cys Lys Met Ile Ala Pro Met Ile Glu Lys Phe Ser Glu Gln Tyr Pro
        35                  40                  45 caa gct gat ttc tat aaa ttg gat gtc gat gaa ttg ggt gat gtt gca     192
Gln Ala Asp Phe Tyr Lys Leu Asp Val Asp Glu Leu Gly Asp Val Ala
    50                  55                  60 caa aag aat gaa gtt tcc gct atg cca act ttg ctt cta ttc aag aac     240
Gln Lys Asn Glu Val Ser Ala Met Pro Thr Leu Leu Leu Phe Lys Asn
65                  70                  75                  80 ggt aag gaa gtt gca aag gtt gtt ggt gcc aac cca gcg gct att aag     288
Gly Lys Glu Val Ala Lys Val Val Gly Ala Asn Pro Ala Ala Ile Lys
                85                  90                  95 caa gcc att gct gct aat gct taaa                                    313
Gln Ala Ile Ala Ala Asn Ala
            100

<210> SEQ ID NO 14
<211> LENGTH: 103
<212> TYPE: PRT
<213> ORGANISM: Saccharomyces cerevisiae

<400> SEQUENCE: 14

Met Val Thr Gln Phe Lys Thr Ala Ser Glu Phe Asp Ser Ala Ile Ala
1               5                   10                  15

Gln Asp Lys Leu Val Val Val Asp Phe Tyr Ala Thr Trp Cys Gly Pro
            20                  25                  30

Cys Lys Met Ile Ala Pro Met Ile Glu Lys Phe Ser Glu Gln Tyr Pro
        35                  40                  45

Gln Ala Asp Phe Tyr Lys Leu Asp Val Asp Glu Leu Gly Asp Val Ala
    50                  55                  60

Gln Lys Asn Glu Val Ser Ala Met Pro Thr Leu Leu Leu Phe Lys Asn
65                  70                  75                  80

Gly Lys Glu Val Ala Lys Val Val Gly Ala Asn Pro Ala Ala Ile Lys
                85                  90                  95

Gln Ala Ile Ala Ala Asn Ala
            100

<210> SEQ ID NO 15
<211> LENGTH: 657
<212> TYPE: DNA
<213> ORGANISM: Brassica napus
```

```
<220> FEATURE:
<221> NAME/KEY: CDS
<222> LOCATION: (126)..(485)
<223> OTHER INFORMATION: BN1106C12219

<400> SEQUENCE: 15
cgggtcgacg atttcgtttt gaacagccag caagattggg aacgaaagtc gagtgaaagg      60
aatctatagg agttgttctg tccgattcct tcaaagaata tctactgttt aggtaagagg     120 aagag atg ggt tct atg ttc agt gga aat cga ttg aac aag gaa gag atg    170
      Met Gly Ser Met Phe Ser Gly Asn Arg Leu Asn Lys Glu Glu Met
        1               5                  10                  15 gag gtt gtc gtg aac aag gcc aaa gag atc gtc tcc gct cac ccg gtc       218
Glu Val Val Val Asn Lys Ala Lys Glu Ile Val Ser Ala His Pro Val
             20                  25                  30 gtt gtc ttc agc aag act tac tgt ggt tat tgc cag agg gtg aaa cag       266
Val Val Phe Ser Lys Thr Tyr Cys Gly Tyr Cys Gln Arg Val Lys Gln
         35                  40                  45 ttg ttg aca cag cta ggt gca act ttt aaa gta ctt gag ctc gat gag       314
Leu Leu Thr Gln Leu Gly Ala Thr Phe Lys Val Leu Glu Leu Asp Glu
     50                  55                  60 atg agt gat gga ggt gag atc caa tca gct tta tct gag tgg act gga       362
Met Ser Asp Gly Gly Glu Ile Gln Ser Ala Leu Ser Glu Trp Thr Gly
 65                  70                  75 cag agc act gtt cct aat gtt ttc atc aaa ggc aaa cat atc ggt gga       410
Gln Ser Thr Val Pro Asn Val Phe Ile Lys Gly Lys His Ile Gly Gly
 80                  85                  90                  95 tgc gat aga gtg atg gag agt aac aag caa ggc aag ctt gtg cct cta       458
Cys Asp Arg Val Met Glu Ser Asn Lys Gln Gly Lys Leu Val Pro Leu
                100                 105                 110 ctt act gaa gct ggt gct atc tcc aat taactcttcc cagcttgagt             505
Leu Thr Glu Ala Gly Ala Ile Ser Asn
            115                 120 gaaaactctg aaactataaa cagtggaaat gaagaagaat gttatatgtt acatactgtc    565
aagtacccaa ataaggaaag atacttgtgg ttttcacttt gctttaaaca aaacattaac    625
actgctgtgc tgtttggctc tcctttgtta tg                                  657

<210> SEQ ID NO 16
<211> LENGTH: 120
<212> TYPE: PRT
<213> ORGANISM: Brassica napus

<400> SEQUENCE: 16

Met Gly Ser Met Phe Ser Gly Asn Arg Leu Asn Lys Glu Glu Met Glu
  1               5                  10                  15

Val Val Val Asn Lys Ala Lys Glu Ile Val Ser Ala His Pro Val Val
             20                  25                  30

Val Phe Ser Lys Thr Tyr Cys Gly Tyr Cys Gln Arg Val Lys Gln Leu
         35                  40                  45

Leu Thr Gln Leu Gly Ala Thr Phe Lys Val Leu Glu Leu Asp Glu Met
     50                  55                  60

Ser Asp Gly Gly Glu Ile Gln Ser Ala Leu Ser Glu Trp Thr Gly Gln
 65                  70                  75                  80

Ser Thr Val Pro Asn Val Phe Ile Lys Gly Lys His Ile Gly Gly Cys
                 85                  90                  95

Asp Arg Val Met Glu Ser Asn Lys Gln Gly Lys Leu Val Pro Leu Leu
            100                 105                 110

Thr Glu Ala Gly Ala Ile Ser Asn
        115                 120
```

<210> SEQ ID NO 17
<211> LENGTH: 463
<212> TYPE: DNA
<213> ORGANISM: Brassica napus
<220> FEATURE:
<221> NAME/KEY: CDS
<222> LOCATION: (26)..(433)
<223> OTHER INFORMATION: BN1106C21909

<400> SEQUENCE: 17

```
aattcccggg tcgacaggtg agcga atg gcg atg gtt ggg cac cgt cct cgc        52
                            Met Ala Met Val Gly His Arg Pro Arg
                            1               5 cgt gtt gaa gtc acg gcg gtt cac ata ctc cta ata cta gcg gtg gtt       100
Arg Val Glu Val Thr Ala Val His Ile Leu Leu Ile Leu Ala Val Val
10              15                  20                  25 ccc agc gat ctg tca atc tct gca gga gct gag aaa tcg gtg gct gca       148
Pro Ser Asp Leu Ser Ile Ser Ala Gly Ala Glu Lys Ser Val Ala Ala
                30                  35                  40 ttt gtg cag aac gcc ata ttg tcc aac aag att gtc atc ttc tcc aag       196
Phe Val Gln Asn Ala Ile Leu Ser Asn Lys Ile Val Ile Phe Ser Lys
            45                  50                  55 tcc tac tgc ccg tat tgc ttg cgc tcg aaa cgc att ttc aga gaa ctt       244
Ser Tyr Cys Pro Tyr Cys Leu Arg Ser Lys Arg Ile Phe Arg Glu Leu
        60                  65                  70 aag gaa cag cct ttt gtc gtg gag ctt gat ctc aga gag gac gga gat       292
Lys Glu Gln Pro Phe Val Val Glu Leu Asp Leu Arg Glu Asp Gly Asp
75                  80                  85 aaa ata cag tac gag ctt ctg gaa ttt gtt ggt cgc cgt acc gtc ccc       340
Lys Ile Gln Tyr Glu Leu Leu Glu Phe Val Gly Arg Arg Thr Val Pro
90                  95                  100                 105 caa gtt ttt gtt aac ggc aag cat att ggt ggc tct gat gat ctt gca       388
Gln Val Phe Val Asn Gly Lys His Ile Gly Gly Ser Asp Asp Leu Ala
            110                 115                 120 gat tct gtg gag aat ggt cag ttg caa aag ctt ctt gct gct agt           433
Asp Ser Val Glu Asn Gly Gln Leu Gln Lys Leu Leu Ala Ala Ser
        125                 130                 135 tagactttc agaagctgga acttatgttg                                       463
```

<210> SEQ ID NO 18
<211> LENGTH: 136
<212> TYPE: PRT
<213> ORGANISM: Brassica napus

<400> SEQUENCE: 18

```
Met Ala Met Val Gly His Arg Pro Arg Arg Val Glu Val Thr Ala Val
1               5                   10                  15

His Ile Leu Leu Ile Leu Ala Val Val Pro Ser Asp Leu Ser Ile Ser
                20                  25                  30

Ala Gly Ala Glu Lys Ser Val Ala Ala Phe Val Gln Asn Ala Ile Leu
            35                  40                  45

Ser Asn Lys Ile Val Ile Phe Ser Lys Ser Tyr Cys Pro Tyr Cys Leu
        50                  55                  60

Arg Ser Lys Arg Ile Phe Arg Glu Leu Lys Glu Gln Pro Phe Val Val
65                  70                  75                  80

Glu Leu Asp Leu Arg Glu Asp Gly Asp Lys Ile Gln Tyr Glu Leu Leu
                85                  90                  95

Glu Phe Val Gly Arg Arg Thr Val Pro Gln Val Phe Val Asn Gly Lys
            100                 105                 110
```

His Ile Gly Gly Ser Asp Asp Leu Ala Asp Ser Val Glu Asn Gly Gln
        115                 120                 125

Leu Gln Lys Leu Leu Ala Ala Ser
        130                 135

<210> SEQ ID NO 19
<211> LENGTH: 672
<212> TYPE: DNA
<213> ORGANISM: Brassica napus
<220> FEATURE:
<221> NAME/KEY: CDS
<222> LOCATION: (22)..(540)
<223> OTHER INFORMATION: BN1106C2202

<400> SEQUENCE: 19

```
cctaagggtc agaaaatagc c atg gca gtc aca gct ttc aac cca ctg aag       51
                        Met Ala Val Thr Ala Phe Asn Pro Leu Lys
                         1               5                  10 ctt gca tct tcg cct cga gat tcg ttt cct tca atc tcc tct tca act       99
Leu Ala Ser Ser Pro Arg Asp Ser Phe Pro Ser Ile Ser Ser Ser Thr
            15                  20                  25 tct tat tcg gtg tct ctg ata agc ttc ggt ttc aga aac tcc gtc gga      147
Ser Tyr Ser Val Ser Leu Ile Ser Phe Gly Phe Arg Asn Ser Val Gly
        30                  35                  40 tct cct ctc aag aaa tgt tct cta aag cag acg tgt tct gtt cga gcc      195
Ser Pro Leu Lys Lys Cys Ser Leu Lys Gln Thr Cys Ser Val Arg Ala
    45                  50                  55 atg tct tct tcg tca ttc gaa tcg ggg atg gag gag agc gtg aag aaa      243
Met Ser Ser Ser Ser Phe Glu Ser Gly Met Glu Glu Ser Val Lys Lys
60                  65                  70 acg gtg gct gat aac aca gtc gtt gtt tac tcg aaa act tgg tgc cca      291
Thr Val Ala Asp Asn Thr Val Val Val Tyr Ser Lys Thr Trp Cys Pro
75                  80                  85                  90 tac tgt tct gaa gtg aag aca ttg ttc aag aga ctt ggt gtt cag cca      339
Tyr Cys Ser Glu Val Lys Thr Leu Phe Lys Arg Leu Gly Val Gln Pro
                95                 100                 105 ctg gtg gtt gag ttg gat gaa ctt ggt cca caa ggg aca caa cta cag      387
Leu Val Val Glu Leu Asp Glu Leu Gly Pro Gln Gly Thr Gln Leu Gln
        110                 115                 120 aag gta ctg gaa aca ctt act ggg caa cgc act gtt cct aat gtg ttc      435
Lys Val Leu Glu Thr Leu Thr Gly Gln Arg Thr Val Pro Asn Val Phe
    125                 130                 135 gtc gga ggc aag cac att ggt ggc tgc aca gat aca gta aac ctg aac      483
Val Gly Gly Lys His Ile Gly Gly Cys Thr Asp Thr Val Asn Leu Asn
140                 145                 150 agg aaa gga gaa ctg gaa ttg atg tta gct gaa gcc aac gct aaa acc      531
Arg Lys Gly Glu Leu Glu Leu Met Leu Ala Glu Ala Asn Ala Lys Thr
155                 160                 165                 170 gat cag act tgaggaaatg atggaaactg gctttggaga tgaacccact              580
Asp Gln Thr tctctctctc tctcttttgt aaacattgaa cctcgatttc tctctctaca ctttctagaa    640
catcattcaa ataatacatg aacagaggta aa                                  672
```

<210> SEQ ID NO 20
<211> LENGTH: 173
<212> TYPE: PRT
<213> ORGANISM: Brassica napus

<400> SEQUENCE: 20

Met Ala Val Thr Ala Phe Asn Pro Leu Lys Leu Ala Ser Ser Pro Arg
 1               5                  10                  15

```
Asp Ser Phe Pro Ser Ile Ser Ser Thr Ser Tyr Ser Val Ser Leu
            20                  25                  30

Ile Ser Phe Gly Phe Arg Asn Ser Val Gly Ser Pro Leu Lys Lys Cys
        35                  40                  45

Ser Leu Lys Gln Thr Cys Ser Val Arg Ala Met Ser Ser Ser Ser Phe
 50                  55                  60

Glu Ser Gly Met Glu Glu Ser Val Lys Lys Thr Val Ala Asp Asn Thr
 65                  70                  75                  80

Val Val Val Tyr Ser Lys Thr Trp Cys Pro Tyr Cys Ser Glu Val Lys
                85                  90                  95

Thr Leu Phe Lys Arg Leu Gly Val Gln Pro Leu Val Val Glu Leu Asp
            100                 105                 110

Glu Leu Gly Pro Gln Gly Thr Gln Leu Gln Lys Val Leu Glu Thr Leu
        115                 120                 125

Thr Gly Gln Arg Thr Val Pro Asn Val Phe Val Gly Gly Lys His Ile
130                 135                 140

Gly Gly Cys Thr Asp Thr Val Asn Leu Asn Arg Lys Gly Glu Leu Glu
145                 150                 155                 160

Leu Met Leu Ala Glu Ala Asn Ala Lys Thr Asp Gln Thr
            165                 170
```

<210> SEQ ID NO 21
<211> LENGTH: 627
<212> TYPE: DNA
<213> ORGANISM: Brassica napus
<220> FEATURE:
<221> NAME/KEY: CDS
<222> LOCATION: (10)..(411)
<223> OTHER INFORMATION: BN1106C2582

<400> SEQUENCE: 21

```
aagggaacg atg aca atg atg aga tct ttc tcg atg gca atg ttg ctc gtc         51
          Met Thr Met Met Arg Ser Phe Ser Met Ala Met Leu Leu Val
           1               5                  10 gca cta gtt tca tcc atc tct att gtt tct tcg gct tct tca tcc cct          99
Ala Leu Val Ser Ser Ile Ser Ile Val Ser Ser Ala Ser Ser Ser Pro
 15                  20                  25                  30 gaa gcc gag ttt gtt aag aag acc atc tct tcc cac aag atc gtt atc         147
Glu Ala Glu Phe Val Lys Lys Thr Ile Ser Ser His Lys Ile Val Ile
                 35                  40                  45 ttc tcc aaa tcc tac tgc ccg tat tgc agg aga gcc aaa tct gtg ttc         195
Phe Ser Lys Ser Tyr Cys Pro Tyr Cys Arg Arg Ala Lys Ser Val Phe
             50                  55                  60 agt gag ctg gat cag gtt cct cat gtt gtg gag ctt gat gaa aga gaa         243
Ser Glu Leu Asp Gln Val Pro His Val Val Glu Leu Asp Glu Arg Glu
 65                  70                  75 gat ggg tgg aac gtt cag agt gca ctt gga gag att gtt gga agg cga         291
Asp Gly Trp Asn Val Gln Ser Ala Leu Gly Glu Ile Val Gly Arg Arg
         80                  85                  90 aca gta cca cag gtt ttc att aac gga aag cac att gga gga tca gac         339
Thr Val Pro Gln Val Phe Ile Asn Gly Lys His Ile Gly Gly Ser Asp
 95                 100                 105                 110 gat act gta gaa gcg cat gaa agc ggt gaa ctg gcc aag ctt ctc ggt         387
Asp Thr Val Glu Ala His Glu Ser Gly Glu Leu Ala Lys Leu Leu Gly
             115                 120                 125 ctt tcc acc aaa gct gaa ctc tag gttcaatgta gttgtagttg gagtgatatt        441
Leu Ser Thr Lys Ala Glu Leu
                130 caggtgtaag cacttccatt ttccagtttt atgataactt gtaatgtgtt ctgaaggtta        501
```

```
taaacgtctt gtcatagctt tgtgaaacga tattaaaggc tacgagttgg attgagattc      561
aaatctggtc atgcttcaag cgaaaaaaaa aaaacgaaa tcgtcgctct agagattccg       621
gggcgg                                                                 627
```

```
<210> SEQ ID NO 22
<211> LENGTH: 133
<212> TYPE: PRT
<213> ORGANISM: Brassica napus

<400> SEQUENCE: 22
```

```
Met Thr Met Met Arg Ser Phe Ser Met Ala Met Leu Leu Val Ala Leu
1               5                   10                  15

Val Ser Ser Ile Ser Ile Val Ser Ser Ala Ser Ser Pro Glu Ala
            20                  25                  30

Glu Phe Val Lys Lys Thr Ile Ser Ser His Lys Ile Val Ile Phe Ser
            35                  40                  45

Lys Ser Tyr Cys Pro Tyr Cys Arg Arg Ala Lys Ser Val Phe Ser Glu
    50                  55                  60

Leu Asp Gln Val Pro His Val Val Glu Leu Asp Glu Arg Glu Asp Gly
65                  70                  75                  80

Trp Asn Val Gln Ser Ala Leu Gly Glu Ile Val Gly Arg Arg Thr Val
                85                  90                  95

Pro Gln Val Phe Ile Asn Gly Lys His Ile Gly Gly Ser Asp Asp Thr
            100                 105                 110

Val Glu Ala His Glu Ser Gly Glu Leu Ala Lys Leu Leu Gly Leu Ser
            115                 120                 125

Thr Lys Ala Glu Leu
    130
```

```
<210> SEQ ID NO 23
<211> LENGTH: 743
<212> TYPE: DNA
<213> ORGANISM: Brassica napus
<220> FEATURE:
<221> NAME/KEY: CDS
<222> LOCATION: (42)..(680)
<223> OTHER INFORMATION: BN1106C23043

<400> SEQUENCE: 23
```

```
cgcgactgtg tgtaatctaa agcaatcgta gatcttcgaa g atg ggt ggt gcg gtg      56
                                             Met Gly Gly Ala Val
                                             1               5 aag gat att gct tca aag tcc gag ctt gat aac att cgc cag agc ggc       104
Lys Asp Ile Ala Ser Lys Ser Glu Leu Asp Asn Ile Arg Gln Ser Gly
            10                  15                  20 gca ccg gtg gtg ctt cac ttc tgg gct tcg tgg tgt gat gct tcg aag       152
Ala Pro Val Val Leu His Phe Trp Ala Ser Trp Cys Asp Ala Ser Lys
            25                  30                  35 cag atg gat caa gtc ttc tct cac ctc gct acc gac ttc cct cgc gcc       200
Gln Met Asp Gln Val Phe Ser His Leu Ala Thr Asp Phe Pro Arg Ala
        40                  45                  50 cac ttc ttt agg gta gaa gct gag gaa cat cct gag ata tct gaa gct       248
His Phe Phe Arg Val Glu Ala Glu Glu His Pro Glu Ile Ser Glu Ala
    55                  60                  65 tac tct gtt tct gct gtt ccc tat ttc gtc ttc ttc aag gat ggc aaa       296
Tyr Ser Val Ser Ala Val Pro Tyr Phe Val Phe Phe Lys Asp Gly Lys
70                  75                  80                  85 gct gtg gat aca ctt gag gga gca gat cca tca agt tta gcc aat aaa       344
Ala Val Asp Thr Leu Glu Gly Ala Asp Pro Ser Ser Leu Ala Asn Lys
                90                  95                  100
```

```
gtt ggc aaa gtc gct ggt tcc agc act tct gct gag cct gct gct cct      392
Val Gly Lys Val Ala Gly Ser Ser Thr Ser Ala Glu Pro Ala Ala Pro
            105                 110                 115 gca agc cta ggg ctg gct gca ggg cca acg att ctc gaa acc gtc aag      440
Ala Ser Leu Gly Leu Ala Ala Gly Pro Thr Ile Leu Glu Thr Val Lys
        120                 125                 130 gag aat gcg aaa gct act tcg aaa gac cga gct cag cct tta tcc tcc      488
Glu Asn Ala Lys Ala Thr Ser Lys Asp Arg Ala Gln Pro Leu Ser Ser
    135                 140                 145 acc acc aag gaa gct ctc aat acc cgt ttg gag aaa ctc acc aac tct      536
Thr Thr Lys Glu Ala Leu Asn Thr Arg Leu Glu Lys Leu Thr Asn Ser
150                 155                 160                 165 cac cct gtt atg ttg ttc atg aaa ggt acc cct gag gag cct atg tgc      584
His Pro Val Met Leu Phe Met Lys Gly Thr Pro Glu Glu Pro Met Cys
                170                 175                 180 ggt ttc agc aag aac gta gtt aac atc ttg aag gag gag gaa gtt gag      632
Gly Phe Ser Lys Asn Val Val Asn Ile Leu Lys Glu Glu Glu Val Glu
            185                 190                 195 ttc gga agt ttc gat ata ctt tcg gac aat gaa gtc cgt gaa ggt ctg      680
Phe Gly Ser Phe Asp Ile Leu Ser Asp Asn Glu Val Arg Glu Gly Leu
        200                 205                 210 aagaagttct tcaactggcc aacgtaccct cagctgtaca gcatcggaga gctactctgt    740
gga                                                                  743

<210> SEQ ID NO 24
<211> LENGTH: 213
<212> TYPE: PRT
<213> ORGANISM: Brassica napus

<400> SEQUENCE: 24

Met Gly Gly Ala Val Lys Asp Ile Ala Ser Lys Ser Glu Leu Asp Asn
1               5                   10                  15

Ile Arg Gln Ser Gly Ala Pro Val Val Leu His Phe Trp Ala Ser Trp
            20                  25                  30

Cys Asp Ala Ser Lys Gln Met Asp Gln Val Phe Ser His Leu Ala Thr
        35                  40                  45

Asp Phe Pro Arg Ala His Phe Phe Arg Val Glu Ala Glu Glu His Pro
    50                  55                  60

Glu Ile Ser Glu Ala Tyr Ser Val Ser Ala Val Pro Tyr Phe Val Phe
65                  70                  75                  80

Phe Lys Asp Gly Lys Ala Val Asp Thr Leu Glu Gly Ala Asp Pro Ser
                85                  90                  95

Ser Leu Ala Asn Lys Val Gly Lys Val Ala Gly Ser Ser Thr Ser Ala
            100                 105                 110

Glu Pro Ala Ala Pro Ala Ser Leu Gly Leu Ala Ala Gly Pro Thr Ile
        115                 120                 125

Leu Glu Thr Val Lys Glu Asn Ala Lys Ala Thr Ser Lys Asp Arg Ala
    130                 135                 140

Gln Pro Leu Ser Ser Thr Thr Lys Glu Ala Leu Asn Thr Arg Leu Glu
145                 150                 155                 160

Lys Leu Thr Asn Ser His Pro Val Met Leu Phe Met Lys Gly Thr Pro
                165                 170                 175

Glu Glu Pro Met Cys Gly Phe Ser Lys Asn Val Val Asn Ile Leu Lys
            180                 185                 190

Glu Glu Glu Val Glu Phe Gly Ser Phe Asp Ile Leu Ser Asp Asn Glu
        195                 200                 205
```

```
Val Arg Glu Gly Leu
        210

<210> SEQ ID NO 25
<211> LENGTH: 336
<212> TYPE: DNA
<213> ORGANISM: Arabidopsis thaliana
<220> FEATURE:
<221> NAME/KEY: CDS
<222> LOCATION: (1)..(333)
<223> OTHER INFORMATION: AtQ9FM49

<400> SEQUENCE: 25 atg gag gtg gtg gtg aac aag gct aaa gag atc gtc tct gct tat ccc      48
Met Glu Val Val Val Asn Lys Ala Lys Glu Ile Val Ser Ala Tyr Pro
1               5                   10                  15 gtt gtt gtc ttc agc aag aca tac tgt ggt tat tgc cag agg gtg aag      96
Val Val Val Phe Ser Lys Thr Tyr Cys Gly Tyr Cys Gln Arg Val Lys
            20                  25                  30 cag tta ctg acg cag cta gga gca act ttt aaa gta ctt gag ctc gat     144
Gln Leu Leu Thr Gln Leu Gly Ala Thr Phe Lys Val Leu Glu Leu Asp
        35                  40                  45 gaa atg agt gat gga ggt gag atc caa tca gct tta tca gag tgg act     192
Glu Met Ser Asp Gly Gly Glu Ile Gln Ser Ala Leu Ser Glu Trp Thr
    50                  55                  60 gga cag acc aca gtt cca aac gtc ttc atc aaa gga aac cac atc ggt     240
Gly Gln Thr Thr Val Pro Asn Val Phe Ile Lys Gly Asn His Ile Gly
65                  70                  75                  80 gga tgc gat aga gtg atg gag acc aac aag caa ggc aag ctt gtg cct     288
Gly Cys Asp Arg Val Met Glu Thr Asn Lys Gln Gly Lys Leu Val Pro
                85                  90                  95 cta ctt act gaa gct ggg gct att gca gat aac tct tct caa ctt tga     336
Leu Leu Thr Glu Ala Gly Ala Ile Ala Asp Asn Ser Ser Gln Leu
            100                 105                 110

<210> SEQ ID NO 26
<211> LENGTH: 111
<212> TYPE: PRT
<213> ORGANISM: Arabidopsis thaliana

<400> SEQUENCE: 26

Met Glu Val Val Val Asn Lys Ala Lys Glu Ile Val Ser Ala Tyr Pro
1               5                   10                  15

Val Val Val Phe Ser Lys Thr Tyr Cys Gly Tyr Cys Gln Arg Val Lys
            20                  25                  30

Gln Leu Leu Thr Gln Leu Gly Ala Thr Phe Lys Val Leu Glu Leu Asp
        35                  40                  45

Glu Met Ser Asp Gly Gly Glu Ile Gln Ser Ala Leu Ser Glu Trp Thr
    50                  55                  60

Gly Gln Thr Thr Val Pro Asn Val Phe Ile Lys Gly Asn His Ile Gly
65                  70                  75                  80

Gly Cys Asp Arg Val Met Glu Thr Asn Lys Gln Gly Lys Leu Val Pro
                85                  90                  95

Leu Leu Thr Glu Ala Gly Ala Ile Ala Asp Asn Ser Ser Gln Leu
            100                 105                 110

<210> SEQ ID NO 27
<211> LENGTH: 336
<212> TYPE: DNA
<213> ORGANISM: Arabidopsis thaliana
<220> FEATURE:
<221> NAME/KEY: CDS
<222> LOCATION: (1)..(333)
```

<223> OTHER INFORMATION: AtQ9FNE2

<400> SEQUENCE: 27

```
atg gcg atg cag aaa gct aag gag atc gtt aac agc gaa tca gtc gtt      48
Met Ala Met Gln Lys Ala Lys Glu Ile Val Asn Ser Glu Ser Val Val
1               5                   10                  15 gtt ttc agc aag act tat tgt cca tat tgc gtg aga gtg aag gag ctt      96
Val Phe Ser Lys Thr Tyr Cys Pro Tyr Cys Val Arg Val Lys Glu Leu
            20                  25                  30 ttg caa caa ttg gga gct aag ttc aag gcc gtt gag ctc gac acc gaa     144
Leu Gln Gln Leu Gly Ala Lys Phe Lys Ala Val Glu Leu Asp Thr Glu
        35                  40                  45 agt gat ggt agc caa att caa tca ggt ctc gca gaa tgg aca gga caa     192
Ser Asp Gly Ser Gln Ile Gln Ser Gly Leu Ala Glu Trp Thr Gly Gln
    50                  55                  60 cgt acc gtg cct aat gtg ttt ata gga gga aat cac atc ggt ggc tgt     240
Arg Thr Val Pro Asn Val Phe Ile Gly Gly Asn His Ile Gly Gly Cys
65                  70                  75                  80 gat gca aca tca aac ttg cat aaa gat ggg aag ttg gtt ccg ctg tta     288
Asp Ala Thr Ser Asn Leu His Lys Asp Gly Lys Leu Val Pro Leu Leu
                85                  90                  95 act gaa gct gga gcg atc gca gga aag act gca aca act tct gct taa    336
Thr Glu Ala Gly Ala Ile Ala Gly Lys Thr Ala Thr Thr Ser Ala
            100                 105                 110
```

<210> SEQ ID NO 28
<211> LENGTH: 111
<212> TYPE: PRT
<213> ORGANISM: Arabidopsis thaliana

<400> SEQUENCE: 28

```
Met Ala Met Gln Lys Ala Lys Glu Ile Val Asn Ser Glu Ser Val Val
1               5                   10                  15

Val Phe Ser Lys Thr Tyr Cys Pro Tyr Cys Val Arg Val Lys Glu Leu
            20                  25                  30

Leu Gln Gln Leu Gly Ala Lys Phe Lys Ala Val Glu Leu Asp Thr Glu
        35                  40                  45

Ser Asp Gly Ser Gln Ile Gln Ser Gly Leu Ala Glu Trp Thr Gly Gln
    50                  55                  60

Arg Thr Val Pro Asn Val Phe Ile Gly Gly Asn His Ile Gly Gly Cys
65                  70                  75                  80

Asp Ala Thr Ser Asn Leu His Lys Asp Gly Lys Leu Val Pro Leu Leu
                85                  90                  95

Thr Glu Ala Gly Ala Ile Ala Gly Lys Thr Ala Thr Thr Ser Ala
            100                 105                 110
```

<210> SEQ ID NO 29
<211> LENGTH: 393
<212> TYPE: DNA
<213> ORGANISM: Arabidopsis thaliana
<220> FEATURE:
<221> NAME/KEY: CDS
<222> LOCATION: (1)..(390)
<223> OTHER INFORMATION: AtQ9FVX1

<400> SEQUENCE: 29

```
atg gtt gac cag agt cct cgc cgt gtt gtc gtg gcg gcg ctc cta ttg      48
Met Val Asp Gln Ser Pro Arg Arg Val Val Val Ala Ala Leu Leu Leu
1               5                   10                  15 ttt gtg gtt ctg tgc gat ctt tcg aat tct gcg gga gct gcg aat tct      96
Phe Val Val Leu Cys Asp Leu Ser Asn Ser Ala Gly Ala Ala Asn Ser
            20                  25                  30
```

```
gtg tca gct ttc gtt cag aac gcc atc ttg tcc aac aag att gtc atc      144
Val Ser Ala Phe Val Gln Asn Ala Ile Leu Ser Asn Lys Ile Val Ile
    35                  40                  45 ttc tcc aaa tcc tac tgc ccg tat tgt ttg cgg tcg aaa cgt ata ttc      192
Phe Ser Lys Ser Tyr Cys Pro Tyr Cys Leu Arg Ser Lys Arg Ile Phe
 50                  55                  60 agc caa ctt aag gaa gag cca ttt gtt gtg gag ctt gat cag aga gag      240
Ser Gln Leu Lys Glu Glu Pro Phe Val Val Glu Leu Asp Gln Arg Glu
 65                  70                  75                  80 gac gga gat caa atc cag tat gag ctt tta gaa ttc gtt ggt cgt cgt      288
Asp Gly Asp Gln Ile Gln Tyr Glu Leu Leu Glu Phe Val Gly Arg Arg
                 85                  90                  95 act gtc ccg caa gtt ttt gtt aac ggc aag cat att ggt gga tca gat      336
Thr Val Pro Gln Val Phe Val Asn Gly Lys His Ile Gly Gly Ser Asp
            100                 105                 110 gat ctt gga gct gct ttg gag agt ggt cag ttg caa aag ctt ctt gct      384
Asp Leu Gly Ala Ala Leu Glu Ser Gly Gln Leu Gln Lys Leu Leu Ala
        115                 120                 125 gca agt tga                                                           393
Ala Ser
    130

<210> SEQ ID NO 30
<211> LENGTH: 130
<212> TYPE: PRT
<213> ORGANISM: Arabidopsis thaliana

<400> SEQUENCE: 30

Met Val Asp Gln Ser Pro Arg Arg Val Val Ala Ala Leu Leu Leu
 1               5                  10                  15

Phe Val Val Leu Cys Asp Leu Ser Asn Ser Ala Gly Ala Ala Asn Ser
                 20                  25                  30

Val Ser Ala Phe Val Gln Asn Ala Ile Leu Ser Asn Lys Ile Val Ile
            35                  40                  45

Phe Ser Lys Ser Tyr Cys Pro Tyr Cys Leu Arg Ser Lys Arg Ile Phe
 50                  55                  60

Ser Gln Leu Lys Glu Glu Pro Phe Val Val Glu Leu Asp Gln Arg Glu
 65                  70                  75                  80

Asp Gly Asp Gln Ile Gln Tyr Glu Leu Leu Glu Phe Val Gly Arg Arg
                 85                  90                  95

Thr Val Pro Gln Val Phe Val Asn Gly Lys His Ile Gly Gly Ser Asp
            100                 105                 110

Asp Leu Gly Ala Ala Leu Glu Ser Gly Gln Leu Gln Lys Leu Leu Ala
        115                 120                 125

Ala Ser
    130

<210> SEQ ID NO 31
<211> LENGTH: 629
<212> TYPE: DNA
<213> ORGANISM: Arabidopsis thaliana
<220> FEATURE:
<221> NAME/KEY: CDS
<222> LOCATION: (48)..(452)
<223> OTHER INFORMATION: AtQ9M457

<400> SEQUENCE: 31
ccacgcgtcc gtggcatctg aagaagaaga agaagaagaa aggagcc atg aca atg      56
                                                    Met Thr Met
                                                     1
```

```
ttt aga tct atc tcc atg gta atg ctg ctc gtc gca cta gtt aca ttc    104
Phe Arg Ser Ile Ser Met Val Met Leu Leu Val Ala Leu Val Thr Phe
    5                  10                  15 att tct atg gtt tct tct gct gct tcg tcc cca gaa gcc gac ttt gtt    152
Ile Ser Met Val Ser Ser Ala Ala Ser Ser Pro Glu Ala Asp Phe Val
 20              25                  30                      35 aag aag act atc tct tcc cat aag atc gtc att ttc tcc aaa tcc tac    200
Lys Lys Thr Ile Ser Ser His Lys Ile Val Ile Phe Ser Lys Ser Tyr
                40                  45                  50 tgc ccc tac tgc aag aaa gct aaa tca gtg ttc aga gag ctg gat caa    248
Cys Pro Tyr Cys Lys Lys Ala Lys Ser Val Phe Arg Glu Leu Asp Gln
            55                  60                  65 gtt cct tat gtt gtc gag ctt gat gaa aga gaa gat ggt tgg agc atc    296
Val Pro Tyr Val Val Glu Leu Asp Glu Arg Glu Asp Gly Trp Ser Ile
        70                  75                  80 cag act gca ctt gga gag att gtt gga agg cga aca gta ccg caa gtc    344
Gln Thr Ala Leu Gly Glu Ile Val Gly Arg Arg Thr Val Pro Gln Val
85                  90                  95 ttc att aac gga aaa cat ctc gga gga tca gat gat acc gta gat gcg    392
Phe Ile Asn Gly Lys His Leu Gly Gly Ser Asp Asp Thr Val Asp Ala
100                 105                 110                 115 tat gag agc ggt gaa ctc gcc aag ctt ctt ggt gtt tcc ggg aac aaa    440
Tyr Glu Ser Gly Glu Leu Ala Lys Leu Leu Gly Val Ser Gly Asn Lys
                120                 125                 130 gaa gct gaa ctc taggttatat atagttggaa gaattgataa cactctctgt         492
Glu Ala Glu Leu
            135 gatgcttagg tgtaagcaat tcaatttcca tttgtattgt gttctgcagc ttgatcatga   552 ccttgtgaca gcttgatctt gcctttaaa cgtatcttat caaagaccac attctgagtt    612 aaaaaaaaaa aaaaaaa                                                  629

<210> SEQ ID NO 32
<211> LENGTH: 135
<212> TYPE: PRT
<213> ORGANISM: Arabidopsis thaliana

<400> SEQUENCE: 32

Met Thr Met Phe Arg Ser Ile Ser Met Val Met Leu Leu Val Ala Leu
1               5                   10                  15

Val Thr Phe Ile Ser Met Val Ser Ser Ala Ala Ser Ser Pro Glu Ala
            20                  25                  30

Asp Phe Val Lys Lys Thr Ile Ser Ser His Lys Ile Val Ile Phe Ser
        35                  40                  45

Lys Ser Tyr Cys Pro Tyr Cys Lys Lys Ala Lys Ser Val Phe Arg Glu
50                  55                  60

Leu Asp Gln Val Pro Tyr Val Val Glu Leu Asp Glu Arg Glu Asp Gly
65                  70                  75                  80

Trp Ser Ile Gln Thr Ala Leu Gly Glu Ile Val Gly Arg Arg Thr Val
                85                  90                  95

Pro Gln Val Phe Ile Asn Gly Lys His Leu Gly Gly Ser Asp Asp Thr
            100                 105                 110

Val Asp Ala Tyr Glu Ser Gly Glu Leu Ala Lys Leu Leu Gly Val Ser
        115                 120                 125

Gly Asn Lys Glu Ala Glu Leu
        130                 135

<210> SEQ ID NO 33
<211> LENGTH: 540
```

```
<212> TYPE: DNA
<213> ORGANISM: Arabidopsis thaliana
<220> FEATURE:
<221> NAME/KEY: CDS
<222> LOCATION: (1)..(537)
<223> OTHER INFORMATION: AtQ9SK75

<400> SEQUENCE: 33 atg gta gcc gca aca gta aac ctc gcg aac atg aca tgg acg tcg tta    48
Met Val Ala Ala Thr Val Asn Leu Ala Asn Met Thr Trp Thr Ser Leu
1               5                   10                  15 aat tca aat cca gca atc tct ttc tcc atg tta agc gga atc aga aac    96
Asn Ser Asn Pro Ala Ile Ser Phe Ser Met Leu Ser Gly Ile Arg Asn
            20                  25                  30 ttg ggc atg tta cct ttc agg aga tgt cta aag ccg aca gtt atc gga    144
Leu Gly Met Leu Pro Phe Arg Arg Cys Leu Lys Pro Thr Val Ile Gly
        35                  40                  45 atc gcg tcg tgg cca cca ctc cgt tgt tct tct gtt aag gct atg tct    192
Ile Ala Ser Trp Pro Pro Leu Arg Cys Ser Ser Val Lys Ala Met Ser
    50                  55                  60 tca tca tcg tct tcg tct gga tcg aca ttg gag gag act gtt aaa acg    240
Ser Ser Ser Ser Ser Ser Gly Ser Thr Leu Glu Glu Thr Val Lys Thr
65                  70                  75                  80 act gtg gca gag aac cct gtc gtt gtt tac tcc aaa acc tgg tgc tca    288
Thr Val Ala Glu Asn Pro Val Val Val Tyr Ser Lys Thr Trp Cys Ser
                85                  90                  95 tac tcg tct caa gtg aag tcc ttg ttc aag agt ctt caa gtt gag cca    336
Tyr Ser Ser Gln Val Lys Ser Leu Phe Lys Ser Leu Gln Val Glu Pro
            100                 105                 110 ctg gtt gtt gaa ttg gat caa ctt ggt tca gaa ggg tcg cag ctg cag    384
Leu Val Val Glu Leu Asp Gln Leu Gly Ser Glu Gly Ser Gln Leu Gln
        115                 120                 125 aat gtg ttg gag aaa att act gga caa tac act gtt ccc aat gtt ttc    432
Asn Val Leu Glu Lys Ile Thr Gly Gln Tyr Thr Val Pro Asn Val Phe
    130                 135                 140 atc gga ggc aag cac att ggt ggc tgc tca gat aca ttg cag ctg cac    480
Ile Gly Gly Lys His Ile Gly Gly Cys Ser Asp Thr Leu Gln Leu His
145                 150                 155                 160 aat aaa gga gag ctg gaa gca att tta gct gaa gcc aat gga aaa aac    528
Asn Lys Gly Glu Leu Glu Ala Ile Leu Ala Glu Ala Asn Gly Lys Asn
                165                 170                 175 ggt cag acc tag                                                    540
Gly Gln Thr <210> SEQ ID NO 34
<211> LENGTH: 179
<212> TYPE: PRT
<213> ORGANISM: Arabidopsis thaliana

<400> SEQUENCE: 34

Met Val Ala Ala Thr Val Asn Leu Ala Asn Met Thr Trp Thr Ser Leu
1               5                   10                  15

Asn Ser Asn Pro Ala Ile Ser Phe Ser Met Leu Ser Gly Ile Arg Asn
            20                  25                  30

Leu Gly Met Leu Pro Phe Arg Arg Cys Leu Lys Pro Thr Val Ile Gly
        35                  40                  45

Ile Ala Ser Trp Pro Pro Leu Arg Cys Ser Ser Val Lys Ala Met Ser
    50                  55                  60

Ser Ser Ser Ser Ser Ser Gly Ser Thr Leu Glu Glu Thr Val Lys Thr
65                  70                  75                  80

Thr Val Ala Glu Asn Pro Val Val Val Tyr Ser Lys Thr Trp Cys Ser
```

```
                   85                  90                  95
Tyr Ser Ser Gln Val Lys Ser Leu Phe Lys Ser Leu Gln Val Glu Pro
                100                 105                 110

Leu Val Val Glu Leu Asp Gln Leu Gly Ser Glu Gly Ser Gln Leu Gln
            115                 120                 125

Asn Val Leu Glu Lys Ile Thr Gly Gln Tyr Thr Val Pro Asn Val Phe
        130                 135                 140

Ile Gly Gly Lys His Ile Gly Cys Ser Asp Thr Leu Gln Leu His
145                 150                 155                 160

Asn Lys Gly Glu Leu Glu Ala Ile Leu Ala Glu Ala Asn Gly Lys Asn
                165                 170                 175

Gly Gln Thr

<210> SEQ ID NO 35
<211> LENGTH: 510
<212> TYPE: DNA
<213> ORGANISM: Arabidopsis thaliana
<220> FEATURE:
<221> NAME/KEY: CDS
<222> LOCATION: (1)..(507)
<223> OTHER INFORMATION: AtQ9LW13

<400> SEQUENCE: 35 atg gcg gct tct tta tcg agc aga ctt ata aaa gga atc gct aat ctc        48
Met Ala Ala Ser Leu Ser Ser Arg Leu Ile Lys Gly Ile Ala Asn Leu
1               5                   10                  15 aaa gct gtt cgt tct agc aga ttg acg tct gca tca gtc tac caa aat        96
Lys Ala Val Arg Ser Ser Arg Leu Thr Ser Ala Ser Val Tyr Gln Asn
                20                  25                  30 ggg atg atg aga ttt tcc tca aca gtg cca agt gat tca gat aca cat       144
Gly Met Met Arg Phe Ser Ser Thr Val Pro Ser Asp Ser Asp Thr His
            35                  40                  45 gat gat ttc aag cct aca caa aaa gtc cct ccc gat tct acg gac tca       192
Asp Asp Phe Lys Pro Thr Gln Lys Val Pro Pro Asp Ser Thr Asp Ser
        50                  55                  60 ctt aaa gat atc gtt gag aat gat gtg aag gat aat cct gtt atg atc       240
Leu Lys Asp Ile Val Glu Asn Asp Val Lys Asp Asn Pro Val Met Ile
65                  70                  75                  80 tac atg aaa ggt gtc cct gaa tct cct cag tgt ggg ttt agc tca cta       288
Tyr Met Lys Gly Val Pro Glu Ser Pro Gln Cys Gly Phe Ser Ser Leu
                85                  90                  95 gcc gtc aga gtt ttg cag caa tat aat gtt cct atc agt tct aga aac       336
Ala Val Arg Val Leu Gln Gln Tyr Asn Val Pro Ile Ser Ser Arg Asn
                100                 105                 110 att cta gaa gac caa gag ttg aaa aac gct gtg aaa tcc ttc agc cac       384
Ile Leu Glu Asp Gln Glu Leu Lys Asn Ala Val Lys Ser Phe Ser His
            115                 120                 125 tgg cct acg ttt cca cag atc ttc att aag gga gag ttc att ggc ggc       432
Trp Pro Thr Phe Pro Gln Ile Phe Ile Lys Gly Glu Phe Ile Gly Gly
        130                 135                 140 tca gac atc atc ctt aac atg cac aag gaa ggt gaa ttg gag cag aag       480
Ser Asp Ile Ile Leu Asn Met His Lys Glu Gly Glu Leu Glu Gln Lys
145                 150                 155                 160 ctt aaa gac gtc tcc gga aac caa gat tga                               510
Leu Lys Asp Val Ser Gly Asn Gln Asp
                165

<210> SEQ ID NO 36
<211> LENGTH: 169
<212> TYPE: PRT
<213> ORGANISM: Arabidopsis thaliana
```

<400> SEQUENCE: 36

```
Met Ala Ala Ser Leu Ser Ser Arg Leu Ile Lys Gly Ile Ala Asn Leu
1               5                   10                  15

Lys Ala Val Arg Ser Ser Arg Leu Thr Ser Ala Ser Val Tyr Gln Asn
            20                  25                  30

Gly Met Met Arg Phe Ser Ser Thr Val Pro Ser Asp Ser Asp Thr His
        35                  40                  45

Asp Asp Phe Lys Pro Thr Gln Lys Val Pro Asp Ser Thr Asp Ser
    50                  55                  60

Leu Lys Asp Ile Val Glu Asn Asp Val Lys Asp Asn Pro Val Met Ile
65                  70                  75                  80

Tyr Met Lys Gly Val Pro Glu Ser Pro Gln Cys Gly Phe Ser Ser Leu
                85                  90                  95

Ala Val Arg Val Leu Gln Gln Tyr Asn Val Pro Ile Ser Ser Arg Asn
            100                 105                 110

Ile Leu Glu Asp Gln Glu Leu Lys Asn Ala Val Lys Ser Phe Ser His
        115                 120                 125

Trp Pro Thr Phe Pro Gln Ile Phe Ile Lys Gly Glu Phe Ile Gly Gly
    130                 135                 140

Ser Asp Ile Ile Leu Asn Met His Lys Glu Gly Glu Leu Glu Gln Lys
145                 150                 155                 160

Leu Lys Asp Val Ser Gly Asn Gln Asp
                165
```

<210> SEQ ID NO 37
<211> LENGTH: 522
<212> TYPE: DNA
<213> ORGANISM: Arabidopsis thaliana
<220> FEATURE:
<221> NAME/KEY: CDS
<222> LOCATION: (1)..(519)
<223> OTHER INFORMATION: AtQ9SV38

<400> SEQUENCE: 37

```
atg gct ctc cga tct gtc aaa acg ccg acc ttg ata act tcg gtc gcc     48
Met Ala Leu Arg Ser Val Lys Thr Pro Thr Leu Ile Thr Ser Val Ala
1               5                   10                  15 gtc gtc tcc tcc tcc gtt acc aac aag cct cac tct atc aga ttc tct    96
Val Val Ser Ser Ser Val Thr Asn Lys Pro His Ser Ile Arg Phe Ser
            20                  25                  30 ctt aaa cca acg tcg gca ctc gtc gtc cat aac cat cag cta tcg ttc   144
Leu Lys Pro Thr Ser Ala Leu Val Val His Asn His Gln Leu Ser Phe
        35                  40                  45 tac ggt tcg aat ctc aag ctg aaa cca act aaa ttc cga tgc tca gcg   192
Tyr Gly Ser Asn Leu Lys Leu Lys Pro Thr Lys Phe Arg Cys Ser Ala
    50                  55                  60 tcg gct ctt acg ccg caa ctt aaa gac acg ctg gag aaa ctg gtg aat   240
Ser Ala Leu Thr Pro Gln Leu Lys Asp Thr Leu Glu Lys Leu Val Asn
65                  70                  75                  80 tcg gag aaa gtg gtt ctg ttt atg aaa gga acg aga gac ttc ccg atg   288
Ser Glu Lys Val Val Leu Phe Met Lys Gly Thr Arg Asp Phe Pro Met
                85                  90                  95 tgt gga ttc tcc aac act gtg gtt cag att ttg aag aat ctg aat gtt   336
Cys Gly Phe Ser Asn Thr Val Val Gln Ile Leu Lys Asn Leu Asn Val
            100                 105                 110 cct ttc gaa gat gtg aat att ctg gag aat gag atg ttg agg caa gga   384
Pro Phe Glu Asp Val Asn Ile Leu Glu Asn Glu Met Leu Arg Gln Gly
        115                 120                 125
```

```
ctt aaa gag tat tcg aat tgg ccg acg ttt cct cag ctt tat atc ggc      432
Leu Lys Glu Tyr Ser Asn Trp Pro Thr Phe Pro Gln Leu Tyr Ile Gly
    130                 135                 140 ggt gag ttt ttc ggt ggt tgt gat att act ctt gag gcg ttt aag act      480
Gly Glu Phe Phe Gly Gly Cys Asp Ile Thr Leu Glu Ala Phe Lys Thr
145                 150                 155                 160 gga gaa ttg cag gaa gag gtg gag aaa gct atg tgc tct tga              522
Gly Glu Leu Gln Glu Glu Val Glu Lys Ala Met Cys Ser
                165                 170
```

<210> SEQ ID NO 38
<211> LENGTH: 173
<212> TYPE: PRT
<213> ORGANISM: Arabidopsis thaliana

<400> SEQUENCE: 38

```
Met Ala Leu Arg Ser Val Lys Thr Pro Thr Leu Ile Thr Ser Val Ala
1               5                   10                  15

Val Val Ser Ser Val Thr Asn Lys Pro His Ser Ile Arg Phe Ser
                20                  25                  30

Leu Lys Pro Thr Ser Ala Leu Val Val His Asn His Gln Leu Ser Phe
                35                  40                  45

Tyr Gly Ser Asn Leu Lys Leu Lys Pro Thr Lys Phe Arg Cys Ser Ala
    50                  55                  60

Ser Ala Leu Thr Pro Gln Leu Lys Asp Thr Leu Glu Lys Leu Val Asn
65                  70                  75                  80

Ser Glu Lys Val Val Leu Phe Met Lys Gly Thr Arg Asp Phe Pro Met
                85                  90                  95

Cys Gly Phe Ser Asn Thr Val Val Gln Ile Leu Lys Asn Leu Asn Val
                100                 105                 110

Pro Phe Glu Asp Val Asn Ile Leu Glu Asn Glu Met Leu Arg Gln Gly
            115                 120                 125

Leu Lys Glu Tyr Ser Asn Trp Pro Thr Phe Pro Gln Leu Tyr Ile Gly
    130                 135                 140

Gly Glu Phe Phe Gly Gly Cys Asp Ile Thr Leu Glu Ala Phe Lys Thr
145                 150                 155                 160

Gly Glu Leu Gln Glu Glu Val Glu Lys Ala Met Cys Ser
                165                 170
```

<210> SEQ ID NO 39
<211> LENGTH: 882
<212> TYPE: DNA
<213> ORGANISM: Arabidopsis thaliana
<220> FEATURE:
<221> NAME/KEY: CDS
<222> LOCATION: (1)..(879)
<223> OTHER INFORMATION: AT080451

<400> SEQUENCE: 39

```
atg gct gca atc acc att tct tcc tcc ttg cac gcc tca gcc tct ccg      48
Met Ala Ala Ile Thr Ile Ser Ser Ser Leu His Ala Ser Ala Ser Pro
1               5                   10                  15 cgt gtt gtt cgt cca cat gtt tct cga aat acc cct gtg atc acc ctc      96
Arg Val Val Arg Pro His Val Ser Arg Asn Thr Pro Val Ile Thr Leu
                20                  25                  30 tat tca cgc ttc aca cca tcc ttc tcc ttc cca tct ctc tcc ttc aca      144
Tyr Ser Arg Phe Thr Pro Ser Phe Ser Phe Pro Ser Leu Ser Phe Thr
                35                  40                  45 ctc cgt gac aca gct ccg tct cgt cgt cgt tcc ttc ttt atc gcc tcc      192
Leu Arg Asp Thr Ala Pro Ser Arg Arg Arg Ser Phe Phe Ile Ala Ser
    50                  55                  60
```

```
gcc gtc aaa tct cta acg gag acg gag ctg ctt cca atc aca gag gct   240
Ala Val Lys Ser Leu Thr Glu Thr Glu Leu Leu Pro Ile Thr Glu Ala
 65              70                  75                  80 gat tca atc ccg tcc gct tcc ggt gta tac gct gta tac gat aag agc   288
Asp Ser Ile Pro Ser Ala Ser Gly Val Tyr Ala Val Tyr Asp Lys Ser
                 85                  90                  95 gac gag ctt cag ttc gtc gga att tct cgg aac atc gct gcg agt gtc   336
Asp Glu Leu Gln Phe Val Gly Ile Ser Arg Asn Ile Ala Ala Ser Val
            100                 105                 110 tct gct cat ctc aaa tct gtg ccg gag ctt tgt ggc tcc gtt aag gtt   384
Ser Ala His Leu Lys Ser Val Pro Glu Leu Cys Gly Ser Val Lys Val
        115                 120                 125 gga ata gta gaa gaa cca gat aaa gca gtt tta aca caa gca tgg aaa   432
Gly Ile Val Glu Glu Pro Asp Lys Ala Val Leu Thr Gln Ala Trp Lys
130                 135                 140 tta tgg ata gaa gaa cat ata aaa gta act gga aaa gtt ccg ccg ggg   480
Leu Trp Ile Glu Glu His Ile Lys Val Thr Gly Lys Val Pro Pro Gly
145                 150                 155                 160 aat aag tca ggg aac aac aca ttt gtc aaa caa act ccg agg aag aaa   528
Asn Lys Ser Gly Asn Asn Thr Phe Val Lys Gln Thr Pro Arg Lys Lys
                165                 170                 175 tcc gat atc cgt ctc act cca ggt cgc cat gtt gag ctc acg gtt cct   576
Ser Asp Ile Arg Leu Thr Pro Gly Arg His Val Glu Leu Thr Val Pro
            180                 185                 190 ttg gag gaa ctg att gac cgt tta gtg aaa gag agc aaa gtg gta gct   624
Leu Glu Glu Leu Ile Asp Arg Leu Val Lys Glu Ser Lys Val Val Ala
        195                 200                 205 ttc ata aaa gga tca agg agt gct cct caa tgt gga ttc tca cag aga   672
Phe Ile Lys Gly Ser Arg Ser Ala Pro Gln Cys Gly Phe Ser Gln Arg
210                 215                 220 gtt gtt ggg att ctt gaa agc caa gga gtt gat tat gaa act gtt gat   720
Val Val Gly Ile Leu Glu Ser Gln Gly Val Asp Tyr Glu Thr Val Asp
225                 230                 235                 240 gtt ctt gac gat gag tat aat cat ggg cta agg gag acg ctt aag aac   768
Val Leu Asp Asp Glu Tyr Asn His Gly Leu Arg Glu Thr Leu Lys Asn
                245                 250                 255 tac agc aat tgg cca acg ttt cca cag ata ttt gtg aaa gga gaa ctt   816
Tyr Ser Asn Trp Pro Thr Phe Pro Gln Ile Phe Val Lys Gly Glu Leu
            260                 265                 270 gta gga gga tgt gat att ttg acc tca atg tat gaa aat ggt gaa ctt   864
Val Gly Gly Cys Asp Ile Leu Thr Ser Met Tyr Glu Asn Gly Glu Leu
        275                 280                 285 gcc aat atc ttg aac tag                                           882
Ala Asn Ile Leu Asn
            290

<210> SEQ ID NO 40
<211> LENGTH: 293
<212> TYPE: PRT
<213> ORGANISM: Arabidopsis thaliana

<400> SEQUENCE: 40

Met Ala Ala Ile Thr Ile Ser Ser Ser Leu His Ala Ser Ala Ser Pro
1               5                   10                  15

Arg Val Val Arg Pro His Val Ser Arg Asn Thr Pro Val Ile Thr Leu
            20                  25                  30

Tyr Ser Arg Phe Thr Pro Ser Phe Ser Phe Pro Ser Leu Ser Phe Thr
        35                  40                  45

Leu Arg Asp Thr Ala Pro Ser Arg Arg Ser Phe Phe Ile Ala Ser
    50                  55                  60
```

```
Ala Val Lys Ser Leu Thr Glu Thr Glu Leu Leu Pro Ile Thr Glu Ala
 65                  70                  75                  80

Asp Ser Ile Pro Ser Ala Ser Gly Val Tyr Ala Val Tyr Asp Lys Ser
                 85                  90                  95

Asp Glu Leu Gln Phe Val Gly Ile Ser Arg Asn Ile Ala Ala Ser Val
            100                 105                 110

Ser Ala His Leu Lys Ser Val Pro Glu Leu Cys Gly Ser Val Lys Val
        115                 120                 125

Gly Ile Val Glu Glu Pro Asp Lys Ala Val Leu Thr Gln Ala Trp Lys
    130                 135                 140

Leu Trp Ile Glu Glu His Ile Lys Val Thr Gly Lys Val Pro Pro Gly
145                 150                 155                 160

Asn Lys Ser Gly Asn Asn Thr Phe Val Lys Gln Thr Pro Arg Lys Lys
                165                 170                 175

Ser Asp Ile Arg Leu Thr Pro Gly Arg His Val Glu Leu Thr Val Pro
            180                 185                 190

Leu Glu Glu Leu Ile Asp Arg Leu Val Lys Glu Ser Lys Val Val Ala
        195                 200                 205

Phe Ile Lys Gly Ser Arg Ser Ala Pro Gln Cys Gly Phe Ser Gln Arg
    210                 215                 220

Val Val Gly Ile Leu Glu Ser Gln Gly Val Asp Tyr Glu Thr Val Asp
225                 230                 235                 240

Val Leu Asp Asp Glu Tyr Asn His Gly Leu Arg Glu Thr Leu Lys Asn
                245                 250                 255

Tyr Ser Asn Trp Pro Thr Phe Pro Gln Ile Phe Val Lys Gly Glu Leu
            260                 265                 270

Val Gly Gly Cys Asp Ile Leu Thr Ser Met Tyr Glu Asn Gly Glu Leu
        275                 280                 285

Ala Asn Ile Leu Asn
    290

<210> SEQ ID NO 41
<211> LENGTH: 483
<212> TYPE: DNA
<213> ORGANISM: Arabidopsis thaliana
<220> FEATURE:
<221> NAME/KEY: CDS
<222> LOCATION: (1)..(480)
<223> OTHER INFORMATION: AT065541

<400> SEQUENCE: 41 atg agt ggt act gtg aag gat atc gtt tca aag gag gag ctt gat aac      48
Met Ser Gly Thr Val Lys Asp Ile Val Ser Lys Glu Glu Leu Asp Asn
1               5                  10                  15 ttg cgc cac agc gga gca cca ctc gtg ctt cac ttc tgg gct tct tgg      96
Leu Arg His Ser Gly Ala Pro Leu Val Leu His Phe Trp Ala Ser Trp
            20                  25                  30 tgt gac gct tcg aag cag atg gat caa gtt ttc tct cat ctc gct act     144
Cys Asp Ala Ser Lys Gln Met Asp Gln Val Phe Ser His Leu Ala Thr
        35                  40                  45 gat ttc cct cgt gct cac ttc ttt agg gta gaa gct gag gaa cat cct     192
Asp Phe Pro Arg Ala His Phe Phe Arg Val Glu Ala Glu Glu His Pro
    50                  55                  60 gag ata tct gag gct tat tct gtt gct ctt gtg ccg tat ttc gtc ttc     240
Glu Ile Ser Glu Ala Tyr Ser Val Ala Leu Val Pro Tyr Phe Val Phe
65                  70                  75                  80 ttc aag gat ggc aaa act gtg gat aca ctt gaa ggg gca gat cca tca     288
Phe Lys Asp Gly Lys Thr Val Asp Thr Leu Glu Gly Ala Asp Pro Ser
```

```
agt tta gct aat aaa gtt ggc aaa gtt gct ggt tct att act cct gca    336
Ser Leu Ala Asn Lys Val Gly Lys Val Ala Gly Ser Ile Thr Pro Ala
            100                 105                 110 agc tta ggg ttg gct gca ggg cca acg att ctt gaa act gtt aag aag    384
Ser Leu Gly Leu Ala Ala Gly Pro Thr Ile Leu Glu Thr Val Lys Lys
        115                 120                 125 aat gcg aaa gct tct gga caa gac cga gct cag cct gta tct acc gct    432
Asn Ala Lys Ala Ser Gly Gln Asp Arg Ala Gln Pro Val Ser Thr Ala
    130                 135                 140 gat gct ctc aag aat cgt ttg gaa aaa ctc acc ctg tta tgt tat tca    480
Asp Ala Leu Lys Asn Arg Leu Glu Lys Leu Thr Leu Leu Cys Tyr Ser
145                 150                 155                 160 tga                                                                483
```

<210> SEQ ID NO 42
<211> LENGTH: 160
<212> TYPE: PRT
<213> ORGANISM: Arabidopsis thaliana

<400> SEQUENCE: 42

```
Met Ser Gly Thr Val Lys Asp Ile Val Ser Lys Glu Glu Leu Asp Asn
1               5                   10                  15

Leu Arg His Ser Gly Ala Pro Leu Val Leu His Phe Trp Ala Ser Trp
            20                  25                  30

Cys Asp Ala Ser Lys Gln Met Asp Gln Val Phe Ser His Leu Ala Thr
        35                  40                  45

Asp Phe Pro Arg Ala His Phe Phe Arg Val Glu Ala Glu His Pro
    50                  55                  60

Glu Ile Ser Glu Ala Tyr Ser Val Ala Leu Val Pro Tyr Phe Val Phe
65                  70                  75                  80

Phe Lys Asp Gly Lys Thr Val Asp Thr Leu Glu Gly Ala Asp Pro Ser
                85                  90                  95

Ser Leu Ala Asn Lys Val Gly Lys Val Ala Gly Ser Ile Thr Pro Ala
            100                 105                 110

Ser Leu Gly Leu Ala Ala Gly Pro Thr Ile Leu Glu Thr Val Lys Lys
        115                 120                 125

Asn Ala Lys Ala Ser Gly Gln Asp Arg Ala Gln Pro Val Ser Thr Ala
    130                 135                 140

Asp Ala Leu Lys Asn Arg Leu Glu Lys Leu Thr Leu Leu Cys Tyr Ser
145                 150                 155                 160
```

<210> SEQ ID NO 43
<211> LENGTH: 1467
<212> TYPE: DNA
<213> ORGANISM: Arabidopsis thaliana
<220> FEATURE:
<221> NAME/KEY: CDS
<222> LOCATION: (1)..(1464)
<223> OTHER INFORMATION: AtQ9ZPH2

<400> SEQUENCE: 43

```
atg agc ggt acg gtg aag gat atc gtt tca aag gcg gag ctt gat aac    48
Met Ser Gly Thr Val Lys Asp Ile Val Ser Lys Ala Glu Leu Asp Asn
1               5                   10                  15 ttg cgc cag agc ggc gca cca gtc gtg ctt cac ttc tgg gct tct tgg    96
Leu Arg Gln Ser Gly Ala Pro Val Val Leu His Phe Trp Ala Ser Trp
            20                  25                  30 tgt gat gct tcg aag cag atg gat caa gtt ttc tct cat ctc gct act   144
Cys Asp Ala Ser Lys Gln Met Asp Gln Val Phe Ser His Leu Ala Thr
        35                  40                  45
```

-continued

```
                35                   40                   45
gat ttc cct cgt gct cac ttc ttt agg gtt gaa gct gag gaa cat cct    192
Asp Phe Pro Arg Ala His Phe Phe Arg Val Glu Ala Glu Glu His Pro
 50                  55                   60 gag ata tct gag gct tac tct gtt gct gct gtg cct tat ttc gtc ttc    240
Glu Ile Ser Glu Ala Tyr Ser Val Ala Ala Val Pro Tyr Phe Val Phe
 65                  70                   75                   80 ttc aag gat ggt aaa act gtg gat aca ctt gag ggt gca gat cca tca    288
Phe Lys Asp Gly Lys Thr Val Asp Thr Leu Glu Gly Ala Asp Pro Ser
                     85                   90                   95 agt tta gct aat aag gtt ggc aaa gtt gct ggt tct agt act tct gcg    336
Ser Leu Ala Asn Lys Val Gly Lys Val Ala Gly Ser Ser Thr Ser Ala
                    100                  105                  110 gag cct gct gct cct gca agc tta ggg ttg gct gct ggg cca acg att    384
Glu Pro Ala Ala Pro Ala Ser Leu Gly Leu Ala Ala Gly Pro Thr Ile
                115                  120                  125 ctt gaa act gtg aag gag aat gcg aaa gct tct tta caa gac cga gct    432
Leu Glu Thr Val Lys Glu Asn Ala Lys Ala Ser Leu Gln Asp Arg Ala
130                  135                  140 cag cct gta tct acc gcc gat gct ctc aag agc cgt ttg gaa aag ctc    480
Gln Pro Val Ser Thr Ala Asp Ala Leu Lys Ser Arg Leu Glu Lys Leu
145                  150                  155                  160 act aat tct cac cct gtc atg tta ttc atg aaa ggt att cct gaa gag    528
Thr Asn Ser His Pro Val Met Leu Phe Met Lys Gly Ile Pro Glu Glu
                    165                  170                  175 cct agg tgt ggg ttt agc agg aaa gta gtt gac att ttg aaa gag gtt    576
Pro Arg Cys Gly Phe Ser Arg Lys Val Val Asp Ile Leu Lys Glu Val
                180                  185                  190 aac gtt gat ttt gga agt ttt gac ata cta tcg gat aac gaa gtg cga    624
Asn Val Asp Phe Gly Ser Phe Asp Ile Leu Ser Asp Asn Glu Val Arg
            195                  200                  205 gag ggt ttg aag aaa ttc tct aac tgg cca acg ttt cct cag ctg tac    672
Glu Gly Leu Lys Lys Phe Ser Asn Trp Pro Thr Phe Pro Gln Leu Tyr
210                  215                  220 tgc aac gga gag ctt ctt ggt gga gct gat atc gca ata gcg atg cac    720
Cys Asn Gly Glu Leu Leu Gly Gly Ala Asp Ile Ala Ile Ala Met His
225                  230                  235                  240 gag agc ggt gaa cta aaa gat gct ttc aaa gat ctt ggg atc acg aca    768
Glu Ser Gly Glu Leu Lys Asp Ala Phe Lys Asp Leu Gly Ile Thr Thr
                245                  250                  255 gtt ggt tca aaa gaa agt cag gat gaa gct gga aaa gga gga ggg gtt    816
Val Gly Ser Lys Glu Ser Gln Asp Glu Ala Gly Lys Gly Gly Gly Val
                260                  265                  270 agt tca gga aac aca ggc tta agt gag acc ctc cga gct cgg ctc gaa    864
Ser Ser Gly Asn Thr Gly Leu Ser Glu Thr Leu Arg Ala Arg Leu Glu
            275                  280                  285 ggt ctg gtc aat tcc aaa cca gtt atg ctg ttc atg aaa gga aga cca    912
Gly Leu Val Asn Ser Lys Pro Val Met Leu Phe Met Lys Gly Arg Pro
290                  295                  300 gaa gaa cca aag tgt ggg ttc agt ggg aaa gtg gtt gaa atc ctc aac    960
Glu Glu Pro Lys Cys Gly Phe Ser Gly Lys Val Val Glu Ile Leu Asn
305                  310                  315                  320 caa gaa aaa atc gag ttt ggg agt ttc gat atc ctc tta gat gac gaa   1008
Gln Glu Lys Ile Glu Phe Gly Ser Phe Asp Ile Leu Leu Asp Asp Glu
                325                  330                  335 gtt cgc caa ggc ctt aaa gtg tat tca aac tgg tca agc tat cct cag   1056
Val Arg Gln Gly Leu Lys Val Tyr Ser Asn Trp Ser Ser Tyr Pro Gln
                340                  345                  350 ctt tac gtg aaa ggc gag ctt atg ggt gga tca gac att gtc ttg gag   1104
Leu Tyr Val Lys Gly Glu Leu Met Gly Gly Ser Asp Ile Val Leu Glu
```

```
                          355                 360                 365
atg caa aag agc ggt gag ctg aaa aag gtc ttg acc gag aaa ggg atc          1152
Met Gln Lys Ser Gly Glu Leu Lys Lys Val Leu Thr Glu Lys Gly Ile
    370                 375                 380 act gga gaa cag agt ctt gaa gat aga ttg aag gca ctg atc aat tcc          1200
Thr Gly Glu Gln Ser Leu Glu Asp Arg Leu Lys Ala Leu Ile Asn Ser
385                 390                 395                 400 tcg gaa gta atg cta ttc atg aaa ggt tca cca gat gaa ccg aaa tgc          1248
Ser Glu Val Met Leu Phe Met Lys Gly Ser Pro Asp Glu Pro Lys Cys
                405                 410                 415 gga ttt agc tcc aaa gtt gtg aaa gca ttg aga gga gaa aac gtg agt          1296
Gly Phe Ser Ser Lys Val Val Lys Ala Leu Arg Gly Glu Asn Val Ser
            420                 425                 430 ttc gga tcg ttt gat atc ttg act gat gaa gaa gta agg caa ggg att          1344
Phe Gly Ser Phe Asp Ile Leu Thr Asp Glu Glu Val Arg Gln Gly Ile
        435                 440                 445 aag aat ttc tca aac tgg cca act ttt cct cag cta tac tac aaa ggt          1392
Lys Asn Phe Ser Asn Trp Pro Thr Phe Pro Gln Leu Tyr Tyr Lys Gly
    450                 455                 460 gag tta att gga gga tgt gat atc att atg gag cta agt gag agt ggt          1440
Glu Leu Ile Gly Gly Cys Asp Ile Ile Met Glu Leu Ser Glu Ser Gly
465                 470                 475                 480 gat ctc aaa gca act cta tcc gag taa                                      1467
Asp Leu Lys Ala Thr Leu Ser Glu
                485

<210> SEQ ID NO 44
<211> LENGTH: 488
<212> TYPE: PRT
<213> ORGANISM: Arabidopsis thaliana

<400> SEQUENCE: 44

Met Ser Gly Thr Val Lys Asp Ile Val Ser Lys Ala Glu Leu Asp Asn
1               5                   10                  15

Leu Arg Gln Ser Gly Ala Pro Val Val Leu His Phe Trp Ala Ser Trp
            20                  25                  30

Cys Asp Ala Ser Lys Gln Met Asp Gln Val Phe Ser His Leu Ala Thr
        35                  40                  45

Asp Phe Pro Arg Ala His Phe Phe Arg Val Glu Ala Glu His Pro
    50                  55                  60

Glu Ile Ser Glu Ala Tyr Ser Val Ala Val Pro Tyr Phe Val Phe
65                  70                  75                  80

Phe Lys Asp Gly Lys Thr Val Asp Thr Leu Glu Gly Ala Asp Pro Ser
                85                  90                  95

Ser Leu Ala Asn Lys Val Gly Lys Val Ala Gly Ser Thr Ser Ala
                100                 105                 110

Glu Pro Ala Ala Pro Ala Ser Leu Gly Leu Ala Gly Pro Thr Ile
            115                 120                 125

Leu Glu Thr Val Lys Glu Asn Ala Lys Ala Ser Leu Gln Asp Arg Ala
        130                 135                 140

Gln Pro Val Ser Thr Ala Asp Ala Leu Lys Ser Arg Leu Glu Lys Leu
145                 150                 155                 160

Thr Asn Ser His Pro Val Met Leu Phe Met Lys Gly Ile Pro Glu Glu
                165                 170                 175

Pro Arg Cys Gly Phe Ser Arg Lys Val Val Asp Ile Leu Lys Glu Val
            180                 185                 190

Asn Val Asp Phe Gly Ser Phe Asp Ile Leu Ser Asp Asn Glu Val Arg
        195                 200                 205
```

```
Glu Gly Leu Lys Lys Phe Ser Asn Trp Pro Thr Phe Pro Gln Leu Tyr
    210                 215                 220
Cys Asn Gly Glu Leu Leu Gly Gly Ala Asp Ile Ala Ile Ala Met His
225                 230                 235                 240
Glu Ser Gly Glu Leu Lys Asp Ala Phe Lys Asp Leu Gly Ile Thr Thr
                245                 250                 255
Val Gly Ser Lys Glu Ser Gln Asp Glu Ala Gly Lys Gly Gly Val
            260                 265                 270
Ser Ser Gly Asn Thr Gly Leu Ser Glu Thr Leu Arg Ala Arg Leu Glu
        275                 280                 285
Gly Leu Val Asn Ser Lys Pro Val Met Leu Phe Met Lys Gly Arg Pro
    290                 295                 300
Glu Glu Pro Lys Cys Gly Phe Ser Gly Lys Val Val Glu Ile Leu Asn
305                 310                 315                 320
Gln Glu Lys Ile Glu Phe Gly Ser Phe Asp Ile Leu Leu Asp Asp Glu
                325                 330                 335
Val Arg Gln Gly Leu Lys Val Tyr Ser Asn Trp Ser Ser Tyr Pro Gln
            340                 345                 350
Leu Tyr Val Lys Gly Glu Leu Met Gly Gly Ser Asp Ile Val Leu Glu
        355                 360                 365
Met Gln Lys Ser Gly Glu Leu Lys Lys Val Leu Thr Glu Lys Gly Ile
    370                 375                 380
Thr Gly Glu Gln Ser Leu Glu Asp Arg Leu Lys Ala Leu Ile Asn Ser
385                 390                 395                 400
Ser Glu Val Met Leu Phe Met Lys Gly Ser Pro Asp Glu Pro Lys Cys
                405                 410                 415
Gly Phe Ser Ser Lys Val Val Lys Ala Leu Arg Gly Glu Asn Val Ser
            420                 425                 430
Phe Gly Ser Phe Asp Ile Leu Thr Asp Glu Glu Val Arg Gln Gly Ile
        435                 440                 445
Lys Asn Phe Ser Asn Trp Pro Thr Phe Pro Gln Leu Tyr Tyr Lys Gly
    450                 455                 460
Glu Leu Ile Gly Gly Cys Asp Ile Ile Met Glu Leu Ser Glu Ser Gly
465                 470                 475                 480
Asp Leu Lys Ala Thr Leu Ser Glu
                485

<210> SEQ ID NO 45
<211> LENGTH: 628
<212> TYPE: DNA
<213> ORGANISM: Oryza sativa
<220> FEATURE:
<221> NAME/KEY: CDS
<222> LOCATION: (100)..(507)
<223> OTHER INFORMATION: OZ1116C12744

<400> SEQUENCE: 45
ccgggtcgac gatttcgtct tccccaactc tctccgcctc ttcctcctcc gcctccggtg      60
atccggtctc gctatctctc ttccgcatct cgggacgcg atg gcg gcg ctg ctg       114
                                             Met Ala Ala Leu Leu
                                               1               5 ggc cgg agg ttc ggg atg gcg gcg gcg ctc atc gcc ctc gcg gcg          162
Gly Arg Arg Phe Gly Met Ala Ala Ala Leu Ile Ala Leu Ala Ala
             10                  15                  20 ctc gga tcc gcc gcc tcg ggg acg gcg tcc aag tcg tcc ttc gtg aaa     210
Leu Gly Ser Ala Ala Ser Gly Thr Ala Ser Lys Ser Ser Phe Val Lys
         25                  30                  35
```

| | | | | | | | | | | | | | | | |
|---|---|---|---|---|---|---|---|---|---|---|---|---|---|---|---|
| tcc | acc | gtc | aaa | gcc | cac | gac | gtc | gtc | ata | ttc | tcc | aag | tca | tac | tgc | 258
| Ser | Thr | Val | Lys | Ala | His | Asp | Val | Val | Ile | Phe | Ser | Lys | Ser | Tyr | Cys |
| | | 40 | | | | 45 | | | | | 50 | | | | |

```
tcc acc gtc aaa gcc cac gac gtc gtc ata ttc tcc aag tca tac tgc    258
Ser Thr Val Lys Ala His Asp Val Val Ile Phe Ser Lys Ser Tyr Cys
         40                  45                  50 ccg tac tgt aga aga gcc aaa gct gtg ttc aag gaa ctt gaa ctg aag    306
Pro Tyr Cys Arg Arg Ala Lys Ala Val Phe Lys Glu Leu Glu Leu Lys
 55                  60                  65 aag gag ccg tat gtt gtg gag ctt gat caa cga gag gat ggt tgg gag    354
Lys Glu Pro Tyr Val Val Glu Leu Asp Gln Arg Glu Asp Gly Trp Glu
 70              75                  80                      85 att cag gat gcc tta tct gac atg gtt ggc agg cga act gtt cct caa    402
Ile Gln Asp Ala Leu Ser Asp Met Val Gly Arg Arg Thr Val Pro Gln
             90                  95                 100 gtt ttt gtc cat ggg aag cac ctg ggt ggc tct gat gat act gtt gaa    450
Val Phe Val His Gly Lys His Leu Gly Gly Ser Asp Asp Thr Val Glu
                105                 110                 115 gca tat gag agt ggc aag cta gcc aaa ctt ttg aac att gat gtc aaa    498
Ala Tyr Glu Ser Gly Lys Leu Ala Lys Leu Leu Asn Ile Asp Val Lys
            120                 125                 130 gaa gat ctt tgagtagtaa tagtttagca tcaatggcag gcctctttca            547
Glu Asp Leu
    135 tttccataga acatacccaa atactatgca actatgaatt cttcatagaa tttggctgtg  607 aatgtcctct ttagccccctt t                                           628

<210> SEQ ID NO 46
<211> LENGTH: 136
<212> TYPE: PRT
<213> ORGANISM: Oryza sativa

<400> SEQUENCE: 46

Met Ala Ala Leu Leu Gly Arg Arg Phe Gly Met Ala Ala Ala Ala Leu
 1               5                  10                  15

Ile Ala Leu Ala Ala Leu Gly Ser Ala Ala Ser Gly Thr Ala Ser Lys
            20                  25                  30

Ser Ser Phe Val Lys Ser Thr Val Lys Ala His Asp Val Val Ile Phe
         35                  40                  45

Ser Lys Ser Tyr Cys Pro Tyr Cys Arg Arg Ala Lys Ala Val Phe Lys
 50                  55                  60

Glu Leu Glu Leu Lys Lys Glu Pro Tyr Val Val Glu Leu Asp Gln Arg
 65                  70                  75                  80

Glu Asp Gly Trp Glu Ile Gln Asp Ala Leu Ser Asp Met Val Gly Arg
                 85                  90                  95

Arg Thr Val Pro Gln Val Phe Val His Gly Lys His Leu Gly Gly Ser
            100                 105                 110

Asp Asp Thr Val Glu Ala Tyr Glu Ser Gly Lys Leu Ala Lys Leu Leu
        115                 120                 125

Asn Ile Asp Val Lys Glu Asp Leu
    130                 135

<210> SEQ ID NO 47
<211> LENGTH: 733
<212> TYPE: DNA
<213> ORGANISM: Oryza sativa
<220> FEATURE:
<221> NAME/KEY: CDS
<222> LOCATION: (86)..(466)
<223> OTHER INFORMATION: OZ1116C2194

<400> SEQUENCE: 47
```

```
ccagcaaccg ccccccgccg ctctgccact tcccacccac cccactaatc cactataaat      60
acgcgagcga cgtcacaccg cagag atg gga atc gcc tcc tcc tcc tcc tcg      112
                            Met Gly Ile Ala Ser Ser Ser Ser Ser
                            1               5 acc ccg gaa tcc agg aag atg gcg ctc gcc aag gcc aag gag acc gtc      160
Thr Pro Glu Ser Arg Lys Met Ala Leu Ala Lys Ala Lys Glu Thr Val
10                  15                  20                  25 gcc tcc gct ccc gtc gtc gtc tac agc aag tct tac tgt cct ttt tgc      208
Ala Ser Ala Pro Val Val Val Tyr Ser Lys Ser Tyr Cys Pro Phe Cys
                30                  35                  40 gtc cgt gtg aag aag ttg ttc gag cag ctt gga gca act ttc aag gcc      256
Val Arg Val Lys Lys Leu Phe Glu Gln Leu Gly Ala Thr Phe Lys Ala
            45                  50                  55 att gag ttg gat ggg gag agt gat gga tct gag ctg cag tcg gca ctt      304
Ile Glu Leu Asp Gly Glu Ser Asp Gly Ser Glu Leu Gln Ser Ala Leu
        60                  65                  70 gct gaa tgg act gga caa agg act gtt cca aat gtc ttc atc aat ggg      352
Ala Glu Trp Thr Gly Gln Arg Thr Val Pro Asn Val Phe Ile Asn Gly
    75                  80                  85 aag cat att ggt ggc tgt gat gat act ttg gca ttg aac aat gaa ggg      400
Lys His Ile Gly Gly Cys Asp Asp Thr Leu Ala Leu Asn Asn Glu Gly
90                  95                  100                 105 aag ctg gtg cct ctg ctg acc gag gct gga gca att gcc agt tct gca      448
Lys Leu Val Pro Leu Leu Thr Glu Ala Gly Ala Ile Ala Ser Ser Ala
                110                 115                 120 aag acg aca atc acc gca tagttcttcg tgggacactg ggactagcct              496
Lys Thr Thr Ile Thr Ala
                125 tcgttgacct ctttatactg catccattct attagataat aaaggtggat gtttgtttgg     556 caagaccatt acttgttgcc gtctagtatc gtgtgatagc tatcctgtgc ccgtgtgaaa     616 ctccttggac atcaataata tcgtctttgt gatagcagtt cgctgaaaaa aaaaaaaaa      676 aaaaaaaaaa aaaaaaaaaa aaaaaaaaaa aaaaaaaaaa aaaaaaaaaa aaaaaaa        733
```

<210> SEQ ID NO 48
<211> LENGTH: 127
<212> TYPE: PRT
<213> ORGANISM: Oryza sativa

<400> SEQUENCE: 48

Met Gly Ile Ala Ser Ser Ser Ser Ser Thr Pro Glu Ser Arg Lys Met
1               5                   10                  15

Ala Leu Ala Lys Ala Lys Glu Thr Val Ala Ser Ala Pro Val Val Val
            20                  25                  30

Tyr Ser Lys Ser Tyr Cys Pro Phe Cys Val Arg Val Lys Lys Leu Phe
        35                  40                  45

Glu Gln Leu Gly Ala Thr Phe Lys Ala Ile Glu Leu Asp Gly Glu Ser
    50                  55                  60

Asp Gly Ser Glu Leu Gln Ser Ala Leu Ala Glu Trp Thr Gly Gln Arg
65                  70                  75                  80

Thr Val Pro Asn Val Phe Ile Asn Gly Lys His Ile Gly Gly Cys Asp
                85                  90                  95

Asp Thr Leu Ala Leu Asn Asn Glu Gly Lys Leu Val Pro Leu Leu Thr
            100                 105                 110

Glu Ala Gly Ala Ile Ala Ser Ser Ala Lys Thr Thr Ile Thr Ala
        115                 120                 125

<210> SEQ ID NO 49

```
<211> LENGTH: 754
<212> TYPE: DNA
<213> ORGANISM: Oryza sativa
<220> FEATURE:
<221> NAME/KEY: CDS
<222> LOCATION: (92)..(586)
<223> OTHER INFORMATION: OZ1116C26232

<400> SEQUENCE: 49
accgaccgga gccggagccg cagccgaaga ccaaacacct atcgatccat ccatccgccg       60
ccggcgatcc ctcctatccc ctccatcacc a atg ccg ccg cgg agc ctc acc        112
                                   Met Pro Pro Arg Ser Leu Thr
                                   1               5 ctc tcc cgc ctt ccc gtg gcc gcc ctt ggc ctc ccc ttc tct tct tgc       160
Leu Ser Arg Leu Pro Val Ala Ala Leu Gly Leu Pro Phe Ser Ser Cys
        10                  15                  20 tcc ccg cct cct cct cgc ctt cgc ttc ccc ttc gcc gca cgc cgc gcc       208
Ser Pro Pro Pro Pro Arg Leu Arg Phe Pro Phe Ala Ala Arg Arg Ala
    25                  30                  35 agg tcc ctc gcc acc agg gcc tcc tcc tct ccg gat tcc tcc ttc           256
Arg Ser Leu Ala Thr Arg Ala Ser Ser Ser Pro Asp Ser Ser Phe
40                  45                  50                  55 ggc tcg cgg atg gag gac tct gtc aag agg acg ctc gcc gac aac ccc       304
Gly Ser Arg Met Glu Asp Ser Val Lys Arg Thr Leu Ala Asp Asn Pro
            60                  65                  70 gtc gtc atc tac tcc aag tcc tgg tgc tcc tac tcc atg gag gtc aag       352
Val Val Ile Tyr Ser Lys Ser Trp Cys Ser Tyr Ser Met Glu Val Lys
    75                  80                  85 gcg ctc ttc aag cgg atc ggc gtc cag ccg cac gtc atc gag ctc gac       400
Ala Leu Phe Lys Arg Ile Gly Val Gln Pro His Val Ile Glu Leu Asp
        90                  95                  100 caa ctc ggc gca cag gga cct cag ttg caa aag gtg tta gag cgg ctg       448
Gln Leu Gly Ala Gln Gly Pro Gln Leu Gln Lys Val Leu Glu Arg Leu
    105                 110                 115 act gga cag tcc act gtt cct aat gtt ttc att ggt gga aag cac att       496
Thr Gly Gln Ser Thr Val Pro Asn Val Phe Ile Gly Gly Lys His Ile
120                 125                 130                 135 ggt ggc tgt aca gat act gtg aag ctt cat cgc aaa ggg gag cta gct       544
Gly Gly Cys Thr Asp Thr Val Lys Leu His Arg Lys Gly Glu Leu Ala
                140                 145                 150 acc atg ctg tca gag ctg gat atc gac gtc aac aac tca tga               586
Thr Met Leu Ser Glu Leu Asp Ile Asp Val Asn Asn Ser
            155                 160 caacattgaa catggtttgc tatactggat atctgaggtt tcaatgactt gagcagtcgt      646
gtaatgagat ttgttagcca tgtttactaa ttcaatgcac attttatgta accgcttccc      706
ttgatcagct acggaatttt gactaatgtg tatccaccgg cgaacttg                   754

<210> SEQ ID NO 50
<211> LENGTH: 164
<212> TYPE: PRT
<213> ORGANISM: Oryza sativa

<400> SEQUENCE: 50

Met Pro Pro Arg Ser Leu Thr Leu Ser Arg Leu Pro Val Ala Ala Leu
1               5                   10                  15

Gly Leu Pro Phe Ser Ser Cys Ser Pro Pro Pro Arg Leu Arg Phe
                20                  25                  30

Pro Phe Ala Ala Arg Arg Ala Arg Ser Leu Ala Thr Arg Ala Ser Ser
            35                  40                  45

Ser Ser Pro Asp Ser Ser Phe Gly Ser Arg Met Glu Asp Ser Val Lys
```

```
                  50                  55                  60
Arg Thr Leu Ala Asp Asn Pro Val Val Ile Tyr Ser Lys Ser Trp Cys
 65                  70                  75                  80

Ser Tyr Ser Met Glu Val Lys Ala Leu Phe Lys Arg Ile Gly Val Gln
                 85                  90                  95

Pro His Val Ile Glu Leu Asp Gln Leu Gly Ala Gln Gly Pro Gln Leu
            100                 105                 110

Gln Lys Val Leu Glu Arg Leu Thr Gly Gln Ser Thr Val Pro Asn Val
        115                 120                 125

Phe Ile Gly Gly Lys His Ile Gly Gly Cys Thr Asp Thr Val Lys Leu
130                 135                 140

His Arg Lys Gly Glu Leu Ala Thr Met Leu Ser Glu Leu Asp Ile Asp
145                 150                 155                 160

Val Asn Asn Ser

<210> SEQ ID NO 51
<211> LENGTH: 44
<212> TYPE: DNA
<213> ORGANISM: Artificial sequence
<220> FEATURE:
<223> OTHER INFORMATION: primer

<400> SEQUENCE: 51
ggaattccag ctgaccacca tggagaccaa tttttccttc gact          44

<210> SEQ ID NO 52
<211> LENGTH: 46
<212> TYPE: DNA
<213> ORGANISM: Artificial sequence
<220> FEATURE:
<223> OTHER INFORMATION: primer

<400> SEQUENCE: 52
gatccccggg aattgccatg ctattgaaat accggcttca atattt        46

<210> SEQ ID NO 53
<211> LENGTH: 44
<212> TYPE: DNA
<213> ORGANISM: Artificial sequence
<220> FEATURE:
<223> OTHER INFORMATION: primer

<400> SEQUENCE: 53
ggaattccag ctgaccacca tgactgtggt tgaaataaaa agcc          44

<210> SEQ ID NO 54
<211> LENGTH: 46
<212> TYPE: DNA
<213> ORGANISM: Artificial sequence
<220> FEATURE:
<223> OTHER INFORMATION: primer

<400> SEQUENCE: 54
gatccccggg aattgccatg ttactgtaga gcatgttgga aatatt        46

<210> SEQ ID NO 55
<211> LENGTH: 38
<212> TYPE: DNA
<213> ORGANISM: Artificial sequence
<220> FEATURE:
<223> OTHER INFORMATION: cloning cassette

<400> SEQUENCE: 55
```

```
ggaattccag ctgaccacca tggcaattcc cggggatc                                     38
```

<210> SEQ ID NO 56
<211> LENGTH: 16
<212> TYPE: PRT
<213> ORGANISM: Artificial sequence
<220> FEATURE:
<223> OTHER INFORMATION: Consensus sequence of the glutaredoxin domain
<220> FEATURE:
<221> NAME/KEY: misc_feature
<222> LOCATION: (1)..(1)
<223> OTHER INFORMATION: Xaa can be Leu, Ile, Val, Met, Asp
<220> FEATURE:
<221> NAME/KEY: misc_feature
<222> LOCATION: (2)..(2)
<223> OTHER INFORMATION: Xaa can be Phe ,Tyr, Ser, Ala
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be Pro, Val
<220> FEATURE:
<221> NAME/KEY: misc_feature
<222> LOCATION: (9)..(9)
<223> OTHER INFORMATION: Xaa can be Phe, Tyr, Trp, His
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be Thr, Ala, Val
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be Leu, Ile, Val

<400> SEQUENCE: 56

Xaa Xaa Xaa Xaa Xaa Xaa Cys Xaa Xaa Cys Xaa Xaa Xaa Xaa Xaa Xaa
1               5                   10                  15

<210> SEQ ID NO 57
<211> LENGTH: 17
<212> TYPE: PRT
<213> ORGANISM: Artificial sequence
<220> FEATURE:
<223> OTHER INFORMATION: Consensus sequence of the glutaredoxin domain
<220> FEATURE:
<221> NAME/KEY: misc_feature
<222> LOCATION: (1)..(1)
<223> OTHER INFORMATION: Xaa can be Leu, Ile, Val, Met, Asp
<220> FEATURE:
<221> NAME/KEY: misc_feature
<222> LOCATION: (2)..(2)
<223> OTHER INFORMATION: Xaa can be Phe ,Tyr, Ser, Ala
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be Pro, Val
<220> FEATURE:
<221> NAME/KEY: misc_feature
<222> LOCATION: (9)..(9)
<223> OTHER INFORMATION: Xaa can be Phe, Tyr, Trp, His
<220> FEATURE:
<221> NAME/KEY: misc_feature

```
<222> LOCATION: (11)..(12)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be Thr, Ala, Val
<220> FEATURE:
<221> NAME/KEY: misc_feature
<222> LOCATION: (14)..(16)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be Leu, Ile, Val

<400> SEQUENCE: 57

Xaa Xaa Xaa Xaa Xaa Xaa Cys Xaa Xaa Cys Xaa Xaa Xaa Xaa Xaa Xaa
1               5                   10                  15

Xaa

<210> SEQ ID NO 58
<211> LENGTH: 12
<212> TYPE: PRT
<213> ORGANISM: Artificial sequence
<220> FEATURE:
<223> OTHER INFORMATION: Domain 1 core sequence of subfamily 1
<220> FEATURE:
<221> NAME/KEY: misc_feature
<222> LOCATION: (1)..(1)
<223> OTHER INFORMATION: Xaa can be Val, Ile
<220> FEATURE:
<221> NAME/KEY: misc_feature
<222> LOCATION: (2)..(2)
<223> OTHER INFORMATION: Xaa can be Val, Phe
<220> FEATURE:
<221> NAME/KEY: misc_feature
<222> LOCATION: (3)..(3)
<223> OTHER INFORMATION: Xaa can be Val, Ile
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be Ser, Ala
<220> FEATURE:
<221> NAME/KEY: misc_feature
<222> LOCATION: (7)..(7)
<223> OTHER INFORMATION: Xaa can be Thr, Ser
<220> FEATURE:
<221> NAME/KEY: misc_feature
<222> LOCATION: (8)..(8)
<223> OTHER INFORMATION: Xaa can be Trp, Tyr
<220> FEATURE:
<221> NAME/KEY: misc_feature
<222> LOCATION: (10)..(10)
<223> OTHER INFORMATION: Xaa can be Pro, Gly, Ser
<220> FEATURE:
<221> NAME/KEY: misc_feature
<222> LOCATION: (11)..(11)
<223> OTHER INFORMATION: Xaa can be Tyr, Phe
<220> FEATURE:
<221> NAME/KEY: misc_feature
<222> LOCATION: (12)..(12)
<223> OTHER INFORMATION: Xaa can be Cys, Ser

<400> SEQUENCE: 58

Xaa Xaa Xaa Xaa Xaa Lys Xaa Xaa Cys Xaa Xaa Xaa
1               5                   10

<210> SEQ ID NO 59
<211> LENGTH: 18
<212> TYPE: PRT
<213> ORGANISM: Artificial sequence
```

```
<220> FEATURE:
<223> OTHER INFORMATION: Domain 2 motif of subfamily 1
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be Val, Ile
<220> FEATURE:
<221> NAME/KEY: misc_feature
<222> LOCATION: (9)..(9)
<223> OTHER INFORMATION: Xaa can be Phe, Tyr
<220> FEATURE:
<221> NAME/KEY: misc_feature
<222> LOCATION: (10)..(10)
<223> OTHER INFORMATION: Xaa can be Val, Ile
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be Lys, Asn
<220> FEATURE:
<221> NAME/KEY: misc_feature
<222> LOCATION: (18)..(18)
<223> OTHER INFORMATION: Xaa can be Cys, Asn

<400> SEQUENCE: 59

Gly Gln Xaa Thr Val Pro Asn Xaa Xaa Xaa Xaa Gly Xaa His Ile Gly
1               5                   10                  15

Gly Xaa

<210> SEQ ID NO 60
<211> LENGTH: 14
<212> TYPE: PRT
<213> ORGANISM: Artificial sequence
<220> FEATURE:
<223> OTHER INFORMATION: Domain 1 core sequence of subfamily 2
<220> FEATURE:
<221> NAME/KEY: misc_feature
<222> LOCATION: (1)..(1)
<223> OTHER INFORMATION: Xaa can be Val, Ile
<220> FEATURE:
<221> NAME/KEY: misc_feature
<222> LOCATION: (3)..(3)
<223> OTHER INFORMATION: Xaa can be Val, Leu
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be Thr, Ala
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be Cys, Ala
<220> FEATURE:
<221> NAME/KEY: misc_feature
<222> LOCATION: (11)..(11)
<223> OTHER INFORMATION: Xaa can be any naturally occurring amino acid
```

```
<220> FEATURE:
<221> NAME/KEY: misc_feature
<222> LOCATION: (12)..(12)
<223> OTHER INFORMATION: Xaa can be Pro, Ala
<220> FEATURE:
<221> NAME/KEY: misc_feature
<222> LOCATION: (13)..(13)
<223> OTHER INFORMATION: Xaa can be Cys, Ser

<400> SEQUENCE: 60

Xaa Val Xaa Xaa Phe Xaa Xaa Xaa Trp Xaa Xaa Xaa Xaa Lys
1               5                   10

<210> SEQ ID NO 61
<211> LENGTH: 4
<212> TYPE: PRT
<213> ORGANISM: Artificial sequence
<220> FEATURE:
<223> OTHER INFORMATION: [CA]-X(2)-[CS] region in domain 1 core sequence
      of subfamily 2
<220> FEATURE:
<221> NAME/KEY: misc_feature
<222> LOCATION: (1)..(1)
<223> OTHER INFORMATION: Xaa can be Cys, Ala
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be Cys, Ser

<400> SEQUENCE: 61

Xaa Xaa Xaa Xaa
1

<210> SEQ ID NO 62
<211> LENGTH: 12
<212> TYPE: PRT
<213> ORGANISM: Artificial sequence
<220> FEATURE:
<223> OTHER INFORMATION: Domain 2 core sequence of subfamily 2
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be Val, Ile
<220> FEATURE:
<221> NAME/KEY: misc_feature
<222> LOCATION: (5)..(5)
<223> OTHER INFORMATION: Xaa can be Glu, Asp
<220> FEATURE:
<221> NAME/KEY: misc_feature
<222> LOCATION: (6)..(6)
<223> OTHER INFORMATION: Xaa can be Ala, Val
<220> FEATURE:
<221> NAME/KEY: misc_feature
<222> LOCATION: (7)..(7)
<223> OTHER INFORMATION: Xaa can be Glu, Asp
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be Glu, Asp
<220> FEATURE:
<221> NAME/KEY: misc_feature
<222> LOCATION: (12)..(12)
<223> OTHER INFORMATION: Xaa can be Ile, Val
```

```
<400> SEQUENCE: 62

Phe Xaa Xaa Xaa Xaa Xaa Xaa Glu Xaa Xaa Xaa Xaa
1               5                   10

<210> SEQ ID NO 63
<211> LENGTH: 17
<212> TYPE: PRT
<213> ORGANISM: Artificial sequence
<220> FEATURE:
<223> OTHER INFORMATION: Domain 1 core sequence of subfamily 3
<220> FEATURE:
<221> NAME/KEY: misc_feature
<222> LOCATION: (2)..(2)
<223> OTHER INFORMATION: Xaa can be Val, Met
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (8)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 63

Val Xaa Xaa Xaa Xaa Lys Gly Xaa Xaa Xaa Xaa Pro Xaa Cys Gly Phe
1               5                   10                  15

Ser

<210> SEQ ID NO 64
<211> LENGTH: 14
<212> TYPE: PRT
<213> ORGANISM: Artificial sequence
<220> FEATURE:
<223> OTHER INFORMATION: Domain 2 core sequence of subfamily 3
<220> FEATURE:
<221> NAME/KEY: misc_feature
<222> LOCATION: (2)..(2)
<223> OTHER INFORMATION: Xaa can be Leu, Ile
<220> FEATURE:
<221> NAME/KEY: misc_feature
<222> LOCATION: (3)..(3)
<223> OTHER INFORMATION: Xaa can be Phe, Tyr
<220> FEATURE:
<221> NAME/KEY: misc_feature
<222> LOCATION: (4)..(4)
<223> OTHER INFORMATION: Xaa can be Val, Ile
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be Gly, Lys
<220> FEATURE:
<221> NAME/KEY: misc_feature
<222> LOCATION: (8)..(8)
<223> OTHER INFORMATION: Xaa can be Phe, Leu
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be Cys, Ser
<220> FEATURE:
<221> NAME/KEY: misc_feature
<222> LOCATION: (14)..(14)
<223> OTHER INFORMATION: Xaa can be Ile, Val
```

```
<400> SEQUENCE: 64

Gln Xaa Xaa Xaa Xaa Xaa Glu Xaa Xaa Gly Gly Xaa Asp Xaa
1               5                   10

<210> SEQ ID NO 65
<211> LENGTH: 12
<212> TYPE: PRT
<213> ORGANISM: Artificial sequence
<220> FEATURE:
<223> OTHER INFORMATION: Domain 1 core sequence of subfamily 4
<220> FEATURE:
<221> NAME/KEY: misc_feature
<222> LOCATION: (1)..(1)
<223> OTHER INFORMATION: Xaa can be Val, Ile

<400> SEQUENCE: 65

Xaa Val Ile Phe Ser Lys Ser Tyr Cys Pro Tyr Cys
1               5                   10

<210> SEQ ID NO 66
<211> LENGTH: 10
<212> TYPE: PRT
<213> ORGANISM: Artificial sequence
<220> FEATURE:
<223> OTHER INFORMATION: Domain 2 core sequence of subfamily 4
<220> FEATURE:
<221> NAME/KEY: misc_feature
<222> LOCATION: (6)..(6)
<223> OTHER INFORMATION: Xaa can be any naturally occurring amino acid

<400> SEQUENCE: 66

Val Val Glu Leu Asp Xaa Arg Glu Asp Gly
1               5                   10

<210> SEQ ID NO 67
<211> LENGTH: 21
<212> TYPE: PRT
<213> ORGANISM: Artificial sequence
<220> FEATURE:
<223> OTHER INFORMATION: Domain 2 core sequence of subfamily 4
<220> FEATURE:
<221> NAME/KEY: misc_feature
<222> LOCATION: (11)..(11)
<223> OTHER INFORMATION: Xaa can be Val, Ile
<220> FEATURE:
<221> NAME/KEY: misc_feature
<222> LOCATION: (12)..(12)
<223> OTHER INFORMATION: Xaa can be Asn, His
<220> FEATURE:
<221> NAME/KEY: misc_feature
<222> LOCATION: (16)..(16)
<223> OTHER INFORMATION: Xaa can be Leu, Ile

<400> SEQUENCE: 67

Val Gly Arg Arg Thr Val Pro Gln Val Phe Xaa Xaa Gly Lys His Xaa
1               5                   10                  15

Gly Gly Ser Asp Asp
            20
```

NUCLEIC ACID SEQUENCES ENCODING PROTEINS ASSOCIATED WITH ABIOTIC STRESS RESPONSE

RELATED APPLICATIONS

This application is a continuation application of U.S. application Ser. No. 10/523,362, filed on Feb. 7, 2005, now abandoned which is a national stage application (under 35 U.S.C. §371) of PCT/EP2003/006994 filed Jul. 1, 2003, which claims benefit of European application 02017671.5 filed Aug. 7, 2002. The entire content of each above-mentioned application is hereby incorporated by reference in its entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing__13311__00080. The size of the text file is 115 KB, and the text file was created on Aug. 24, 2011.

BACKGROUND OF THE INVENTION

This invention relates generally to nucleic acid sequences encoding proteins that are associated with abiotic stress responses and abiotic stress tolerance in plants. In particular, this invention relates to nucleic acid sequences encoding proteins that confer drought, heat, cold, and/or salt tolerance to plants.

Abiotic environmental stresses, such as drought stress, salinity stress, heat stress, and cold stress, are major limiting factors of plant growth and productivity (Boyer. 1982. *Science* 218, 443-448). Crop losses and crop yield losses of major crops such as rice, maize (corn) and wheat caused by these stresses represent a significant economic and political factor and contribute to food shortages in many underdeveloped countries.

Plants are typically exposed during their life cycle to conditions of reduced environmental water content. Most plants have evolved strategies to protect themselves against these conditions of low water or desiccation (drought). However, if the severity and duration of the drought conditions are too great, the effects on plant development, growth and yield of most crop plants are profound. Continuous exposure to drought causes major alterations in the plant metabolism. These great changes in metabolism ultimately lead to cell death and consequently yield losses.

Developing stress-tolerant plants is a strategy that has the potential to solve or mediate at least some of these problems (McKersie and Leshem, 1994. *Stress and Stress Coping in Cultivated Plants*, Kluwer Academic Publishers). However, traditional plant breeding strategies to develop new lines of plants that exhibit resistance (tolerance) to these types of stresses are relatively slow and require specific resistant lines for crossing with the desired line. Limited germplasm resources for stress tolerance and incompatibility in crosses between distantly related plant species represent significant problems encountered in conventional breeding. Additionally, the cellular processes leading to drought, cold and salt tolerance are complex in nature and involve multiple mechanisms of cellular adaptation and numerous metabolic pathways (McKersie and Leshem, 1994. *Stress and Stress Coping in Cultivated Plants*, Kluwer Academic Publishers). This multi-component nature of stress tolerance has not only made breeding for tolerance largely unsuccessful, but has also limited the ability to genetically engineer stress tolerance plants using biotechnological methods.

Drought, heat, cold and salt stresses have a common theme important for plant growth and that is water availability. Plants are exposed during their entire life cycle to conditions of reduced environmental water content. Most plants have evolved strategies to protect themselves against these conditions. However, if the severity and duration of the drought conditions are too great, the effects on plant development, growth and yield of most crop plants are profound. Since high salt content in some soils result in less available water for cell intake, its effect is similar to those observed under drought conditions. Additionally, under freezing temperatures, plant cells loose water as a result of ice formation that starts in the apoplast and withdraws water from the symplast (McKersie and Leshem, 1994. *Stress and Stress Coping in Cultivated Plants*, Kluwer Academic Publishers). Commonly, a plant's molecular response mechanisms to each of these stress conditions are common.

The results of current research indicate that drought tolerance is a complex quantitative trait and that no real diagnostic marker is available yet. High salt concentrations or dehydration may cause damage at the cellular level during drought stress but the precise injury is not entirely clear (Bray, 1997. *Trends Plant Sci*. 2, 48-54). This lack of a mechanistic understanding makes it difficult to design a transgenic approach to improve drought tolerance. However, an important consequence of damage may be the production of reactive oxygen radicals that cause cellular injury, such as lipid peroxidation or protein and nucleic acid modification. Details of oxygen free radical chemistry and their reaction with cellular components such as cell membranes have been described (McKersie and Leshem, 1994. *Stress and Stress Coping in Cultivated Plants*, Kluwer Academic Publishers).

There are numerous sites of oxygen activation in the plant cell, which are highly controlled and tightly coupled to prevent release of intermediate products (McKersie and Leshem, 1994. *Stress and Stress Coping in Cultivated Plants*, Kluwer Academic Publishers). Under abiotic stress situations, it is likely that this control or coupling breaks down and the process "dysfunctions" leaking activated oxygen. These uncoupling events are not detrimental provided that they are short in duration and that the oxygen scavenging systems are able to detoxify the various forms of activated oxygen. If the production of activated oxygen exceeds the plant's capacity to detoxify it, deleterious degenerative reactions occur. At the subcellular level, disintegration of membranes and aggregation of proteins are typical symptoms. Therefore it is the balance between the production and the scavenging of activated oxygen that is critical to the maintenance of active growth and metabolism of the plant and overall environmental (abiotic) stress tolerance.

Preventing or diminishing the accumulation of oxygen free radicals in response to drought is a potential way to engineer tolerance (Allen, 1995. Plant Physiol. 107, 1049-1054). Overexpression of antioxidant enzymes or ROS-scavenging enzymes is one possibility for the induction of functional detoxification systems. For example, transgenic alfalfa plants expressing Mn-superoxide dismutase tend to have reduced injury after water-deficit stress (McKersie et al., 1996. Plant Physiol. 111, 1177-1181). These same transgenic plants have increased biomass production in field trials (McKersie et al., 1999. Plant Physiology, 119: 839-847; McKersie et al., 1996. Plant Physiol. 111, 1177-1181). Transgenic plants that overproduce osmolytes such as mannitol, fructans, proline or glycine-betaine also show increased resistance to some forms of abiotic stress and it is proposed that the synthesized osmolytes act as ROS scavengers (Tarczynski. et al. 1993. Science 259, 508-510; Sheveleva, et al. 1997. Plant Physiol. 115, 1211-1219). Overexpression of glutathione reductase has increased antioxidant capacity and reduced photoinhibition in popular trees (Foyer et al., 1995. Plant Physiology 109: 1047-57).

The glutaredoxin and thioredoxin proteins are small heat-stable oxidoreductases that have been conserved throughout evolution. They function in many cellular processes, including deoxyribonucleotide synthesis, protein folding, sulfur metabolism and most notably repair of oxidatively damaged proteins. They have also been implicated in the regulation of redox homeostasis in the cell and redox potential has been implicated in changes in gene expression.

Thioredoxins have a dithiol/disulfide (CGPC) at their active site and are the major cellular protein disulfide reductases. Cytosolic isoforms are present in most organisms. Mitochondria have a separate thioredoxin system and plants have chloroplast thioredoxins, which regulate photosynthetic enzymes by light via ferredoxin-thioredoxin reductase. Thioredoxins are critical for redox regulation of protein function and signaling via thiol redox control. Several transcription factors require thioredoxin reduction for DNA binding (Arner and Holmgren, 2000. European Journal of Biochemistry 267: 6102-6109; Spyrou et al., 2001. Human Genetics 109: 429-439).

Glutaredoxins are small heat-stable proteins that are active as glutathione-dependent oxidoreductases. They catalyze glutathione-disulfide oxidoreductions overlapping the functions of thioredoxins and using reducing equivalents from NADPH via glutathione reductase. In *Saccharomyces cerevisiae*, two genes, GRX1 and GRX2, whose expression is induced in response to various stress conditions including oxidative, osmotic, and heat stress, encode glutaredoxins. Furthermore, both genes are activated by the high-osmolarity glycerol pathway and negatively regulated by the Ras-protein kinase (Grant C M. 2001. Molecular Microbiology 39: 533-541; Grant C M et al., 2001. Biochimica et Biophysica Acta—Gene Structure & Expression 1490: 33-42).

Another subfamily of yeast glutaredoxins (Grx3, Grx4, and Grx5) differs from the first in containing a single cysteine residue at the putative active site (Rodriguez-Manzaneque et al., 1999. Molecular & Cellular Biology 19: 8180-8190). The role of these enzymes is not fully understood.

In addition to the two gene pairs encoding cytoplasmic glutaredoxins (GRX1, GRX2), *Saccharomyces cerevisiae* also contains two gene pairs for thioredoxins (TRX1, TRX2). Only a quadruple mutant is non-viable and either a single glutaredoxin or a single thioredoxin can sustain viability, indicating some cross function between the two systems (Draculic et al., 2000. Molecular Microbiology 36: 1167-1174).

Plants also contain glutaredoxins genes. A glutaredoxin (thioltransferase), which catalyzes thiol/disulfide exchange reaction, was isolated from rice (*Oryza saliva* L.) (Sha et al., 1997. Journal of Biochemistry 121: 842-848; Sha et al., 1997. Gene 188: 23-28; GenBank accession number D86744). Mulitple forms of glutaredoxin have also been predicted in the *Arabiposis* genome (GenBank).

Dehydroascorbate reductase (DHAR; glutathione: dehydroascorbate oxidoreductase, EC 1.8.5.1) is an enzyme that is critical for maintenance of an appropriate level of ascorbate in plant cells by the cycling of dehydroascorbate to replenish ascorbate. DHAR was considered a specific enzyme of the ascorbate-glutathione cycle. However, at least four distinct proteins can catalyze in vitro both glutathione-dependent DHA reduction and other reactions mainly related to thiol-disulphide exchange. These glutaredoxin enzymes (thiol-transferases) have both thiol-disulfide oxidoreductase and dehydroascorbate reductase activities (Kato et al., 1997. Plant & Cell Physiology 38: 173-178; Detullio et al., 1998. Plant Physiology & Biochemistry 36: 433-440). Therefore glutaredoxins may also function in vivo as DHAR.

There have been no reports on the mutation or overexpression of either thioredoxin or glutaredoxin in plant cells to determine their function in terms of oxidative stress tolerance or drought tolerance.

SUMMARY OF THE INVENTION

It is the object of this invention to identify new, unique genes capable of conferring stress tolerance to plants upon over-expression.

The present invention provides a transgenic plant cell transformed by Oxidoreductase Stress-Related Protein (ORSRP) coding nucleic acid, wherein expression of the nucleic acid sequence in the plant cell results in increased tolerance and/or resistance to environmental stress as compared to a corresponding non-transformed wild type plant cell. One preferred wild type plant cell is a non-transformed *Arabidopsis* plant cell. An example here is the *Arabidopsis* wild type C24 (Nottingham *Arabidopsis* Stock Centre, UK; NASC Stock N906).

Preferably the oxidoreductase stress related protein is heat-stable. The invention provides that the environmental stress can be salinity, drought, temperature, metal, chemical, pathogenic and oxidative stresses, or combinations thereof.

The object of the invention is a transgenic plant cell, wherein the ORSRP is heat-stable. Further, in said transgenic plant cell, the ORSRP is selected from yeast or plant. Preferably, in a transgenic plant of the instant invention, the ORSRP is selected from the group comprising glutaredoxin and/or thioredoxin protein.

Further the invention pertains to a transgenic plant cell, wherein the ORSRP coding nucleic acid is selected from the group comprising SEQ ID No. 1, 3, 5, 7, 9, 11, 13 of yeast and/or SEQ ID No. 15, 17, 19, 21, 23, 25, 27, 29, 31, 33, 35, 37, 39, 41, 43, 45, 47, 49 of plants and/or homologs thereof. Object of the invention is also a transgenic plant cell, wherein the ORSRP coding nucleic acid is at least about 50% homologous to SEQ ID No. 1, 3, 5, 7, 9, 11, 13, 15, 17, 19, 21, 23, 25, 27, 29, 31, 33, 35, 37, 39, 41, 43, 45, 47, 49.

The invention further provides a seed produced by a transgenic plant transformed by a ORSRP coding nucleic acid, wherein the plant is true breeding for increased tolerance to environmental stress as compared to a wild type plant cell. The transgenic plant might be a monocot, a dicot or a gymnosperm plant. The invention further provides a seed produced by a transgenic plant expressing an ORSRP wherein the plant is true breeding for increased tolerance to environmental stress as compared to a wild type plant cell.

The invention further provides an agricultural product produced by any of the below-described transgenic plants, plant parts such as leafs, roots, stems, buds, flowers or seeds. The invention further provides a isolated recombinant expression vector comprising a ORSRP encoding nucleic acid.

The invention further provides a method of producing a transgenic plant with a ORSRP coding nucleic acid, wherein expression of the nucleic acid in the plant results in increased tolerance to environmental stress as compared to a wild type plant comprising: (a) transforming a plant cell with an expression vector comprising a ORSRP coding nucleic acid, and (b)

generating from the plant cell a transgenic plant with an increased tolerance to environmental stress as compared to a wild type plant.

BRIEF DESCRIPTION OF THE DRAWINGS

FIG. 2: Amino acid alignment of yeast and plant cDNA sequences of glutaredoxin subfamily 1 showing the presence of two conserved domains. The abbreviations correspond to the "Gene ID" as explained in Table 6.

FIG. 3: Amino acid alignment of glutaredoxin subfamily 1 domain 1 across yeast and plant cDNA sequences (GRX1, SEQ ID NO: 2; GRX2, SEQ ID NO: 4, AtQ9FM49, SEQ ID NO: 26; AtQ9FNE2, SEQ ID NO: 28; AtQ9SK75, SEQ ID NO: 34; BN1106C12219, SEQ ID NO: 16; BN1106C2202, SEQ ID NO: 20; OZ1116C26232, SEQ ID NO: 50; OZ1116C2194, SEQ ID NO: 48). The amino acid position at the start of the alignment is shown in parenthesis.

FIG. 4: Amino acid alignment of Glutaredoxin subfamily 1 domain 2 across yeast and plant cDNA sequences (GRX1, SEQ ID NO: 2; GRX2, SEQ ID NO: 4, AtQ9FM49, SEQ ID NO: 26; AtQ9FNE2, SEQ ID NO: 28; AtQ9SK75, SEQ ID NO: 34; BN1106C12219, SEQ ID NO: 16; BN1106C2202, SEQ ID NO: 20; OZ1116C26232, SEQ ID NO: 50; OZ1116C2194, SEQ ID NO: 48). The amino acid position at the start of the alignment is shown in parenthesis.

FIG. 7: Amino acid alignment of Glutaredoxin subfamily 2 domain 2 across yeast and plant cDNA sequences (THX1, SEQ ID NO: 12; THX2, SEQ ID NO: 14, GRX3, SEQ ID NO: 6; GRX4, SEQ ID NO: 8; BN1106C23043, SEQ ID NO: 24; AtQ65541, SEQ ID NO: 42; AtQ9ZPH2, SEQ ID NO: 44). The amino acid position at the start of the alignment is shown in parenthesis.

FIG. 8: Amino add alignments of yeast and plant cDNA sequences of glutaredoxin subfamily 3 showing the presence of two conserved domains. The abbreviations correspond to the "Gene ID" as explained in Table 6.

FIG. 9: Amino acid alignment of glutaredoxin subfamily 3 domain 1 across yeast and plant cDNA sequences (GRX5, SEQ ID NO: 10; AtQ9SV38, SEQ ID NO: 38; AtO80451, SEQ ID NO: 40; AtQ9LW13, SEQ ID NO: 36). The amino acid position at the start of the alignment is shown in parenthesis.

FIG. 10: Amino acid alignment of Glutaredoxin subfamily 3 domain 2 across yeast and plant cDNA sequences (GRX5, SEQ ID NO: 10; AtQ9SV38, SEQ ID NO: 38; AtO80451, SEQ ID NO: 40; AtQ9LW13, SEQ ID NO: 36). The amino acid position at the start of the alignment is shown in parenthesis.

FIG. 11: Amino acid alignments of yeast and plant cDNA sequences of glutaredoxin subfamily 4 showing the presence of two conserved domains. The abbreviations correspond to the "Gene ID" as explained in Table 6.

FIG. 12: Amino acid alignment of glutaredoxin subfamily 4 domain 1 across yeast and plant cDNA sequences (AtQ9FVX1, SEQ ID NO: 30; EN1106C21909, SEQ ID NO: 18; AtQ9M457, SEQ ID NO: 32; EN1106C2582, SEQ ID NO: 22; OZ1116C12744, SEQ ID NO: 46). The amino acid position at the start of the alignment is shown in parenthesis.

FIG. 13: Amino acid alignment of glutaredoxin subfamily 4 domain 2 across yeast and plant cDNA sequences (AtQ9FVX1, SEQ ID NO: 30; EN1106C21909, SEQ ID NO: 18; AtQ9M457, SEQ ID NO: 32; EN1106C2582, SEQ ID NO: 22; OZ1116C12744, SEQ ID NO: 46). The amino acid position at the start of the alignment is shown in parenthesis.

DETAILED DESCRIPTION OF THE INVENTION

Figure 1:
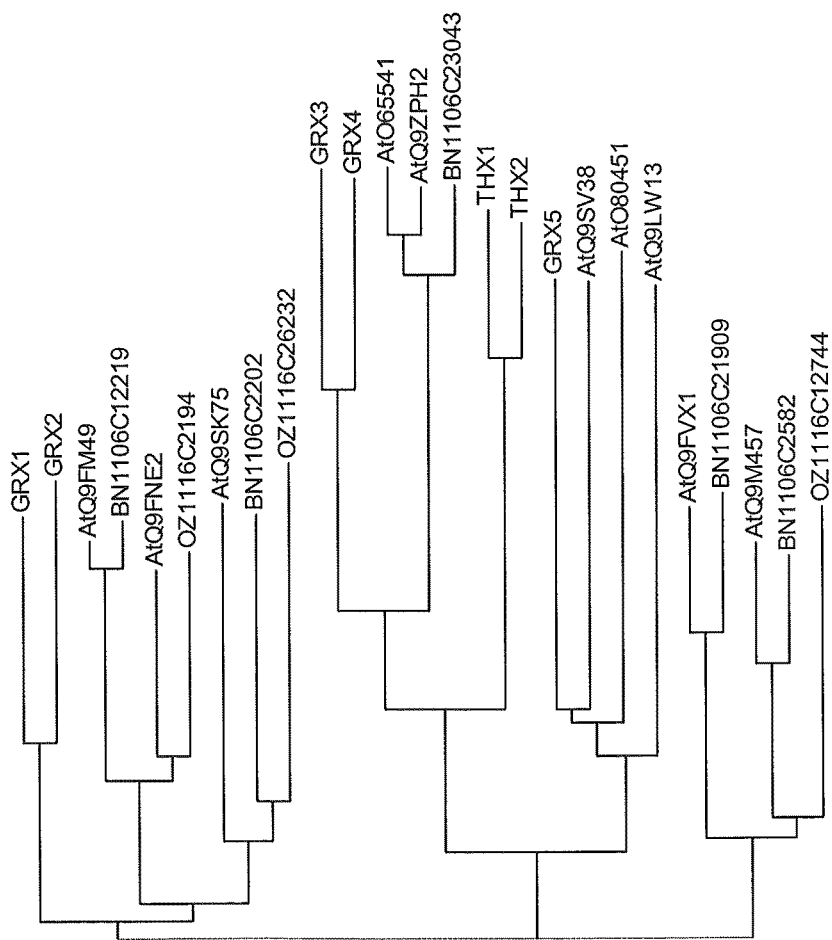
FIG. 1: The glutaredoxin gene family showing the four subfamilies of glutaredoxin and thioredoxin coding sequences as determined by amino acid sequence homology. The abbreviations correspond to the "Gene ID" as explained in Table 6.

With regard to invention described here, "transgenic or transgene" means all those plants or parts thereof which have been brought about by genetic manipulation methods and in which either a) the nucleic acid sequence as depicted in SEQ ID NO: 1, 3, 5, 7, 9, 11, 13, 15, 17, 19, 21, 23, 25, 27, 29, 31, 33, 35, 37, 39, 41, 43, 45, 47, 49 or a homologe thereof, or
b) a genetic regulatory element, for example a promoter, which is functionally linked to the nucleic acid sequence as depicted in SEQ ID NO: 1, 3, 5, 7, 9, 11, 13, 15, 17, 19, 21, 23, 25, 27, 29, 31, 33, 35, 37, 39, 41, 43, 45, 47, 49 or a homologe thereof, or
c) (a) and (b)

is/are not present in its/their natural genetic environment or has/have been modified by means of genetic manipulation methods, it being possible for the modification to be, by way of example, a substitution, addition, deletion, inversion or insertion of one or more nucleotide radicals. "Natural genetic environment" means the natural chromosomal locus in the organism of origin or the presence in a genomic library. In the case of a genomic library, the natural, genetic environment of the nucleic acid sequence is preferably at least partially still preserved. The environment flanks the nucleic acid sequence at least on one side and has a sequence length of at least 50 bp, preferably at least 500 bp, particularly preferably at least 1000 bp, very particularly preferably at least 5000 bp.

In said method, the used ORSRP is heat-stable. Further, the ORSRP used in the instant method described above is a glutaredoxin or thioredoxin protein. Herein the ORSRP coding nucleic acid is selected from the group comprising SEQ ID No. 1, 3, 5, 7, 9, 11, 13 of yeast and/or SEQ ID No. 15, 17, 19, 21, 23, 25, 27, 29, 31, 33, 35, 37, 39, 41, 43, 45, 47, 49 of plants and/or homologs thereof. Further, the ORSRP coding nucleic acid used in the said method is at least about 50% homologous to SEQ ID No. 1, 3, 5, 7, 9, 11, 13, 15, 17, 19, 21, 23, 25, 27, 29, 31, 33, 35, 37, 39, 41, 43, 45, 47, 49.

A plant or plant cell is considered "true breeding" for a particular trait if it is genetically homozygous for that trait to the extent that, when the true-breeding plant is self-pollinated, a significant amount of independent segregation of the trait among the progeny is not observed. In the present invention, the trait arises from the transgenic expression of one or more DNA sequences introduced into a plant cell or plant.

The present invention also provides methods of modifying stress tolerance of a plant comprising, modifying the expression of a ORSRP nucleic acid in the plant. The invention provides one method of producing a transgenic plant with a synthetic, novel or modified transcription factor that acts by increasing or decreasing the transcription of a ORSRP gene.

The present invention also provides methods of modifying stress tolerance of a crop plant comprising utilizing a ORSRP coding nucleic acid sequence to identify individual plants in populations segregating for either increased or decreased environmental stress tolerance (DNA marker).

In the said method of modifying stress tolerance of a plant the ORSRP encoding nucleic acid is selected from the group comprising SEQ ID No. 1, 3, 5, 7, 9, 11, 13 of yeast and/or SEQ ID No. 15, 17, 19, 21, 23, 25, 27, 29, 31, 33, 35, 37, 39, 41, 43, 45, 47, 49 of plants and/or homologs thereof. Further the ORSRP coding nucleic acid used therein is at least about 50% homologous to SEQ ID No. SEQ ID No. 1, 3, 5, 7, 9, 11, 13, 15, 17, 19, 21, 23, 25, 27, 29, 31, 33, 35, 37, 39, 41, 43, 45, 47, 49. Also an expression vector as described in the instant invention might be used in the said method.

In an variant method of said method of modifying stress tolerance, the plant is transformed with an inducible promoter that directs expression of the ORSRP. For example, the promoter is tissue specific. In a variant method, the used promoter is developmentally regulated.

In the instant method of modifying stress tolerance in plant the ORSRP expression is modified by administration of an antisense molecule and/or by double stranded RNA interference that inhibits expression of ORSPR. In another variant of the method, ORSRP expression is modified by administration of an targeting nucleic sequence complementary to the regulatory region of the ORSRP encoding nucleic acid and/or by a transcription factor and/or by a zinc finger protein.

The present invention relates to a method for the identification of loci for stress tolerance phenotypes in individual plants. Genomic regions associated with environmental stress tolerance can be identified using Quantitative Trait Loci (QTL) mapping analysis. This approach may use either variation in the glutaredoxin or thioredoxin nucleic acid sequence, variation in the surrounding genomic sequences or variation in the expression level of glutaredoxin or thioredoxin nucleic acid sequence as the quantitative trait.

The invention provides that the above methods can be performed such that the stress tolerance is either increased or decreased.

This invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting.

The present invention describes that particularly glutaredoxin or thioredoxin genes are useful for increasing a plant's tolerance and/or resistance to environmental stress. Accordingly, the present invention provides glutaredoxin and thioredoxin gene sequences selected from the group consisting of SEQ ID No. 1, 3, 5, 7, 9, 11, 13 from *Saccharomyces cerevisiae*.

This invention provides sequences of glutaredoxin and thioredoxin nucleic acids that are responsive to drought and environmental conditions in *Brassica napus, Arabidopsis thaliana* and *Oryza sativa* according to SEQ ID 15, 17, 19, 21, 23, 25, 27, 29, 31, 33, 35, 37, 39, 41, 43, 45, 47, 49 and that exhibit homology at the nucleic acid and amino acid level to the yeast genes in SEQ ID 3 and 7, respectively. These plant homologs are functionally equivalent according to this invention to yeast genes of SEQ ID 3 and 7 and can be used to provide environmental stress tolerance in plants.

The invention also pertain to an isolated Oxidoreductase Stress Related Protein (ORSRP) which is selected form the group comprising SEQ ID No. 16, 18, 20, 22, 24, 44 and 50. Further the isolated Oxidoreductase Stress Related Protein (ORSRP) as mentioned before is heat-stable. The isolated Oxidoreductase Stress Related Protein (ORSRP) selected form the group comprising SEQ ID No. 16, 18, 20, 22, 24, 44 and 50 is selected form plant. Preferred is an isolated Oxidoreductase Stress Related Protein (ORSRP) selected form the group comprising SEQ ID No. 16, 18, 20, 22, 24, 44 and 50 wherein the ORSRP is a glutaredoxin or thioredoxin protein.

Another object of the instant invention is an isolated Oxidoreductase Stress Related Protein (ORSRP) encoding nucleic acid selected from the group comprising SEQ ID No. 15, 17, 19, 21, 23, 45 and 49. Said isolated Oxidoreductase Stress Related Protein (ORSRP) encoding nucleic acid encoding an ORSRP which is heat-stable. Thereby the isolated Oxidoreductase Stress Related Protein (ORSRP) encoding nucleic acid selected from the group comprising SEQ ID No. 15, 17, 19, 21, 23, 45 and 49 encoding an ORSRP which is selected from plants. Preferred is an isolated Oxidoreductase Stress Related Protein (ORSRP) encoding nucleic acid selected from the group comprising SEQ ID No. 15, 17, 19, 21, 23, 45 and 49 wherein the ORSRP is a glutaredoxin or thioredoxin.

Homologs of the aforementioned sequences can be isolated advantageously from yeast, fungi or plants, preferably from yeasts such as from the genera *Saccharomyces, Pichia, Candida, Hansenula, Torulopsis* or *Schizosaccharomyces*, or plants such as *Arabidopsis thaliana*, maize, wheat, rye, oat, triticale, rice, barley, soybean, peanut, cotton, borage, sufflower, linseed, primrose, rapeseed, canola and turnip rape, manihot, pepper, sunflower, tagetes, solanaceous plant such as potato, tobacco, eggplant and tomato, *Vicia* species, pea, alfalfa, bushy plants such as coffee, cacao, tea, *Salix* species, trees such as oil palm, coconut, perennial grass, such as ryegrass and fescue, and forage crops, such as alfalfa and clover and from spruce, pine or fir for example, more preferably from *Saccharomyces cerevisiae* or plants.

The glutaredoxin or thioredoxin of the present invention are preferably produced by recombinant DNA techniques. For example, a nucleic acid molecule encoding the protein is cloned into an expression vector, for example in to a binary vector, the expression vector is introduced into a host cell, for example the *Arabidopsis thaliana* wild type NASC N906 or any other plant cell as described in the examples see below, and the glutaredoxin or thioredoxin is expressed in said host cell. Examples for binary vectors are pBIN19, pBI101, pBinAR, pGPTV or pPZP (Hajukiewicz, P. et al., 1994, plant Mol. Biol., 25: 989-994).

As used herein, the term "environmental stress" refers to any sub-optimal growing condition and includes, but is not limited to, sub-optimal conditions associated with salinity, drought, temperature, metal, chemical, pathogenic and oxidative stresses, or combinations thereof. In preferred embodiments, the environmental stress can be salinity, drought, heat, or low temperature, or combinations thereof, and in particular, can be low water content or low temperature. Wherein drought stress means any environmental stress which leads to a lack of water in plants or reduction of water supply to plants, wherein low temperature stress means freezing of plants below +4° C. as well as chilling of plants below 15° C. and wherein high temperature stress means for example a temperature above 35° C. The range of stress and stress response depends on the different plants which are used for the invention, i.e. it differs for example between a plant such as wheat and a plant such as *Arabidopsis*. It is also to be understood that as used in the specification and in the claims, "a" or "an" can mean one or more, depending upon the context in which it is used. Thus, for example, reference to "a cell" can mean that at least one cell can be utilized.

As also used herein, the terms "nucleic acid" and "nucleic acid molecule" are intended to include DNA molecules (e.g., cDNA or genomic DNA) and RNA molecules (e.g., mRNA) and analogs of the DNA or RNA generated using nucleotide analogs. This term also encompasses untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. The nucleic acid molecule can be single-stranded or double-stranded, but preferably is double-stranded DNA.

An "isolated" nucleic acid molecule is one that is substantially separated from other nucleic acid molecules, which are present in the natural source of the nucleic acid. Preferably, an "isolated" nucleic acid is free of some of the sequences that naturally flank the nucleic acid (i.e., sequences located at the 5' and 3' ends of the nucleic acid) in the genomic DNA of the organism from which the nucleic acid is derived. For example, in various embodiments, the isolated glutaredoxin or thioredoxin nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

A nucleic acid molecule of the present invention, e.g., a nucleic acid molecule encoding an ORSRP or a portion thereof which confers tolerance and/or resistance to environmental stress in plants, can be isolated using standard molecular biology techniques and the sequence information provided herein. For example, a *Arabidopsis thaliana* glutaredoxin or thioredoxin cDNA can be isolated from a *A. thaliana* library using all or portion of one of the sequences of SEQ ID 1, 3, 5, 7, 9, 11, 13 of yeast. Moreover, a nucleic acid molecule encompassing all or a portion of one of the sequences of SEQ IDs 1, 3, 5, 7, 9, 11, 13 of yeast can be isolated by the polymerase chain reaction using oligonucleotide primers designed based upon this sequence. For example, mRNA can be isolated from plant cells (e.g., by the guanidinium-thiocyanate extraction procedure of Chirgwin et al., 1979 Biochemistry 18:5294-5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in SEQ IDs 1, 3, 5, 7, 9, 11, 13 of yeast. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to a glutaredoxin or thioredoxin nucleotide sequence can be prepared by standard synthetic techniques, e.g., using an automated DNA synthesizer.

In a preferred embodiment, an isolated nucleic acid molecule of the invention comprises one of the nucleotide sequences shown in SEQ IDs 1, 3, 5, 7, 9, 11, 13 of yeast and/or SEQ ID No. 15, 17, 19, 21, 23, 25, 27, 29, 31, 33, 35, 37, 39, 41, 43, 45, 47, 49 of plants encoding the glutaredoxin or thioredoxin (i.e., the "coding region"), as well as 5' untranslated sequences and 3' untranslated sequences.

Moreover, the nucleic acid molecule of the invention can comprise only a portion of the coding region of one of the sequences in SEQ IDs 1, 3, 5, 7, 9, 11, 13 of yeast and/or SEQ ID No. 15, 17, 19, 21, 23, 25, 27, 29, 31, 33, 35, 37, 39, 41, 43, 45, 47, 49 of plants, for example, a fragment which can be used as a probe or primer or a fragment encoding a biologically active portion of a glutaredoxin or thioredoxin.

Portions of proteins encoded by the glutaredoxin or thioredoxin nucleic acid molecules of the invention are preferably biologically active portions of one of the glutaredoxin or thioredoxin described herein. As used herein, the term "biologically active portion of" a glutaredoxin or thioredoxin is intended to include a portion, e.g., a domain/motif, of a glutaredoxin or thioredoxin that participates in a stress tolerance and/or resistance response in a plant. To determine whether a glutaredoxin or thioredoxin, or a biologically active portion thereof, results in increased stress tolerance in a plant, a stress analysis of a plant comprising the glutaredoxin or thioredoxin may be performed. Such analysis methods are well known to those skilled in the art, as detailed in the Examples. More specifically, nucleic acid fragments encoding biologically active portions of a glutaredoxin or thioredoxin can be prepared by isolating a portion of one of the sequences in SEQ IDs 1, 3, 5, 7, 9, 11, 13 of and/or SEQ ID No. 15, 17, 19, 21, 23, 25, 27, 29, 31, 33, 35, 37, 39, 41, 43, 45, 47, 49 of plants, expressing the encoded portion of the glutaredoxin or thioredoxin or peptide (e.g., by recombinant expression in vitro) and assessing the activity of the encoded portion of the glutaredoxin or thioredoxin or peptide.

Biologically active portions of a glutaredoxin or thioredoxin are encompassed by the present invention and include peptides comprising amino acid sequences derived from the amino acid sequence of a glutaredoxin or thioredoxin gene, or the amino acid sequence of a protein homologous to a glutaredoxin or thioredoxin, which include fewer amino acids than a full length glutaredoxin or thioredoxin or the full length protein which is homologous to a glutaredoxin or thioredoxin, and exhibits at least some enzymatic activity of a glutaredoxin or thioredoxin. Typically, biologically active portions (e.g., peptides which are, for example, 5, 10, 15, 20, 30, 35, 36, 37, 38, 39, 40, 50, 100 or more amino acids in length) comprise a domain or motif with at least one activity of a glutaredoxin or thioredoxin enzyme. Moreover, other biologically active portions in which other regions of the protein are deleted, can be prepared by recombinant techniques and evaluated for one or more of the activities described herein. Preferably, the biologically active portions of a glutaredoxin or thioredoxin include one or more selected domains/motifs or portions thereof having biological activity.

In addition to fragments of the glutaredoxin or thioredoxin described herein, the present invention includes homologs and analogs of naturally occurring glutaredoxin or thioredoxin and glutaredoxin or thioredoxin encoding nucleic acids in a plant.

"Homologs" are defined herein as two nucleic acids or proteins that have similar, or "homologous", nucleotide or amino acid sequences, respectively. Homologs include allelic variants, orthologs, paralogs, agonists and antagonists of glutaredoxin or thioredoxin as defined hereafter. The term "homolog" further encompasses nucleic acid molecules that differ from one of the nucleotide sequences shown in SEQ IDs 1, 3, 5, 7, 9, 11, 13 of yeast and/or SEQ ID No. 15, 17, 19, 21, 23, 25, 27, 29, 31, 33, 35, 37, 39, 41, 43, 45, 47, 49 of plants (and portions thereof) due to degeneracy of the genetic code and thus encode the same glutaredoxin or thioredoxin as that encoded by the amino acid sequences shown in SEQ ID No. 2, 4, 6, 8, 10, 12, 14 of yeast and/or SEQ ID No. 16, 18, 20, 22, 24, 26, 28, 30, 32, 34, 36, 38, 40, 42, 44, 46, 48, 50 of plants. As used herein a "naturally occurring" glutaredoxin or thioredoxin refers to a glutaredoxin or thioredoxin amino acid sequence that occurs in nature.

Moreover, nucleic acid molecules encoding glutaredoxin or thioredoxin from the same or other species such as glutaredoxin or thioredoxin analogs, orthologs and paralogs, are intended to be within the scope of the present invention. As used herein, the term "analogs" refers to two nucleic acids that have the same or similar function, but that have evolved separately in unrelated organisms. As used herein, the term "orthologs" refers to two nucleic acids from different species that have evolved from a common ancestral gene by speciation. Normally, orthologs encode proteins having the same or similar functions. As also used herein, the term "paralogs" refers to two nucleic acids that are related by duplication within a genome. Paralogs usually have different functions, but these functions may be related (Tatusov, R. L. et al. 1997 Science 278(5338):631-637). Analogs, orthologs and paralogs of a naturally occurring glutaredoxin or thioredoxin can differ from the naturally occurring glutaredoxin or thioredoxin by post-translational modifications, by amino acid sequence differences, or by both. Post-translational modifications include in vivo and in vitro chemical derivatization of polypeptides, e.g., acetylation, carboxylation, phosphorylation, or glycosylation, and such modifications may occur during polypeptide synthesis or processing or following treatment with isolated modifying enzymes. In particular, orthologs of the invention will generally exhibit at least 80-85%, more preferably 90%, and most preferably 95%, 96%, 97%, 98% or even 99% identity or homology with all or part of a naturally occurring glutaredoxin or thioredoxin amino acid sequence and will exhibit a function similar to a glutaredoxin or thioredoxin. Orthologs of the present invention are also preferably capable of participating in the stress response in plants.

In addition to naturally-occurring variants of a glutaredoxin or thioredoxin sequence that may exist in the population, the skilled artisan will further appreciate that changes can be introduced by mutation into a nucleotide sequence of SEQ IDs 1, 3, 5, 7, 9, 11, 13 of yeast and/or SEQ ID No. 15, 17, 19, 21, 23, 25, 27, 29, 31, 33, 35, 37, 39, 41, 43, 45, 47, 49 of plants, thereby leading to changes in the amino acid sequence of the encoded glutaredoxin or thioredoxin, without altering the functional ability of the glutaredoxin or thioredoxin. For example, nucleotide substitutions leading to amino acid substitutions at "non-essential" amino acid residues can be made in a sequence of SEQ IDs 1, 3, 5, 7, 9, 11, 13 of yeast and/or SEQ ID No. 15, 17, 19, 21, 23, 25, 27, 29, 31, 33, 35, 37, 39, 41, 43, 45, 47, 49 of plants. A "non-essential" amino acid residue is a residue that can be altered from the wild-type sequence of one of the glutaredoxin or thioredoxin s without altering the activity of said glutaredoxin or thioredoxin, whereas an "essential" amino acid residue is required for glutaredoxin or thioredoxin activity. Other amino acid residues, however, (e.g., those that are not conserved or only semi-conserved in the domain having glutaredoxin or thioredoxin activity) may not be essential for activity and thus are likely to be amenable to alteration without altering glutaredoxin or thioredoxin activity.

Accordingly, another aspect of the invention pertains to nucleic acid molecules encoding glutaredoxin or thioredoxin that contain changes in amino acid residues that are not essential for glutaredoxin or thioredoxin activity. Such glutaredoxin or thioredoxin differ in amino acid sequence from a sequence comprising of SEQ IDs 2, 4, 6, 8, 10, 12, 14 of yeast and/or SEQ ID No. 16, 18, 20, 22, 24, 26, 28, 30, 32, 34, 36, 38, 40, 42, 44, 46, 48, 50 of plants, yet retain at least one of the glutaredoxin or thioredoxin activities described herein. In one embodiment, the isolated nucleic acid molecule comprises a nucleotide sequence encoding a protein, wherein the protein comprises an amino acid sequence at least about 50% homologous to an amino acid sequence of SEQ IDs 2, 4, 6, 8, 10, 12, 14 of yeast and/or SEQ ID No. 16, 18, 20, 22, 24, 26, 28, 30, 32, 34, 36, 38, 40, 42, 44, 46, 48, 50. Preferably, the protein encoded by the nucleic acid molecule is at least about 50-60% homologous to one of the sequences of SEQ ID No. 2, 4, 6, 8, 10, 12, 14 of yeast and/or SEQ ID No. 16, 18, 20, 22, 24, 26, 28, 30, 32, 34, 36, 38, 40, 42, 44, 46, 48, 50 of plants, more preferably at least about 60-70% homologous to one of the sequences of SEQ ID No. 2, 4, 6, 8, 10, 12, 14 of yeast and/or SEQ ID No. 16, 18, 20, 22, 24, 26, 28, 30, 32, 34, 36, 38, 40, 42, 44, 46, 48, 50 of plants, even more preferably at least about 70-80%, 80-90%, 90-95% homologous to one of the sequences of SEQ ID No. 2, 4, 6, 8, 10, 12, 14 of yeast and/or SEQ ID No. 16, 18, 20, 22, 24, 26, 28, 30, 32, 34, 36, 38, 40, 42, 44, 46, 48, 50 of plants, and most preferably at least about 96%, 97%, 98%, or 99% homologous to one of the sequences of SEQ IDs 2, 4, 6, 8, 10, 12, 14 of yeast and/or SEQ ID No. 16, 18, 20, 22, 24, 26, 28, 30, 32, 34, 36, 38, 40, 42, 44, 46, 48, 50 of plants. The preferred glutaredoxin or thioredoxin homologs of the present invention are preferably capable of participating in the stress tolerance response in a plant. The homology (=identity) was calculated over the entire amino acid range. The program used was PileUp (J. Mol. Evolution., 25 (1987), 351-360, Higgins et al., CABIOS, 5 1989: 151-153).

Variants shall also be encompassed, in particular, functional variants which can be obtained from the sequence shown in SEQ ID NO: 1, 3, 5, 7, 9, 11, 13 of yeast and/or SEQ ID No. 15, 17, 19, 21, 23, 25, 27, 29, 31, 33, 35, 37, 39, 41, 43, 45, 47, 49 of plants by means of deletion, insertion or substitution of nucleotides, the enzymatic activity of the derived synthetic proteins being retained.

An isolated nucleic acid molecule encoding a glutaredoxin or thioredoxin homologous to a protein sequence of SEQ IDs 2, 4, 6, 8, 10, 12, 14 of yeast and/or SEQ ID No. 16, 18, 20, 22, 24, 26, 28, 30, 32, 34, 36, 38, 40, 42, 44, 46, 48, 50 of plants can be created by introducing one or more nucleotide substitutions, additions or deletions into a nucleotide sequence of SEQ IDs 1, 3, 5, 7, 9, 11, 13 of yeast and/or SEQ ID No. 15, 17, 19, 21, 23, 25, 27, 29, 31, 33, 35, 37, 39, 41, 43, 45, 47, 49 of plants such that one or more amino acid substitutions, additions or deletions are introduced into the encoded protein. Mutations can be introduced into one of the sequences of SEQ IDs 1, 3, 5, 7, 9, 11, 13 of yeast and/or SEQ ID No. 15, 17, 19, 21, 23, 25, 27, 29, 31, 33, 35, 37, 39, 41, 43, 45, 47, 49 of plants by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a glutaredoxin or thioredoxin is preferably replaced with another amino acid residue from the same side chain family. Alternatively, in another embodiment, mutations can be introduced randomly along all or part of a glutaredoxin or thioredoxin coding sequence, such as by saturation mutagenesis, and the resultant mutants can be screened for a glutaredoxin or thioredoxin activity described herein to identify mutants that retain glutaredoxin or thioredoxin activity. Following mutagenesis of one of the sequences of SEQ IDs 1, 3, 5, 7, 9, 11, 13 of yeast and/or SEQ ID No. 15, 17, 19, 21, 23, 25, 27, 29, 31, 33, 35, 37, 39, 41, 43, 45, 47, 49 of plants, the encoded protein can be expressed recombinantly and the activity of the protein can be determined by analyzing the stress tolerance of a plant expressing the protein as described in Examples below.

In addition to the nucleic acid molecules encoding the glutaredoxin or thioredoxin described above, another aspect of the invention pertains to isolated nucleic acid molecules that are antisense thereto. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire glutaredoxin or thioredoxin coding strand, or to only a portion thereof. In one embodiment, an antisense nucleic acid molecule is antisense to a "coding region" of the coding strand of a nucleotide sequence encoding a glutaredoxin or thioredoxin. The term "coding region" refers to the region of the nucleotide sequence comprising codons that are translated into amino acid residues. In another embodiment, the antisense nucleic acid molecule is antisense to a "noncoding region" of the coding strand of a nucleotide sequence encoding a glutaredoxin or thioredoxin. The term "noncoding region" refers to 5' and 3' sequences that flank the coding region that are not translated into amino acids (i.e., also referred to as 5' and 3' untranslated regions).

In a preferred embodiment, an isolated nucleic acid molecule of the invention comprises a nucleic acid molecule which is a complement of one of the nucleotide sequences shown in SEQ IDs 1, 3, 5, 7, 9, 11, 13 of yeast and/or SEQ ID No. 15, 17, 19, 21, 23, 25, 27, 29, 31, 33, 35, 37, 39, 41, 43, 45, 47, 49 of plants, or a portion thereof. A nucleic acid molecule that is complementary to one of the nucleotide sequences shown in SEQ IDs 1, 3, 5, 7, 9, 11, 13 of yeast and/or SEQ ID No. 15, 17, 19, 21, 23, 25, 27, 29, 31, 33, 35, 37, 39, 41, 43, 45, 47, 49 of plants is one which is sufficiently complementary to one of the nucleotide sequences shown in SEQ IDs 3 or 7 such that it can hybridize to one of these nucleotide sequences, thereby forming a stable duplex.

Given the coding strand sequences encoding the glutaredoxin or thioredoxin disclosed herein (e.g., the sequences set forth in SEQ IDs 1, 3, 5, 7, 9, 11, 13 of yeast and/or SEQ ID No. 15, 17, 19, 21, 23, 25, 27, 29, 31, 33, 35, 37, 39, 41, 43, 45, 47, 49 of plants), antisense nucleic acids of the invention can be designed according to the rules of Watson and Crick base pairing. The antisense nucleic acid molecule can be complementary to the entire coding region of glutaredoxin or thioredoxin mRNA, but more preferably is an oligonucleotide which is antisense to only a portion of the coding or noncoding region of glutaredoxin or thioredoxin mRNA. For example, the antisense oligonucleotide can be complementary to the region surrounding the translation start site of glutaredoxin or thioredoxin mRNA. An antisense oligonucleotide can be, for example, about 5, 10, 15, 20, 25, 30, 35, 40, 45 or 50 or more nucleotides in length.

It is also possible to use the inverted repeat technology combining an antisense fragment with a portion of the antisense fragment in sense orientation linked by either an adapter sequence or an excisable intron (Abstract Book of the 6th Intern. Congr. Of Plant Mol. Biol. ISPMB, Quebec Jun. 18-24, 2000, Abstract No. S20-9 by Green et al.).

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylam inomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a cell or generated in situ such that they hybridize with or bind to cellular mRNA and/or genomic DNA encoding a glutaredoxin or thioredoxin to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., 1987 Nucleic Acids. Res. 15:6625-6641). The antisense nucleic acid molecule can also comprise a 2'-o-methylribonucleotide (Inoue et al., 1987 Nucleic Acids Res. 15:6131-6148) or a chimeric RNA-DNA analogue (Inoue et al., 1987 FEBS Lett. 215:327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes described in Haselhoff and Gerlach, 1988 Nature 334:585-591) can be used to catalytically cleave glutaredoxin or thioredoxin mRNA transcripts to thereby inhibit translation of glutaredoxin or thioredoxin mRNA. A ribozyme having specificity for a glutaredoxin or thioredoxin-encoding nucleic acid can be designed based upon the nucleotide sequence of a glutaredoxin or thioredoxin cDNA, as disclosed herein (i.e., SEQ IDs 1-76) or on the basis of a heterologous sequence to be isolated according to methods taught in this invention. For example, a derivative of a Tetrahymena L-19 IVS RNA can be constructed in which the nucleotide sequence of the active site is complementary to the nucleotide sequence to be cleaved in a glutaredoxin or thioredoxin-encoding mRNA. See, e.g., Cech et al. U.S. Pat. No. 4,987,071 and Cech et al. U.S. Pat. No. 5,116,742. Alternatively, glutaredoxin or thioredoxin mRNA can be used to select a catalytic RNA having a specific ribonuclease activity from a pool of RNA molecules. See, e.g., Bartel, D. and Szostak, J. W., 1993 Science 261:1411-1418.

Another embodiment of the invention is the regulating of the glutaredoxin or thioredoxin genes by means of double-stranded RNA ("double-stranded RNA interference"; dsRNAi) which has been described repeatedly for animal and plant organisms (for example Matzke M A et al. (2000) Plant Mol Biol 43:401-415; Fire A. et at (1998) Nature 391:806-811; WO 99/32619; WO 99/53050; WO 00/68374; WO 00/44914; WO 00/44895; WO 00/49035; WO 00/63364). Express reference is made to the processes and methods described in the above references. Such effective gene suppression can for example also be demonstrated upon transient expression or following transient transformation for example as the consequence of biolistic transformation (Schweizer P et al. (2000) Plant J 2000 24: 895-903). dsRNAi methods are based on the phenomenon that the simultaneous introduction of complementary strand and counterstrand of a gene transcript causes the expression of the gene in question to be suppressed in a highly efficient manner. The phenotype caused greatly resembles a corresponding knock-out mutant (Waterhouse P M et al. (1998) Proc Natl Acad Sci USA 95:13959-64).

As described, inter alia, in WO 99/32619, dsRNAi approaches are markedly superior to traditional antisense approaches.

The invention therefore furthermore relates to double-stranded RNA molecules (dsRNA molecules) which, upon introduction into a plant (or a cell, tissue, organ or seed derived therefrom), bring about the reduction of an glutaredoxin or thioredoxin gene. In the double-stranded RNA molecule for reducing the expression of an glutaredoxin or thioredoxin protein, a) one of the two RNA strands is essentially identical to at least a portion of an glutaredoxin or thioredoxin nucleic acid sequence, and b) the corresponding other RNA strand is essentially identical to at least a portion of the complementary strand of an glutaredoxin or thioredoxin nucleic acid sequence.

"Essentially identical" means that the dsRNA sequence can also show insertions, deletions or individual point mutations compared with the glutaredoxin or thioredoxin target sequence while still bringing about an effective reduction of the expression. The homology in accordance with the above definition preferably amounts to at least 75%, preferably at least 80%, very especially preferably at least 90%, most preferably 100%, between the sense strand of an inhibitory dsRNA and a part-segment of an glutaredoxin or thioredoxin nucleic acid sequence (or between the antisense strand and the complementary strand of an glutaredoxin or thioredoxin nucleic acid sequence). The length of the part-segment amounts to at least 10 bases, preferably at least 25 bases, especially preferably at least 50 bases, very especially preferably at least 100 bases, most preferably at least 200 bases or at least 300 bases. As an alternative, an "essentially identical" dsRNA can also be defined as a nucleic acid sequence which is capable of hybridizing with part of an glutaredoxin or thioredoxin gene transcript (for example in 400 mM NaCl, 40 mM PIPES pH 6.4, 1 mM EDTA at 505 C or 705 C for 12 to 16 h).

The dsRNA can be composed of one or more strands of polymerized ribonucleotides. Modifications both of the sugar-phosphate backbone and of the nucleosides may be present. For example, the phosphodiester bonds of the natural RNA can be modified in such a way that they comprise at least one nitrogen or sulfur hetero atom. Bases can be modified in such a way that the activity of, for example, adenosine deaminase is restricted.

The dsRNA can be generated enzymatically or fully or partially synthesized chemically.

The double-stranded structure can be formed starting from an individual self-complementary strand or starting from two complementary strands. In a single self-complementary strand, sense and antisense sequence may be linked by a linking sequence ("linker") and can form for example a hairpin structure. The linking sequence can preferably be an intron which is spliced out after the dsRNA has been synthesized. The nucleic acid sequence encoding a dsRNA can comprise further elements such as, for example, transcription termination signals or polyadenylation signals. If the two dsRNA strands are to be combined in a cell or plant, this can be effected in various ways:

a) transformation of the cell or plant with a vector comprising both expression cassettes, b) cotransformation of the cell or plant with two vectors, one of them comprising the expression cassettes with the sense strand and the other comprising the expression cassettes with the antisense strand, c) hybridizing two plants, each of which has been transformed with one vector, one of the vectors comprising the expression cassettes with the sense strand and the other comprising the expression cassettes with the antisense strand.

The formation of the RNA duplex can be initiated either outside or within the cell. Like in WO 99/53050, the dsRNA can also encompass a hairpin structure by linking sense and antisense strand by means of a linker (for example an intron). The self-complementary dsRNA structures are preferred since they only require the expression of one construct and always comprise the complementary strands in an equimolar ratio.

The expression cassettes encoding the antisense or sense strand of a dsRNA or the self-complementary strand of the dsRNA are preferably inserted into a vector and, using the methods described herein, stably inserted into the genome of a plant in order to ensure permanent expression of the dsRNA, using selection markers for example.

The dsRNA can be introduced using a quantity which allows at least one copy per cell. Greater quantities (for example at least 5, 10, 100, 500 or 1000 copies per cell) may bring about a more effective reduction.

As already described, 100% sequence identity between dsRNA and an glutaredoxin or thioredoxin gene transcript is not necessarily required in order to bring about an effective reduction of the glutaredoxin or thioredoxin expression. Accordingly, there is the advantage that the method is tolerant with regard to sequence deviations as may exist as the consequence of genetic mutations, polymorphisms or evolutionary divergence. Thus, for example, it is possible to use the dsRNA generated on the basis of the glutaredoxin or thioredoxin sequence of one organism to suppress the glutaredoxin or thioredoxin expression in another organism. The high sequence homology between the glutaredoxin or thioredoxin sequences from different sources allows the conclusion that this protein is conserved to a high degree within plants, so that the expression of a dsRNA derived from one of the disclosed glutaredoxin or thioredoxin sequences as shown in SEQ ID NO: 2, 4, 6, 8, 10, 12, 14 of yeast and/or SEQ ID No. 16, 18, 20, 22, 24, 26, 28, 30, 32, 34, 36, 38, 40, 42, 44, 46, 48, 50 of plants appears to have an advantageous effect in other plant species as well.

The dsRNA can be synthesized either in vivo or in vitro. To this end, a DNA sequence encoding a dsRNA can be brought into an expression cassette under the control of at least one genetic control element (such as, for example, promoter, enhancer, silencer, splice donor or splice acceptor or polyadenylation signal). Suitable advantageous constructions are described herein. Polyadenylation is not necessarily required, nor do elements for initiating translation have to be present.

A dsRNA can be synthesized chemically or enzymatically. Cellular RNA polymerases or bacteriophage RNA polymerases (such as, for example, T3, T7 or SP6 RNA polymerase) can be used for this purpose. Suitable methods for expression of RNA in vitro are described (WO 97/32016; U.S. Pat. No. 5,593,874; U.S. Pat. No. 5,698,425, U.S. Pat. No. 5,712,135, U.S. Pat. No. 5,789,214, U.S. Pat. No. 5,804,693). A dsRNA which has been synthesized in vitro chemically or enzymatically can be isolated completely or to some degree from the reaction mixture, for example by extraction, precipitation, electrophoresis, chromatography or combinations of these methods, before being introduced into a cell, tissue or organism. The dsRNA can be introduced directly into the cell or else be applied extracellularly (for example into the interstitial space).

However, it is preferred to transform the plant stably with an expression construct which brings about the expression of the dsRNA. Suitable methods are described herein. The methods of dsRNAi, cosuppression by means of sense RNA and "VIGS" ("virus induced gene silencing") are also termed "post-transcriptional gene silencing" (PTGS). PTGS methods, like the reduction of the glutaredoxin or thioredoxin function or activity with dominant-negative glutaredoxin or thioredoxin variants, are especially advantageous because the demands regarding the homology between the endogenous gene to be suppressed and the sense or dsRNA nucleic acid sequence expressed recombinantly (or between the endogenous gene and its dominant-negative variant) are lower than, for example, in the case of a traditional antisense approach. Such criteria with regard to homology are mentioned in the description of the dsRNAi method and can generally be applied to PTGS methods or dominant-negative approaches. Owing to the high degree of homology between the glutaredoxin or thioredoxin proteins from different sources, a high degree of conservation of this protein in plants can be assumed. Thus, using the glutaredoxin or thioredoxin nucleic acid sequences from yeast, it is presumably also possible efficiently to suppress the expression of homologous glutaredoxin or thioredoxin proteins in other species such as plants without the isolation and structure elucidation of the glutaredoxin or thioredoxin homologs occurring therein being required. Considerably less labor is therefore required.

All of the substances and compounds which directly or indirectly bring about a reduction in protein quantity, RNA quantity, gene activity or protein activity of an glutaredoxin or thioredoxin protein shall subsequently be combined in the term "anti-glutaredoxin or thioredoxin" compounds. The term "anti-glutaredoxin or thioredoxin" compound explicitly includes the nucleic acid sequences, peptides, proteins or other factors employed in the above-described methods.

For the purposes of the invention, "introduction" comprises all of the methods which are capable of directly or indirectly introducing an "anti-glutaredoxin or thioredoxin" compound into a plant or a cell, compartment, tissue, organ or seed thereof, or of generating such a compound there. Direct and indirect methods are encompassed. The introduction can lead to a transient presence of an "anti-glutaredoxin or thioredoxin" compound (for example a dsRNA) or else to its stable presence.

Alternatively, glutaredoxin or thioredoxin gene expression can be inhibited by targeting nucleotide sequences complementary to the regulatory region of a glutaredoxin or thioredoxin nucleotide sequence (e.g., a glutaredoxin or thioredoxin promoter and/or enhancer) to form triple helical structures that prevent transcription of a glutaredoxin or thioredoxin gene in target cells. See generally, Helene, C., 1991 Anticancer Drug Des. 6(6):569-84; Helene, C. et al., 1992 Ann. N.Y. Acad. Sci. 660:27-36; and Maher, L. J., 1992 Bioassays 14(12):807-15.

In particular, a useful method to ascertain the level of transcription of the gene (an indicator of the amount of mRNA available for translation to the gene product) is to perform a Northern blot (for reference see, for example, Ausubel et al., 1988 Current Protocols in Molecular Biology, Wiley: N.Y.). This information at least partially demonstrates the degree of transcription of the transformed gene. Total cellular RNA can be prepared from cells, tissues or organs by several methods, all well-known in the art, such as that described in Bormann, E. R. et al., 1992 Mol. Microbiol. 6:317-326. To assess the presence or relative quantity of protein translated from this mRNA, standard techniques, such as a Western blot, may be employed. These techniques are well known to one of ordinary skill in the art. (See, for example, Ausubel et al., 1988 Current Protocols in Molecular Biology, Wiley: N.Y.).

The invention further provides an isolated recombinant expression vector comprising a Oxidoreductase Stress-Related Protein, particularly glutaredoxin or thioredoxin nucleic acid as described above, wherein expression of the vector or glutaredoxin or thioredoxin nucleic acid, respectively in a host cell results in increased tolerance and/or resistance to environmental stress as compared to the wild type of the host cell. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

A plant expression cassette preferably contains regulatory sequences capable of driving gene expression in plant cells and operably linked so that each sequence can fulfill its function, for example, termination of transcription by polyadenylation signals. Preferred polyadenylation signals are those originating from *Agrobacterium tumefaciens* T-DNA such as the gene 3 known as octopine synthase of the Ti-plasmid pTiACH5 (Gielen et al., 1984 EMBO J. 3:835) or functional equivalents thereof but also all other terminators functionally active in plants are suitable.

As plant gene expression is very often not limited on transcriptional levels, a plant expression cassette preferably contains other operably linked sequences like translational enhancers such as the overdrive-sequence containing the 5"-untranslated leader sequence from tobacco mosaic virus enhancing the protein per RNA ratio (Gallie et al., 1987 Nucl. Acids Research 15:8693-8711).

Plant gene expression has to be operably linked to an appropriate promoter conferring gene expression in a timely, cell or tissue specific manner. Preferred are promoters driving constitutive expression (Benfey et al., 1989 EMBO J. 8:2195-2202) like those derived from plant viruses like the 35S CaMV (Franck et al., 1980 Cell 21:285-294), the 19S CaMV (see also U.S. Pat. No. 5,352,605 and PCT Application No. WO 8402913) or plant promoters like those from Rubisco small subunit described in U.S. Pat. No. 4,962,028.

Additional advantageous regulatory sequences are, for example, included in the plant promoters such as CaMV/35S [Franck et al., Cell 21 (1980) 285-294], PRP1 [Ward et al., Plant. Mol. Biol. 22 (1993)], SSU, OCS, lib4, usp, STLS1, B33, LEB4, nos or in the ubiquitin, napin or phaseolin promoter. Also advantageous in this connection are inducible promoters such as the promoters described in EP-A-0 388 186 (benzyl sulfonamide inducible), Plant J. 2, 1992: 397-404 (Gatz et al., Tetracyclin inducible), EP-A-0 335 528 (abscisic acid inducible) or WO 93/21334 (ethanol or cyclohexenol inducible). Additional useful plant promoters are the cytosolic FBPase promotor or ST-LSI promoter of the potato (Stockhaus et al., EMBO J. 8, 1989, 2445), the phosphorybosyl phyroshate amido transferase promoter of Glycine max (gene bank accession No. U87999) or the noden specific promoter described in EP-A-0 249 676. Additional particularly advantageous promoters are seed specific promoters which can be used for monokotyledones or dikotyledones are described in U.S. Pat. No. 5,608,152 (napin promoter from rapeseed), WO 98/45461 (phaseolin promoter from *Arobidopsis*), U.S. Pat. No. 5,504,200 (phaseolin promoter from *Phaseolus vulgaris*), WO 91/13980 (Bce4 promoter from *Brassica*), Baeumlein et al., Plant J., 2, 2, 1992: 233-239 (LEB4 promoter from leguminosa) said promoters are useful in dikotyledones. The following promoters are useful for example in monokotyledones Ipt-2- or Ipt-1-promoter from barley (WO 95/15389 and WO 95/23230), hordein promoter from barley and other useful promoters described in WO 99/16890.

It is possible in principle to use all natural promoters with their regulatory sequences like those mentioned above for the novel process. It is also possible and advantageous in addition to use synthetic promoters.

The gene construct may also comprise further genes which are to be inserted into the organisms and which are for example involved in stress resistance. It is possible and advantageous to insert and express in host organisms regulatory genes such as genes for inducers, repressors or enzymes which intervene by their enzymatic activity in the regulation, or one or more or all genes of a biosynthetic pathway. These genes can be heterologous or homologous in origin. The inserted genes may have their own promoter or else be under the control of same promoter as the sequences SEQ ID No. 1, 3, 5, 7, 9, 11, 13 of yeast and/or SEQ ID No. 15, 17, 19, 21, 23, 25, 27, 29, 31, 33, 35, 37, 39, 41, 43, 45, 47, 49 of plants or their homologs.

The gene construct advantageously comprises, for expression of the other genes present, additionally 3' and/or 5' terminal regulatory sequences to enhance expression, which are selected for optimal expression depending on the selected host organism and gene or genes.

These regulatory sequences are intended to make specific expression of the genes and protein expression possible as mentioned above. This may mean, depending on the host organism, for example that the gene is expressed or overexpressed only after induction, or that it is immediately expressed and/or overexpressed.

The regulatory sequences or factors may moreover preferably have a beneficial effect on expression of the introduced genes, and thus increase it. It is possible in this way for the regulatory elements to be enhanced advantageously at the transcription level by using strong transcription signals such as promoters and/or enhancers. However, in addition, it is also possible to enhance translation by, for example, improving the stability of the mRNA.

Other preferred sequences for use in plant gene expression cassettes are targeting-sequences necessary to direct the gene product in its appropriate cell compartment (for review see Kermode, 1996 Crit. Rev. Plant Sci. 15(4):285-423 and references cited therein) such as the vacuole, the nucleus, all types of plastids like amyloplasts, chloroplasts, chromoplasts, the extracellular space, mitochondria, the endoplasmic reticulum, oil bodies, peroxisomes and other compartments of plant cells.

Plant gene expression can also be facilitated via an inducible promoter (for review see Gatz, 1997 Annu. Rev. Plant Physiol. Plant Mol. Biol. 48:89-108). Chemically inducible promoters are especially suitable if gene expression is wanted to occur in a time specific manner.

Table 1 lists several examples of promoters that may be used to regulate transcription of the glutaredoxin or thioredoxin nucleic acid coding sequences.

TABLE 1

Examples of Tissue-specific and Stress inducible promoters in plants

| Expression | Reference |
|---|---|
| Cor78- Cold, drought, salt, ABA, wounding-inducible | Ishitani, et al., Plant Cell 9: 1935-1949 (1997). Yamaguchi-Shinozaki and Shinozaki, Plant Cell 6: 251-264 (1994). |
| Rci2A - Cold, dehydration-inducible | Capel et al., Plant Physiol 115: 569-576 (1997) |
| Rd22 - Drought, salt | Yamaguchi-Shinozaki and Shinozaki, Mol Gen Genet 238: 17-25 (1993). |
| Cor15A - Cold, dehydration, ABA | Baker et al., Plant Mol. Biol. 24: 701-713 (1994). |
| GH3- Auxin inducible | Liu et al., Plant Cell 6: 645-657 (1994) |
| ARSK1-Root, salt inducible | Hwang and Goodman, Plant J 8: 37-43 (1995). |
| PtxA - Root, salt inducible | GenBank accession X67427 |
| SbHRGP3 - Root specific | Ahn et al., Plant Cell 8: 1477-1490 (1998). |
| KST1 - Guard cell specific | Plesch et al., unpublished manuscript; Müller-Röber et al, EMBO J. 14: 2409-2416 (1995). |
| KAT1 - Guard cell specific | Plesch et al., Gene 249: 83-89 (2000) Nakamura et al., Plant Physiol. 109: 371-374 (1995) |
| salicylic acid inducible | PCT Application No. WO 95/19443 |
| tetracycline inducible | Gatz et al. Plant J. 2: 397-404 (1992) |
| Ethanol inducible | PCT Application No. WO 93/21334 |
| pathogen inducible PRP1 | Ward et al., 1993 Plant. Mol. Biol. 22: 361-366 |
| heat inducible hsp80 | U.S. Pat. No. 5,187,267 |
| cold inducible alpha-amylase | PCT Application No. WO 96/12814 |
| Wound-inducible pinII | European Patent No. 375091 |
| RD29A - salt-inducible | Yamaguchi-Shinozalei et al. (1993) Mol. Gen. Genet. 236: 331-340 |
| plastid-specific viral RNA-polymerase | PCT Application No. WO 95/16783 and. WO 97/06250 |

Other selection marker systems, like the AHAS marker or other promotors, e.g. superpromotor (Ni et al., Plant Journal 7, 1995: 661-676), Ubiquitin promotor (Callis et al., J. Biol. Chem., 1990, 265: 12486-12493; U.S. Pat. No. 5,510,474; U.S. Pat. No. 6,020,190; Kawalleck et al., Plant. Molecular Biology, 1993, 21: 673-684) or 34S promotor (GenBank Accession numbers M59930 and X16673) were similar useful for the instant invention and are known to a person skilled in the art.

The invention further provides a recombinant expression vector comprising a glutaredoxin or thioredoxin DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to a glutaredoxin or thioredoxin mRNA. Regulatory sequences operatively linked to a nucleic acid molecule cloned in the antisense orientation can be chosen which direct the continuous expression of the antisense RNA molecule in a variety of cell types. For instance, viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus wherein antisense nucleic acids are produced under the control of a high efficiency regulatory region. The activity of the regulatory region can be determined by the cell type into which the vector is introduced. For a discussion of the regulation of gene expression using antisense genes see Weintraub, H. et al., Antisense RNA as a molecular tool for genetic analysis, Reviews—Trends in Genetics, Vol. 1(1) 1986 and Mol et al., 1990 FEBS Letters 268:427-430.

Gene expression in plants is regulated by the interaction of protein transcription factors with specific nucleotide sequences within the regulatory region of a gene. A common type of transcription factor contains zinc finger (ZF) motifs. Each ZF module is approximately 30 amino acids long folded around a zinc ion. The DNA recognition domain of a ZF protein is a α-helical structure that inserts into the major grove of the DNA double helix. The module contains three amino acids that bind to the DNA with each amino acid contacting a single base pair in the target DNA sequence. ZF motifs are arranged in a modular repeating fashion to form a set of fingers that recognize a contiguous DNA sequence. For example, a three-fingered ZF motif will recognize 9 by of DNA. Hundreds of proteins have been shown to contain ZF motifs with between 2 and 37 ZF modules in each protein (Isalan M, et al., 1998 Biochemistry 37(35):12026-33; Moore M, et al., 2001 Proc. Natl. Acad. Sci. USA 98(4):1432-1436 and 1437-1441; U.S. Pat. No. 6,007,988 and U.S. Pat. No. 6,013,453).

The regulatory region of a plant gene contains many short DNA sequences (cis-acting elements) that serve as recognition domains for transcription factors, including ZF proteins. Similar recognition domains in different genes allow the coordinate expression of several genes encoding enzymes in a metabolic pathway by common transcription factors. Variation in the recognition domains among members of a gene family facilitates differences in gene expression within the same gene family, for example, among tissues and stages of development and in response to environmental conditions.

Typical ZF proteins contain not only a DNA recognition domain but also a functional domain that enables the ZF protein to activate or repress transcription of a specific gene. Experimentally, an activation domain has been used to activate transcription of the target gene (U.S. Pat. No. 5,789,538 and patent application WO9519431), but it is also possible to link a transcription repressor domain to the ZF and thereby inhibit transcription (patent applications WO00/47754 and WO2001002019). It has been reported that an enzymatic function such as nucleic acid cleavage can be linked to the ZF (patent application WO00/20622)

The invention provides a method that allows one skilled in the art to isolate the regulatory region of one or more Oxidoreductase Stress-Related Protein, particularly glutaredoxin or thioredoxin genes from the genome of a plant cell and to design zinc finger transcription factors linked to a functional domain that will interact with the regulatory region of the gene. The interaction of the zinc finger protein with the plant gene can be designed in such a manner as to alter expression of the gene and thereby confer increased or decreased tolerance of abiotic stress such as drought. The invention provides a method of producing a transgenic plant with a transgene encoding this designed transcription factor, or alternatively a natural transcription factor, that modifies transcription of the Oxidoreductase Stress-Related Protein, particularly glutaredoxin or thioredoxin gene to provide increased tolerance of environmental stress.

In particular, the invention provides a method of producing a transgenic plant with a Oxidoreductase Stress-Related Protein, particularly glutaredoxin or thioredoxin coding nucleic acid, wherein expression of the nucleic acid(s) in the plant results in increased tolerance to environmental stress as compared to a wild type plant comprising: (a) transforming a plant cell with an expression vector comprising a glutaredoxin or thioredoxin nucleic acid, and (b) generating from the plant cell a transgenic plant with an increased tolerance to environmental stress as compared to a wild type plant. For such plant transformation, binary vectors such as pBinAR can be used (Höfgen and Willmitzer, 1990 Plant Science 66:221-230). Moreover suitable binary vectors such as pBIN19, pBI101, pGPTV or pCambia are described in Hellens et al., Trends in Plant Science, 2000, 5: 446-451.

Construction of the binary vectors can be performed by ligation of the cDNA in sense or antisense orientation into the T-DNA. 5-prime to the cDNA a plant promoter activates transcription of the cDNA. A polyadenylation sequence is located 3-prime to the cDNA. Tissue-specific expression can be achieved by using a tissue specific promoter as listed above. Also, any other promoter element can be used. For constitutive expression within the whole plant, the CaMV 35S promoter can be used. The expressed protein can be targeted to a cellular compartment using a signal peptide, for example for plastids, mitochondria or endoplasmic reticulum (Kermode, 1996 Crit. Rev. Plant Sci. 4(15):285-423). The signal peptide is cloned 5-prime in frame to the cDNA to archive subcellular localization of the fusion protein. Additionally, promoters that are responsive to abiotic stresses can be used with, such as the *Arabidopsis* promoter RD29A. One skilled in the art will recognize that the promoter used should be operatively linked to the nucleic acid such that the promoter causes transcription of the nucleic acid which results in the synthesis of a mRNA which encodes a polypeptide. Alternatively, the RNA can be an antisense RNA for use in affecting subsequent expression of the same or another gene or genes.

Alternate methods of transfection include the direct transfer of DNA into developing flowers via electroporation or *Agrobacterium* mediated gene transfer. *Agrobacterium* mediated plant transformation can be performed using for example the GV3101(pMP90) (Koncz and Schell, 1986 Mol. Gen. Genet. 204:383-396) or LBA4404 (Ooms et al., Plasmid, 1982, 7: 15-29; Hoekema et al., Nature, 1983, 303: 179-180) *Agrobacterium tumefaciens* strain. Transformation can be performed by standard transformation and regeneration techniques (Deblaere et al., 1994 Nucl. Acids. Res. 13:4777-4788; Gelvin and Schilperoort, Plant Molecular Biology Manual, 2$^{nd}$ Ed.—Dordrecht: Kluwer Academic Publ., 1995.—in Sect., Ringbuc Zentrale Signatur: BT11-P ISBN 0-7923-2731-4; Glick, B R and Thompson, J E, Methods in Plant Molecular Biology and Biotechnology, Boca Raton: CRC Press, 1993.-360 S., ISBN 0-8493-5164-2). For example, rapeseed can be transformed via cotyledon or hypocotyl transformation (Moloney et al., 1989 Plant Cell Reports 8:238-242; De Block et al., 1989 Plant Physiol. 91:694-701). Use of antibiotics for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994 Plant Cell Report 13:282-285. Additionally, transformation of soybean can be performed using for example a technique described in European Patent No. 0424 047, U.S. Pat. No. 5,322,783, European Patent No. 0397 687, U.S. Pat. No. 5,376,543 or U.S. Pat. No. 5,169,770. Transformation of maize can be achieved by particle bombardment, polyethylene glycol mediated DNA uptake or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387 and a specific example of wheat transformation can be found in PCT Application No. WO 93/07256.

The Oxidoreductase Stress-Related Protein, particularly glutaredoxin or thioredoxin nucleic acid molecules of the invention have a variety of uses. Most importantly, the nucleic acid and amino acid sequences of the present invention can be used to transform plant cells or plants, thereby inducing tolerance to stresses such as drought, high salinity and cold. The present invention therefore provides a transgenic plant transformed by a Oxidoreductase Stress-Related Protein, particularly glutaredoxin or thioredoxin nucleic acid (coding or antisense), wherein expression of the nucleic acid sequence in the plant results in increased tolerance to environmental stress as compared to a wild type plant. The transgenic plant can be a monocot or a dicot or a gymnosperm plant. The invention further provides that the transgenic plant can be selected from maize, wheat, rye, oat, triticale, rice, barley, soybean, peanut, cotton, borage, sufflower, linseed, primrose, rapeseed, canola and turnip rape, manihot, pepper, sunflower, tagetes, solanaceous plant such as potato, tobacco, eggplant and tomato, *Vicia* species, pea, alfalfa, bushy plants such as coffee, cacao, tea, *Salix* species, trees such as oil palm, coconut, perennial grass, such as ryegrass and fescue, and forage crops, such as alfalfa and clover and *Arabidopsis thaliana*. Further the transgenic plant can be selected from spruce, pine or fir for example.

In particular, the present invention describes using the expression of Oxidoreductase Stress-Related Protein, particularly glutaredoxin or thioredoxin to engineer drought-tolerant, salt-tolerant and/or cold-tolerant plants. This strategy has herein been demonstrated for *Arabidopsis thaliana*, Ryegrass, Alfalfa, Rapeseed/Canola, Soybean, Corn and Wheat but its application is not restricted to these plants. Accordingly, the invention provides a transgenic plant containing a glutaredoxin or thioredoxin selected from SEQ IDs 1, 3, 5, 7, 9, 11, 13 of yeast and/or SEQ ID No. 15, 17, 19, 21, 23, 25, 27, 29, 31, 33, 35, 37, 39, 41, 43, 45, 47, 49 of plants, wherein the environmental stress is drought, increased salt or decreased or increased temperature but its application is not restricted to these adverse environments. Protection against other adverse conditions such as heat, air pollution, heavy metals and chemical toxicants, for example, may be obtained. In preferred embodiments, the environmental stress is drought.

The present invention also provides methods of modifying stress tolerance of a plant comprising, modifying the expression of a Oxidoreductase Stress-Related Protein, particularly glutaredoxin or thioredoxin in the plant. The invention provides that this method can be performed such that the stress tolerance is either increased or decreased. This can for example be done by the use of transcription factor or some type of site specific mutagenesis agent. In particular, the present invention provides methods of producing a transgenic plant having an increased tolerance to environmental stress as compared to a wild type plant comprising increasing expression of a Oxidoreductase Stress-Related Protein, particularly glutaredoxin or thioredoxin in a plant.

The Oxidoreductase Stress-Related Protein, particularly glutaredoxin or thioredoxin encoding nucleic acids of the present invention have utility as (Quantitative Trait Locus) QTL markers for mapping genetic loci associated with environmental stress tolerance. As such, the sequences have utility in the identification of plants that exhibit an environmental stress tolerance phenotype from those that do not within a segregating population of plants. For example, to identify the region of the genome to which a particular glutaredoxin or thioredoxin nucleic acid sequence binds, genomic DNA could be digested with one or more restriction enzymes, and the fragments incubated with the glutaredoxin or thioredoxin nucleic acid, preferably with readily detectable labels. Binding of such a nucleic acid molecule to the genome fragment enables the localization of the fragment to the genome map and, when performed multiple times with different enzymes, facilitates a unique identifying pattern. Further, the nucleic acid molecules of the invention may be sufficiently homologous to the sequences of related species such that these nucleic acid molecules may serve as markers for the construction of a genomic map.

The genetics of quantitative traits associated to DNA markers has been used extensively in plant breeding for more than a decade (Tansgley et al., 1989 Biotechnology 7:257-264). The principle consists of using segregating lines derived from two homozygous parents and mapping these progeny with markers to link each marker to at least another one (saturated map), after which a statistical relationship between the quantitative trait value and the genotype at each marker is determined. A significant link of a locus to the trait means that at least one gene that in the vicinity of the marker contributes part of the phenotype variability. By definition, this locus is called a quantitative trait locus (QTL). In such a case, the gene becomes a candidate gene for explaining part of the observed phenotype and methods to identify and clone these genes have been described (Yano M, 2001. Current Opinion in Plant Biology 4:130-135). An observed correlation between a QTL and a gene location is likely to be causal, and therefore much more informative than a physiological correlation. This approach was applied to biochemical traits related to carbohydrate metabolism in maize leaves (Causse M., et al., 1995. Molecular Breeding 1:259-272).

This invention uses an alternative approach to the classical method. The approach of this invention is to use the QTL methodology linking a gene or locus known to be associated with the phenotype as a screening method. The marker may be associated with either the DNA sequences or the expression level of the gene, e.g. quantity of a specific mRNA molecule. In this instance, the marker serves as a convenient genetic means to identify individuals with the stress tolerance phenotype within a population of individuals that lack the phenotype. This method has utility when the phenotype is often difficult or expensive to detect or quantitative.

Many traits including tolerance of environmental stress and yield are associated with multiple genes and are therefore considered quantitative traits. This means that more than one marker or genetic locus is associated with the phenotype. In many instances, it is necessary to stack the various loci related to a phenotype. This is accomplished in standard plant breeding methods by cross-pollinating two parents with different loci (markers) contributing to the phenotype and selecting those progeny that have both markers. This process or breeding and selecting can be repeated multiple times to combine all loci into one progeny.

This invention provides markers of specific genetic loci that are associated with tolerance of abiotic environmental stress. The DNA sequences in SEQ IDs 1, 3, 5, 7, 9, 11, 13 of yeast and/or SEQ ID No. 15, 17, 19, 21, 23, 25, 27, 29, 31, 33, 35, 37, 39, 41, 43, 45, 47, 49 of plants may be used in the identification and selection of stress tolerant plants. These plants, their seeds and varieties derived from them would not contain transgenes but would contain alleles or genetic loci representing natural genetic diversity and thereby exhibit increased tolerance of abiotic environmental stress.

Growing the modified plant under less than suitable conditions and then analyzing the growth characteristics and/or metabolism can assess the effect of the genetic modification in plants on stress tolerance. Such analysis techniques are well known to one skilled in the art, and include dry weight, wet weight, protein synthesis, carbohydrate synthesis, lipid synthesis, evapotranspiration rates, general plant and/or crop yield, flowering, reproduction, seed setting, root growth, respiration rates, photosynthesis rates, etc. (Applications of HPLC in Biochemistry in: Laboratory Techniques in Biochemistry and Molecular Biology, vol. 17; Rehm et al., 1993 Biotechnology, vol. 3, Chapter III: Product recovery and purification, page 469-714, VCH: Weinheim; Better, P. A. et al., 1988 Bioseparations: downstream processing for biotechnology, John Wiley and Sons; Kennedy, J. F. and Cabral, J. M. S., 1992 Recovery processes for biological materials, John Wiley and Sons; Shaeiwitz, J. A. and Henry, J. D., 1988 Biochemical separations, in: Ulmann's Encyclopedia of Industrial Chemistry, vol. B3, Chapter 11, page 1-27, VCH: Weinheim; and Dechow, F. J. (1989) Separation and purification techniques in biotechnology, Noyes Publications).

The engineering of one or more Oxidoreductase Stress-Related Protein, particularly glutaredoxin or thioredoxin genes of the invention may also result in Oxidoreductase Stress-Related Protein, particularly glutaredoxin or thioredoxin proteins having altered activities which indirectly impact the stress response and/or stress tolerance of plants. For example, the normal biochemical processes of metabolism result in the production of a variety of products (e.g., hydrogen peroxide and other reactive oxygen species) which may actively interfere with these same metabolic processes (for example, peroxynitrite is known to react with tyrosine side chains, thereby inactivating some enzymes having tyrosine in the active site (Groves, J. T., 1999 Curr. Opin. Chem. Biol. 3(2):226-235). By optimizing the activity of one or more Oxidoreductase Stress-Related Protein, particularly glutaredoxin or thioredoxin enzymes of the invention, it may be possible to improve the stress tolerance of the cell.

Additionally, the sequences disclosed herein, or fragments thereof, can be used to generate knockout mutations in the genomes of various plant cells (Girke, T., 1998 The Plant Journal 15:39-48). The resultant knockout cells can then be evaluated for their ability or capacity to tolerate various stress conditions, their response to various stress conditions, and the effect on the phenotype and/or genotype of the mutation. For other methods of gene inactivation see U.S. Pat. No. 6,004, 804 "Non-Chimeric Mutational Vectors" and Puttaraju et al., 1999 Spliceosome-mediated RNA trans-splicing as a tool for gene therapy Nature Biotechnology 17:246-252.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

The invention also pertains the use of ORSRP encoding nucleic acid selected form the group comprising SEQ ID No.

SEQ ID No. 1, 3, 5, 7, 9, 11, 13 of yeast and/or SEQ ID No. 15, 17, 19, 21, 23, 25, 27, 29, 31, 33, 35, 37, 39, 41, 43, 45, 47, 49 of plants and/or homologs thereof for preparing a plant cell with increased environmental stress tolerance. The said sequences can also be used for preparing a plant with increased environmental stress tolerance. Object of the invention is further the use of ORSRP encoding nucleic acid selected form the group comprising SEQ ID No. SEQ ID No. 1, 3, 5, 7, 9, 11, 13 of yeast and/or SEQ ID No. 15, 17, 19, 21, 23, 25, 27, 29, 31, 33, 35, 37, 39, 41, 43, 45, 47, 49 of plants and/or homologs thereof or parts thereof as DNA markers for selection of plants with increased tolerance to environmental stress. The said ORSRP encoding nucleic acid selected from the group comprising of SEQ ID No. SEQ ID No. 1, 3, 5, 7, 9, 11, 13 of yeast and/or SEQ ID No. 15, 17, 19, 21, 23, 25, 27, 29, 31, 33, 35, 37, 39, 41, 43, 45, 47, 49 of plants and/or homologs thereof or parts thereof can also be used as Quantitative Trait Locus (QTL) markers for mapping genetic loci associated with environmental stress tolerance.

EXAMPLE 1

Engineering Stress-Tolerant *Arabidopsis* Plants by Over-Expressing Glutaredoxin or Thioredoxin Genes Gene Cloning and Transformation of *Arabidopsis thaliana*
Amplification The standard protocol of Pfu DNA polymerase or a PfuI Taq DNA polymerase mix was used for the amplification procedure. Amplified ORF fragments were analysed by gel electrophoresis. Each primer consists of a universal 5 'end and ORF specific 3' end whereby the universal sequences differ for the forward and reverse primers (forward primer sequence contains a EcoRI and the reverse primer sequence a SmaI restriction site) allowing a unidirectional cloning success. Amplification using the protocol of Pfu or Herculase DNA polymerase (Stratagene). Conditions: 1×PCR buffer [20 mM Tris-HCl (pH 8.8), 2 mM MgSO$_4$, 10 mM KCl, 10 mM (NH$_4$)SO$_4$, 0.1% Triton X-100, 0.1 mg/ml BSA], 100 ng genomic DNA *Saccharomyces cerevisae* (S288C), 50 pmol forward primer, 50 pmol reverse primer, 2.5 u Pfu or Herculase DNA polymerase. 1st cycle for 3' at 94° C., followed by 25 cycles for 30" at 94° C., 30" 55° C. and 5-6' 72° C., followed by 1 cycle for 6-10' at 72° C., final for 4° C. at ∞.

```
YDR513w primer forward:
                                    (SEQ ID NO: 51)
GGAATTCCAGCTGACCACCATGGAGACCAATTTTTCCTTCGACT YDR513w primer reverse:
                                    (SEQ ID NO: 52)
GATCCCCGGGAATTGCCATGCTATTGAAATACCGGCTTCAATATTT YER174c primer forward:
                                    (SEQ ID NO: 53)
GGAATTCCAGCTGACCACCATGACTGTGGTTGAAATAAAAAGCC YER174c primer reverse:
                                    (SEQ ID NO: 54)
GATCCCCGGGAATTGCCATGTTACTGTAGAGCATGTTGGAAATATT
```

Vector Preparation.

The preferred binary vector 1bxbigResgen, which is based on the modified pPZP binary vector backbone (comprising the kanamycin-gene for bacterial selection; Hajukiewicz, P. et al., 1994, plant Mol. Biol., 25: 989-994) carried the selection marker bar-gene (De Block et al., 1987, EMBO J. 6, 2513-2518) driven by the mas1'promoter (Velten et al., 1984, EMBO J. 3, 2723-2730; Mengiste, Amedeo and Paszkowski, 1997, Plant J., 12, 945-948) on its T-DNA. In addition the T-DNA contained the strong double 35S promotor (Kay et al., 1987, Science 236, 1299-1302) in front of a cloning cassette followed by the nos-terminator (Depicker A. Stachel S. Dhaese P. Zambryski P. Goodman H M. Nopaline synthase: transcript mapping and DNA sequence. Journal of Molecular & Applied Genetics. 1(6):561-73, 1982). The cloning cassette consists of the following sequence:

```
                                    (SEQ ID NO: 55)
5'-GGAATTCCAGCTGACCACCATGGCAATTCCCGGGGATC-3'
```

Other selection marker systems, like the AHAS marker or other promotors, e.g. superpromoter (Ni-Min et al., Plant Journal, 1995, 7(4): 661-676), Ubiquitin promotor (Callis et al., J. Biol. Chem., 1990, 265: 12486-12493; U.S. Pat. No. 5,510,474; U.S. Pat. No. 6,020,190; Kawalleck et al., Plant. Molecular Biology, 1993, 21: 673-684) or 34S promotor (GenBank Accession numbers M59930 and X16673) were similar useful for the instant invention and are known to a person skilled in the art. The vector was linearised with EcoRI and SmaI using the standard protocol provided by the supplier (MBI Fermentas, Germany) and purified using Qiagen columns (Qiagen, Hilden, Germany).

Ligation and Transformation

Present ORF fragments (~100 ng) were digested by EcoRI and SmaI using the standard protocol provided by the supplier (MBI Fermentas, Germany), purified using Qiagen columns (Qiagen, Hilden, Germany) and were ligated into the cloning cassette of the binary vector systems (~30 ng) using standard procedures (Maniatis et al.).

Ligation products were transformed into *E. coli* (DH5alpha) using a standard heat shock protocol (Maniatis et al.). Transformed colonies were grown on LB media and selected by respective antibiotica (Km) for 16 h at 37° C. ÜN.

Plasmidpreparation

Plasmids were prepared using standard protocol (Qiagen Hilden, Germany).

Transformation of Agrobacteria

Plasmids were transformed into *Agrobacterium tumefaciens* (GV3101pMP90; Koncz and Schell, 1986 Mol. Gen. Genet. 204:383-396) using heat shock or electroporation protocols. Transformed colonies were grown on YEP media and selected by respective antibiotika (Rif/Gent/Km) for 2 d at 28° C. ÜN. These agrobacteria cultures were used for the plant transformation.

*Arabidopsis thaliana* was grown and transformed according to standard conditions (Bechtold 1993 (Bechtold, N., Ellis, J., Pelletier, G. 1993. *In planta Agrobacterium* mediated gene transfer by infiltration of *Arabidopsis thaliana* plants C. R. Acad. Sci. Paris. 316:1194-1199); Bent et al. 1994 (Bent, A., Kunkel, B. N., Dahlbeck, D., Brown, K. L., Schmidt, R., Giraudat, J., Leung, J., and Staskawicz, B. J. 1994; PPCS2 of *Arabidopsis thaliana*: A leucin-rich repeat class of plant disease resistant genes; Science 265:1856-1860).

Transgenic *A. thaliana* plants were grown individually in pots containing a 4:1 (v/v) mixture of soil and quartz sand in a York growth chamber. Standard growth conditions were: photoperiod of 16 h light and 8 h dark, 20° C., 60% relative humidity, and a photon flux density of 150 µE. To induce germination, sown seeds were kept at 4° C., in the dark, for 3 days. Plants were watered daily until they were approximately 3 weeks old at which time drought was imposed by withholding water. Coincidentally, the relative humidity was reduced in 10% increments every second day to 20%. After approximately 12 days of withholding water, most plants showed visual symptoms of injury, such as wilting and leaf browning, whereas tolerant plants were identified as being visually turgid and healthy green in color. Plants were scored for symptoms of drought injury in comparison to neighbouring plants for 3 days in succession.

Three successive experiments were conducted. In the first experiment, 10 independent T2 lines were sown for each gene being tested. The percentage of plants not showing visual symptoms of injury was determined. In the second experiment, the lines that had been scored as tolerant in the first experiment were put through a confirmation screen according to the same experimental procedures. In this experiment, 10 plants of each tolerant line were grown and treated as before. In the third experiment, at least 5 replicates of the most tolerant line were grown and treated as before. The average and maximum number of days of drought survival after wild-type control had visually died and the percentage tolerant plants was determined. Additionally measurements of chlorophyll fluorescence were made in stressed and non-stressed plants using a Mini-PAM (Heinz Walz GmbH, Effeltrich, Germany).

In the first experiment, after 12 days of drought, the control, non-transgenic *Arabidopsis thaliana* and most transgenic lines expressing other transgenes in the test showed extreme visual symptoms of stress including necrosis and cell death. Several plants expressing the YER174C (=ORF737; SEQ ID No. 7) gene and the YDR513W (=ORF809; SEQ ID No. 3) gene retained viability as shown by their turgid appearance and maintenance of green color. Several independent transgenic lines, in the case of both the YER174C and the YDR513W genes, did not become necrotic for at least 3 days after the control plants had died (Table 2 and 3).

The second experiment compared a smaller number of independent transgenic lines for each gene but a greater number of progeny within each independent transformation event. This experiment confirmed the previous results. Those lines containing the YER174C gene (Table 2) did not become necrotic for 1-2 days after the controls and in the case of the YDR513W gene, 2-3 days after the controls (Table 3).

TABLE 2

Drought tolerance of transgenic *Arabidopsis thaliana* expressing the YER174C gene after imposition of drought stress on 3 week old plants. Control plants showed extensive visual symptoms of injury on day 12 and were considered dead.

| | | Percent survival | | |
|---|---|---|---|---|
| Experiment | Plant | Day 13 | Day 14 | Day 15 |
| 1 | Control | 0 | 0 | 0 |
|   | Transgenic 737 | 60 | 40 | 20 |
| 2 | Control | 0 | 0 | 0 |
|   | Transgenic 737-1 | 22 | 22 | 0 |
|   | Transgenic 737-3 | 50 | 0 | 0 |

TABLE 3

Drought tolerance of transgenic *Arabidopsis thaliana* expressing the YDR513W gene after imposition of drought stress on 3 week old plants. Control plants showed extensive visual symptoms of injury on day 12 and were considered dead.

| | | Percent survival | | |
|---|---|---|---|---|
| Experiment | Plant | Day 13 | Day 14 | Day 15 |
| 1 | Control | 0 | 0 | 0 |
|   | Transgenic 809 | 50 | 33 | 33 |

TABLE 3-continued

Drought tolerance of transgenic *Arabidopsis thaliana* expressing the YDR513W gene after imposition of drought stress on 3 week old plants. Control plants showed extensive visual symptoms of injury on day 12 and were considered dead.

| | | Percent survival | | |
|---|---|---|---|---|
| Experiment | Plant | Day 13 | Day 14 | Day 15 |
| 2 | Control | 0 | 0 | 0 |
|   | Transgenic 809-5 | 25 | 13 | 13 |
|   | Transgenic 809-8 | 50 | 25 | 0 |

In the third experiment, one transgenic line from each gene was tested using a even larger number of plants. In line 737-3 expressing the YER174C gene, necrosis did not occur on average until 1.1 days after the controls and 2 of the 22 plants tested did not show necrosis until 4 days later (Table 4). Similarly, line 809-8 expressing the YDR513W gene survived on average 3.1 days longer than the control and 1 plant survived for 6 days longer later (Table 4). Other independent transgenic lines for both genes showed greater survival than the non-transgenic plants in this experiment.

Chlorophyll fluorescence measurements of photosynthetic yield confirmed that 12 days of drought stress completely inhibited photosynthesis in the control plants, but the transgenic line 809-8 maintained its photosynthetic function longer (Table 5).

TABLE 4

Relative drought tolerance of *Arabidopsis thaliana* transgenic line 737-3 expressing the YER174C gene and line 809-8 expressing the YDR513W gene after imposition of drought stress on 3 week old plants in comparison to non-transgenic control plants. Control plants showed extensive visual symptoms of injury on day 12 and were considered dead.

| | 737-3 | 809-8 |
|---|---|---|
| Number of plants tested | 22 | 7 |
| Duration of survival after control (days) | 1.1 | 3.1 |
| Maximal duration of survival (number of plants) | 3 (2) | 6 (1) |

TABLE 5

Effect of drought stress on photosynthetic yield as determined by chlorophyll fluorescence (± std deviation) of *Arabidopsis thaliana* control and transgenic line 809-8 expressing the YDR513W gene.

| Days of drought | Control | Transgenic line 809-8 |
|---|---|---|
| 0 | 765 ± 29 | 723 ± 29 |
| 5 | 794 ± 36 | 781 ± 25 |
| 10 | 412 ± 194 | 660 ± 121 |
| 12 | 54 ± 83 | 411 ± 305 |

EXAMPLE 2

Isolation and Characterization of Plant Glutaredoxin Genes

ORF 737 and 809 correspond to yeast, *Saccharomyces cerevisiae*, genes for glutaredoxin4 (GRX4) and glutaredoxin2 (GRX2), respectively, that contain a pair of cysteine amino acids at the putative active site of the protein (Grant C M. 2000. Molecular Microbiology 39: 533-541; Grant C M et al., 2001. Biochimica et Biophysica Acta—Gene Structure & Expression 1490: 33-42). Grx3, Grx4, and Grx5 is a subfamily of yeast glutaredoxins that contain a single cysteine residue at the putative active site (Rodriguez-Manzaneque et al., 1999. Molecular & Cellular Biology 19: 8180-8190). *Saccharomyces cerevisiae* also contains two gene pairs for thioredoxins (TRX1, TRX2) (Draculic et al., 2000. Molecular Microbiology 36: 1167-1174). These gene sequences are listed in GenBank under the accession numbers listed in Table 6.

The sequence of GRX2 and GRX4 was used to identify related gene sequences in *Arabidopsis thaliana* by Blast analysis (Altschul S F, Gish W, Miller W, Myers E W, Lipman D J. 1990 J Mol Biol 215(3):403-10). The results identified related sequences with E<$10^{-10}$ as shown in Table 6, where E is defined as the expectancy value, or the statistical probability that the sequence appears in the database at random. A similar analysis was done on a three libraries of expressed sequence tags (ESTs) from *Brassica napus* cv. "AC Excel", "Quantum" and "Cresor" (canola) and *Oryza sativa* cv. Nippon-Barre (a japonica rice). The search identified several *Brassica* and rice glutaredoxin cDNA sequences with E<$10^{-10}$ (Table 6).

The yeast and plant cDNA sequences were translated into a predicted amino acid sequences and the relationship among the amino acid sequences was determined by sequence alignment and block alignment using the ClustalW algorithm in Vector NTI ver7. The glutaredoxin and thioredoxin genes were separated into four subfamilies based on this alignment as shown in FIG. 1. The glutaredoxin family is characterized by the standard glutaredoxin domain defined in the Prosite database as an amino acid motif with the consensus sequence [LIVMD]-[FYSA]-x(4)-C-[PV]-[FYWH]-C-x(2)-[TAV]-x(2,3)-[LIV] [LIVMD]-[FYSA]-x(4)-C-[PV]-[FYWH]-C-x(2)-[TAV]-XX-[LIV] (SEQ ID NO:56) or [LIVMD]-[FYSA]-x(4)-C-[PV]-[FYWH]-C-x(2)-[TAV]-XXX-[LIV] (SEQ ID NO:57). Most sequences show the characteristic two cysteines that when reduced form either two thiol groups or when oxidized form a disulfide bond. Other proteins in this family have only a single C at this site.

Subfamily 1 contains the yeast genes GRX1 and GRX2 (FIGS. 2-4). Domain 1 has the core sequence [VI]-[VF]-[VI]-X-[SA]-K-[TS]-[WY]-C-[PGS]-[YF]-[CS] (SEQ ID NO: 58). OZ1116C26232 and AtQ95K75 lack the C-X-X-C disulfide site and instead have a single C at this site. Domain 2 contains a motif defined as G-Q-X-T-V-P-N-[VI]-[FY]-[VI]-X-G-[KN]-H-I-G-G-[CN] (SEQ ID NO: 59).

Figures 5, 6:
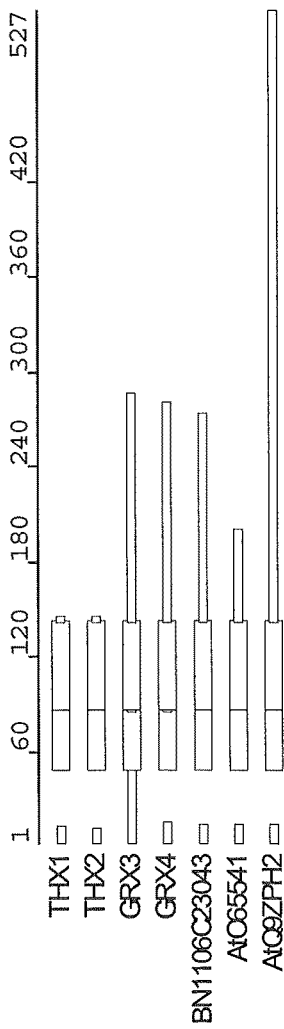
FIG. 5: Amino acid alignments of yeast and plant cDNA sequences of glutaredoxin subfamily 2 showing the presence of two conserved domains. The abbreviations correspond to the "Gene ID" as explained in Table 6.
FIG. 6: Amino acid alignment of glutaredoxin subfamily 2 domain 1 across yeast and plant cDNA sequences (THX1, SEQ ID NO: 12; THX2, SEQ ID NO: 14, GRX3, SEQ ID NO: 6; GRX4, SEQ ID NO: 8; BN1106C23043, SEQ ID NO: 24; AtQ65541, SEQ ID NO: 42; AtQ9ZPH2, SEQ ID NO: 44). The amino acid position at the start of the alignment is shown in parenthesis.

Subfamily 2 contains both glutaredoxin GRX3 and GRX4 and thioredoxin THX1 and THX2 sequences (FIGS. 5-7). This family has a region of homology comprising two domains. In most sequences the domains are continuous, except in GRX3 and GRX4 in which the two domains are separated by two amino acids. Domain 1 has a core sequence of [VI]V-[VL]-X-F-X-[TA]-X-W-[CA]-X-[PA]-[CS]-K (SEQ ID NO: 60). The region [CA]-X(2)-[CS] (SEQ ID NO: 61) contains C at position 1 or 4 or both. Domain 2 is a region of similarity that has a core sequence of F-X(2)-[VI]-[ED]-[AV]-[ED]-E-X(2)-[ED]-[IV] (SEQ ID NO: 62).

Subfamily 3 contains GRX5 and three plant sequences that have a single C amino acid at the putative active site (FIGS. 8-11). The core sequence of domain 1 is V-[VM]-X(3)-K-G-X(4)-P-X-C-G-F-S (SEQ ID NO: 63). Domain 2 is defined by the sequence Q-[LI]-[FY]-[VI]-X-[GK]-E-[FL]-X-G-G-[CS]-D-[IV] (SEQ ID NO: 64).

Subfamily 4 does not have any members from yeast and is comprised of 5 plant sequences that have two domains of homology (FIGS. 11-13). Domain 1 has a core sequence similar to subfamily 1 that is [VI]-V-I-F-S-K-S-Y-C-P-Y-C (SEQ ID NO: 65). Domain 2 has two regions with common sequences of V-V-E-L-D-X-R-E-D-G (SEQ ID NO: 66) and V-G-R-R-T-V-P-Q-V-F-[VI]-[NH]-G-K-H-[LI]-G-G-S-D-D (SEQ ID NO: 67).

A representative of each subfamily was selected and the full length coding sequence was ligated into a plant transformation vector using standard molecular biology techniques as described in Example 1. The coding sequence was inserted at the 3' end of a constitutive promoter to control expression in plants. The vector was transferred to *Agrobacterium tumefaciens* and this strain was used to transform *Arabidopsis thaliana* as described in Example 1. Transgenic plants were grown and treated with drought stress as described in Example 1. Those plants that contained the glutaredoxin/thioredoxin transgene from subfamilies 1, 2 and 3 were more tolerant of the drought treatment than the control, non-transgenic plants.

TABLE 6

Summary of yeast and plant glutaredoxin coding sequences.

| source | Sub Family | query | Gene ID | GenBank Accession | Nucleotide SEQ ID No. | Amino Acid SEQ ID No. |
|---|---|---|---|---|---|---|
| Yeast | 1 | | GRX1 | X59720 | 1 | 2 |
| | 1 | 809 | GRX2 | U18922 | 3 | 4 |
| | 2 | | GRX3 | Z47746 | 5 | 6 |
| | 2 | 737 | GRX4 | U33057 | 7 | 8 |
| | 3 | | GRX5 | U39205 | 9 | 10 |
| | 2 | | THX1 | M59168 | 11 | 12 |
| | 2 | | THX2 | M59169 | 13 | 14 |
| *Brassica* | 1 | 809 | BN1106C12219 | NA | 15 | 16 |
| | 4 | 809 | BN1106C21909 | NA | 17 | 18 |
| | 1 | 809 | BN1106C2202 | NA | 19 | 20 |
| | 4 | 809 | BN1106C2582 | NA | 21 | 22 |
| | 2 | 737 | BN1106C23043 | NA | 23 | 24 |
| *Arabidopsis* | 1 | 809 | AtQ9FM49 | AB009051 | 25 | 26 |
| | 1 | 809 | AtQ9FNE2 | AB006702 | 27 | 28 |
| | 4 | 809 | AtQ9FVX1 | NM_106386 | 29 | 30 |
| | 4 | 809 | AtQ9M457 | ATH271472 | 31 | 32 |
| | 1 | 809 | AtQ9SK75 | AY094445 | 33 | 34 |
| | 3 | 737 | AtQ9LW13 | AY087154 | 35 | 36 |
| | 3 | 737 | AtQ9SV38 | AY078020 | 37 | 38 |
| | 3 | 737 | AtO80451 | AY086273 | 39 | 40 |
| | 2 | 737 | AtO65541 | NM_119410 | 41 | 42 |
| | 2 | 737 | AtQ9ZPH2 | AY058202 | 43 | 44 |

TABLE 6-continued

Summary of yeast and plant glutaredoxin coding sequences.

| source | Sub Family | query | Gene ID | GenBank Accession | Nucleotide SEQ ID No. | Amino Acid SEQ ID No. |
|---|---|---|---|---|---|---|
| Rice | 4 | 809 | OZ1116 C12744 | NA | 45 | 46 |
|  | 1 | 809 | OZ1116 C2194 | X77150 | 47 | 48 |
|  | 1 | 809 | OZ1116 C26232 | NA | 49 | 50 |

Query specifies the ORF sequence used for the Blast search
NA—not available; sequence is not in a GenBank database

EXAMPLE 3

Engineering Stress-Tolerant *Arabidopsis* Plants by Over-Expressing Glutaredoxin or Thioredoxin Genes Using Stress-Inducible and Tissue-Specific Promoters Transgenic *Arabidopsis* plants were created as in example 1 to express the glutaredoxin and thioredoxin transgenes under the control of either a tissue-specific or stress-inducible promoter. Constitutive expression of a transgene may cause deleterious side effects. Stress inducible expression was achieved using promoters selected from those listed above in Table 1.

T2 generation plants were produced and treated with drought stress in two experiments. For the first drought experiment, the plants were deprived of water until the plant and soil were desiccated. At various times after withholding water, a normal watering schedule was resumed and the plants were grown to maturity. Seed yield was determined as g seeds per plant. At an equivalent degree of drought stress, tolerant plants were able to resume normal growth and produced more seeds than non-transgenic control plants. Proline content of the leaves and stomatal aperture were also measured at various times during the drought stress. Tolerant plants maintained a lower proline content and a greater stomatal aperture than the non-transgenic control plants.

An alternative method to impose water stress on the transgenic plants was by treatment with water containing an osmolyte such as polyethylene glycol (PEG) at specific water potential. Since PEG may be toxic, the plants were given only a short term exposure and then normal watering was resumed. As above, seed yields were measured from the mature plants. The response was measured during the stress period by physical measurements, such as stomatal aperture or osmotic potential, or biochemical measurements, such as accumulation of proline. Tolerant plants had higher seed yields, maintained their stomatal aperture and showed only slight changes in osmotic potential and proline levels, whereas the susceptible non-transgenic control plants closed their stomata and exhibited increased osmotic potential and proline levels.

The transgenic plants with a constitutive promoter controlling transcription of the transgene were compared to those plants with a drought-inducible promoter in the absence of stress. The results indicated that the metabolite and gene expression changes noted in examples 2 and 3 did not occur when plants with the stress-inducible promoter were grown in the absence of stress. These plants also had higher seed yields than those with the constitutive promoter.

EXAMPLE 4

Inheritance and Segregation of Drought Tolerance with the Glutaredoxin and Thioredoxin Transgenes Transgenic *Arabidopsis* plants in the T2 generation were analyzed by PCR to confirm the presence of T-DNA. These results were confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer. Homozygous lines with single insertions of T-DNA were selected for cross-pollination experiments.

A homozygous line with the glutaredoxin transgene (GG) was cross-pollinated with a homozygous line with the thioredoxin transgene (TT). Since the transgenes are not at the same locus, the F1 progeny were heterozygous (G-T-). The F2 progeny segregated in a 9:3:3:1 ratio of double transformants containing both transgenes, to single transformants containing either G or T, and nulls containing neither transgene. The genotype of the progeny was determined by PCR analysis for each of the transgenes. Homozygous lines of each genotype GGTT, GG--, --TT, and ---- were identified by quantitative PCR and confirmed by inheritance patterns of the transgenes.

Homozygous lines were subjected to drought stress, metabolite analysis and expression profiling as described in examples 1, 2, 3 and 4. The transgenic lines were more drought tolerant than the null line, had altered metabolite levels consistent with the observations in example 2 and altered gene expression patterns consistent with the observations in example 3.

EXAMPLE 5

Over-Expression of Glutaredoxin or Thioredoxin Genes Provides Tolerance of Multiple Abiotic Stresses Plants that exhibit tolerance of one abiotic stress often exhibit tolerance of another environmental stress or an oxygen free radical generating herbicide. This phenomenon of cross-tolerance is not understood at a mechanistic level (McKersie and Leshem, 1994, Stress and Stress Coping in Cultivated Plants, Kluwer Academic Publishers). Nonetheless, it is reasonable to expect that plants exhibiting enhanced drought tolerance due to the expression of a transgene might also exhibit tolerance of low temperatures, freezing, salt, air pollutants such as ozone, and other abiotic stresses. In support of this hypothesis, the expression of several genes are up or down-regulated by mulitple abiotic stress factors including cold, salt, osmoticum, ABA, etc (e.g. Hong et al. (1992) Developmental and organ-specific expression of an ABA- and stress-induced protein in barley. Plant Mol Biol 18: 663-674; Jagendorf and Takabe (2001) Inducers of glycinebetaine synthesis in barley. Plant Physiol 127: 1827-1835); Mizoguchi et al. (1996) A gene encoding a mitogen-activated protein kinase kinase is induced simultaneously with genes for a mitogen-activated protein kinase and an S6 ribosomal protein kinase by touch, cold, and water stress in *Arabidopsis thaliana*. Proc Natl Acad Sci USA 93: 765-769; Zhu (2001) Cell signaling under salt, water and cold stresses. Curr Opin Plant Biol 4: 401-406).

To determine salt tolerance, seeds of *Arabidopsis thaliana* were sterilized (100% bleach, 0.1% TritonX for five minutes two times and rinsed five times with ddH2O). Seeds were plated on non-selection media (½ MS, 0.6% phytagar, 0.5 g/L MES, 1% sucrose, 2 µg/ml benamyl). Seeds are allowed to germinate for approximately ten days. At the 4-5 leaf stage, transgenic plants were potted into 5.5 cm diameter pots and allowed to grow (22° C., continuous light) for approximately seven days, watering as needed. To begin the assay, two liters of 100 mM NaCl and ⅛ MS was added to the tray under the pots. To the tray containing the control plants, three liters of ⅛ MS was added. The concentrations of NaCl supplementation were increased stepwise by 50 mM every 4 days up to 200 mM. After the salt treatment with 200 mM, fresh and dry weights of the plants as well as seed yields were determined.

To determine cold tolerance, seeds of the transgenic and cold lines were germinated and grown for approximately 10 days to the 4-5 leaf stage as above. The plants were then transferred to cold temperatures (5° C.) and grown through the flowering and seed set stages of development. Photosynthesis was measured using chlorophyll fluorescence as an indicator of photosynthetic fitness and integrity of the photosystems. Seed yield and plant dry weight were measured as an indictor of plant biomass production.

Plants that had tolerance to salinity or cold had higher seed yields, photosynthesis and dry matter production than susceptible plants.

EXAMPLE 6

Engineering Stress-Tolerant Alfalfa Plants by Over-Expressing Glutaredoxin or Thioredoxin Genes A regenerating clone of alfalfa (*Medicago sativa*) was transformed using the method of (McKersie et al., 1999 Plant Physiol 119: 839-847). Regeneration and transformation of alfalfa is genotype dependent and therefore a regenerating plant is required. Methods to obtain regenerating plants have been described. For example, these can be selected from the cultivar Rangelander (Agriculture Canada) or any other commercial alfalfa variety as described by Brown DCW and A Atanassov (1985. Plant Cell Tissue Organ Culture 4: 111-112). Alternatively, the RA3 variety (University of Wisconsin) has been selected for use in tissue culture (Walker et al., 1978 Am J Bot 65:654-659).

Petiole explants were cocultivated with an overnight culture of *Agrobacterium tumefaciens* C58C1 pMP90 (McKersie et al., 1999 Plant Physiol 119: 839-847) or LBA4404 containing a binary vector. Many different binary vector systems have been described for plant transformation (e.g. An, G. in *Agrobacterium* Protocols. Methods in Molecular Biology vol 44, pp 47-62, Gartland K M A and M R Davey eds. Humana Press, Totowa, N.J.). Many are based on the vector pBIN19 described by Bevan (Nucleic Acid Research. 1984. 12:8711-8721) that includes a plant gene expression cassette flanked by the left and right border sequences from the Ti plasmid of *Agrobacterium tumefaciens*. A plant gene expression cassette consists of at least two genes—a selection marker gene and a plant promoter regulating the transcription of the cDNA or genomic DNA of the trait gene. Various selection marker genes can be used including the *Arabidopsis* gene encoding a mutated acetohydroxy acid synthase (AHAS) enzyme (U.S. Pat. Nos. 57,673,666 and 6,225,105). Similarly, various promoters can be used to regulate the trait gene that provides constitutive, developmental, tissue or environmental regulation of gene transcription. In this example, the 34S promoter (GenBank Accession numbers M59930 and X16673) was used to provide constitutive expression of the trait gene.

The explants were cocultivated for 3 d in the dark on SH induction medium containing 288 mg/L Pro, 53 mg/L thioproline, 4.35 g/L $K_2SO_4$, and 100 µm acetosyringinone. The explants were washed in half-strength Murashige-Skoog medium (Murashige and Skoog, 1962) and plated on the same SH induction medium without acetosyringinone but with a suitable selection agent and suitable antibiotic to inhibit *Agrobacterium* growth. After several weeks, somatic embryos were transferred to BOi2Y development medium containing no growth regulators, no antibiotics, and 50 g/L sucrose. Somatic embryos were subsequently germinated on half-strength Murashige-Skoog medium. Rooted seedlings were transplanted into pots and grown in a greenhouse.

The T0 transgenic plants were propagated by node cuttings and rooted in Turface growth medium. The plants were defoliated and grown to a height of about 10 cm (approximately 2 weeks after defoliation). The plants were then subjected to drought stress in two experiments.

For the first drought experiment, the seedlings received no water for a period up to 3 weeks at which time the plant and soil were desiccated. At various times after withholding water, a normal watering schedule was resumed. At one week after resuming watering, the fresh and dry weights of the shoots was determined. At an equivalent degree of drought stress, tolerant plants were able to resume normal growth whereas susceptible plants had died or suffered significant injury resulting in less dry matter. Proline content of the leaves and stomatal aperture were also measured at various times during the drought stress. Tolerant plants maintained a lower proline content and a greater stomatal aperture than the non-transgenic control plants.

An alternative method to impose water stress on the transgenic plants was by treatment with a solution at specific water potential, containing an osmolyte such as polyethylene glycol (PEG). The PEG treatment was given to either detached leaves (e.g. Djilianov et al., 1997 Plant Science 129: 147-156) or to the roots (Wakabayashi et al., 1997 Plant Physiol 113: 967-973). Since PEG may be toxic, the plants were given only a short term exposure. The response was measured as physical measurements such as stomatal aperture or osmotic potential, or biochemical measurements such as accumulation of proline. Tolerant plants maintained their stomatal aperture and showed only slight changes in osmotic potential, whereas the susceptible non-transgenic control plants closed their stomata and exhibited increased osmotic potential. In addition the changes in proline and other metabolites were less in the tolerant transgenic plants than in the non-transgenic control plants.

Tolerance of salinity and cold were measured using methods as described in example 5. Plants that had tolerance to salinity or cold had higher seed yields, photosynthesis and dry matter production than susceptible plants.

EXAMPLE 7

Engineering Stress-Tolerant Ryegrass Plants by Over-Expressing Glutaredoxin or Thioredoxin Genes Seeds of several different ryegrass varieties may be used as explant sources for transformation, including the commercial variety Gunne available from Svalof Weibull seed company or the variety Affinity. Seeds were surface-sterilized sequentially with 1% Tween-20 for 1 minute, 100% bleach for 60 minutes, 3 rinses with 5 minutes each with de-ionized and distilled $H_2O$, and then germinated for 3-4 days on moist, sterile filter paper in the dark. Seedlings were further sterilized for 1 minute with 1% Tween-20, 5 minutes with 75% bleach, and rinsed 3 times with $ddH_2O$, 5 min each.

Surface-sterilized seeds were placed on the callus induction medium containing Murashige and Skoog basal salts and vitamins, 20 g/l sucrose, 150 mg/l asparagine, 500 mg/l casein hydrolysate, 3 g/l Phytagel, 10 mg/l BAP, and 5 mg/l dicamba. Plates were incubated in the dark at 25 C for 4 weeks for seed germination and embryogenic callus induction After 4 weeks on the callus induction medium, the shoots and roots of the seedlings were trimmed away, the callus was transferred to fresh media, maintained in culture for another 4 weeks, and then transferred to MSO medium in light for 2 weeks. Several pieces of callus (11-17 weeks old) were either strained through a 10 mesh sieve and put onto callus induction medium, or cultured in 100 ml of liquid ryegrass callus induction media (same medium as for callus induction with agar) in a 250 ml flask. The flask was wrapped in foil and shaken at 175 rpm in the dark at 23 C for 1 week. Sieving the liquid culture with a 40-mesh sieve collected the cells. The fraction collected on the sieve was plated and cultured on solid ryegrass callus induction medium for 1 week in the dark at 25 C. The callus was then transferred to and cultured on MS medium containing 1% sucrose for 2 weeks.

Transformation can be accomplished with either *Agrobacterium* of with particle bombardment methods. An expression vector is created containing a constitutive plant promoter and the cDNA of the gene in a pUC vector. The plasmid DNA was prepared from *E. coli* cells using with Qiagen kit according to manufacturer's instruction. Approximately 2 g of embryogenic callus was spread in the center of a sterile filter paper in a Petri dish. An aliquot of liquid MSO with 10 g/l sucrose was added to the filter paper. Gold particles (1.0 µm in size) were coated with plasmid DNA according to method of Sanford et al., 1993 and delivered to the embryogenic callus with the following parameters: 500 µg particles and 2 µg DNA per shot, 1300 psi and a target distance of 8.5 cm from stopping plate to plate of callus and 1 shot per plate of callus.

After the bombardment, calli were transferred back to the fresh callus development medium and maintained in the dark at room temperature for a 1-week period. The callus was then transferred to growth conditions in the light at 25 C to initiate embryo differentiation with the appropriate selection agent, e.g. 250 nM Arsenal, 5 mg/l PPT or 50 mg/L kanamycin. Shoots resistant to the selection agent appeared and once rotted were transferred to soil. Samples of the primary transgenic plants (T0) are analyzed by PCR to confirm the presence of T-DNA. These results are confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

Transgenic T0 ryegrass plants were propagated vegetatively by excising tillers. The transplanted tillers were maintained in the greenhouse for 2 months until well established. The shoots were defoliated and allowed to grow for 2 weeks.

The first drought experiment was conducted in a manner similar to that described in example 5. The seedlings received no water for a period up to 3 weeks at which time the plant and soil were desiccated. At various times after withholding water, a normal watering schedule was resumed. At one week after resuming watering, the lengths of leaf blades, and the fresh and dry weights of the shoots was determined. At an equivalent degree of drought stress, tolerant plants were able to resume normal growth whereas susceptible plants had died or suffered significant injury resulting in shorter leaves and less dry matter. Proline content of the leaves and stomatal aperture were also measured at various times during the drought stress. Tolerant plants maintained a lower proline content and a greater stomatal aperture than the non-transgenic control plants.

A second experiment imposing drought stress on the transgenic plants was by treatment with a solution of PEG as described in the previous examples. Tolerance of salinity and cold were measured using methods as described in example 5. Plants that had tolerance to salinity or cold had higher seed yields, photosynthesis and dry matter production than susceptible plants.

EXAMPLE 8

Engineering Stress-Tolerant Soybean Plants by Over-Expressing Glutaredoxin or Thioredoxin Genes Soybean was transformed according to the following modification of the method described in the Texas A&M patent U.S. Pat. No. 5,164,310. Several commercial soybean varieties are amenable to transformation by this method. The cultivar Jack (available from the Illinois Seed Foundation) is a commonly used for transformation. Seeds were sterilized by immersion in 70% (v/v) ethanol for 6 min and in 25% commercial bleach (NaOCl) supplemented with 0.1% (v/v) Tween for 20 min, followed by rinsing 4 times with sterile double distilled water. Seven-day seedlings were propagated by removing the radicle, hypocotyl and one cotyledon from each seedling. Then, the epicotyl with one cotyledon was transferred to fresh germination media in petri dishes and incubated at 25° C. under a 16-hr photoperiod (approx. 100 $\mu E\text{-}m^{-2}s^{-1}$) for three weeks. Axillary nodes (approx. 4 mm in length) were cut from 3-4 week-old plants. Axillary nodes were excised and incubated in *Agrobacterium* LBA4404 culture.

Many different binary vector systems have been described for plant transformation (e.g. An, G. in *Agrobacterium* Protocols. Methods in Molecular Biology vol 44, pp 47-62, Gartland K M A and M R Davey eds. Humana Press, Totowa, N.J.). Many are based on the vector pBIN19 described by Bevan (Nucleic Acid Research. 1984. 12:8711-8721) that includes a plant gene expression cassette flanked by the left and right border sequences from the Ti plasmid of *Agrobacterium tumefaciens*. A plant gene expression cassette consists of at least two genes—a selection marker gene and a plant promoter regulating the transcription of the cDNA or genomic DNA of the trait gene. Various selection marker genes can be used including the *Arabidopsis* gene encoding a mutated acetohydroxy acid synthase (AHAS) enzyme (U.S.

Pat. Nos. 57,673,666 and 6,225,105). Similarly, various promoters can be used to regulate the trait gene to provide constitutive, developmental, tissue or environmental regulation of gene transcription. In this example, the 34S promoter (GenBank Accession numbers M59930 and X16673) was used to provide constitutive expression of the trait gene.

After the co-cultivation treatment, the explants were washed and transferred to selection media supplemented with 500 mg/L timentin. Shoots were excised and placed on a shoot elongation medium. Shoots longer than 1 cm were placed on rooting medium for two to four weeks prior to transplanting to soil.

The primary transgenic plants (T0) were analyzed by PCR to confirm the presence of T-DNA. These results were confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

Tolerant plants had higher seed yields, maintained their stomatal aperture and showed only slight changes in osmotic potential and proline levels, whereas the susceptible non-transgenic control plants closed their stomata and exhibited increased osmotic potential and proline levels.

Tolerance of salinity and cold were measured using methods as described in example 5. Plants that had tolerance to salinity or cold had higher seed yields, photosynthesis and dry matter production than susceptible plants.

EXAMPLE 9

Engineering Stress-Tolerant Rapeseed/Canola Plants by Over-Expressing Glutaredoxin or Thioredoxin Genes Cotyledonary petioles and hypocotyls of 5-6 day-old young seedlings were used as explants for tissue culture and transformed according to Babic et al. (1998, Plant Cell Rep 17: 183-188). The commercial cultivar Westar (Agriculture Canada) is the standard variety used for transformation, but other varieties can be used.

*Agrobacterium tumefaciens* LBA4404 containing a binary vector was used for canola transformation. Many different binary vector systems have been described for plant transformation (e.g. An, G. in *Agrobacterium* Protocols. Methods in Molecular Biology vol 44, pp 47-62, Gartland K M A and M R Davey eds. Humana Press, Totowa, N.J.). Many are based on the vector pBIN19 described by Bevan (Nucleic Acid Research. 1984. 12:8711-8721) that includes a plant gene expression cassette flanked by the left and right border sequences from the Ti plasmid of *Agrobacterium tumefaciens*. A plant gene expression cassette consists of at least two genes—a selection marker gene and a plant promoter regulating the transcription of the cDNA or genomic DNA of the trait gene. Various selection marker genes can be used including the *Arabidopsis* gene encoding a mutated acetohydroxy acid synthase (AHAS) enzyme (U.S. Pat. Nos. 57,673,666 and 6,225,105). Similarly, various promoters can be used to regulate the trait gene to provide constitutive, developmental, tissue or environmental regulation of gene transcription. In this example, the 34S promoter (GenBank Accession numbers M59930 and X16673) was used to provide constitutive expression of the trait gene.

Canola seeds were surface-sterilized in 70% ethanol for 2 min., and then in 30% Clorox with a drop of Tween-20 for 10 min, followed by three rinses with sterilized distilled water. Seeds were then germinated in vitro 5 days on half strength MS medium without hormones, 1% sucrose, 0.7% Phytagar at 23° C., 16 hr. light. The cotyledon petiole explants with the cotyledon attached were excised from the in vitro seedlings, and inoculated with *Agrobacterium* by dipping the cut end of the petiole explant into the bacterial suspension. The explants were then cultured for 2 days on MSBAP-3 medium containing 3 mg/l BAP, 3% sucrose, 0.7% Phytagar at 23 C, 16 hr light. After two days of co-cultivation with *Agrobacterium*, the petiole explants were transferred to MSBAP-3 medium containing 3 mg/l BAP, cefotaxime, carbenicillin, or timentin (300 mg/l) for 7 days, and then cultured on MSBAP-3 medium with cefotaxime, carbenicillin, or timentin and selection agent until shoot regeneration. When the shoots were 5-10 mm in length, they were cut and transferred to shoot elongation medium (MSBAP-0.5, containing 0.5 mg/l BAP). Shoots of about 2 cm in length were transferred to the rooting medium (MS0) for root induction.

Samples of the primary transgenic plants (T0) were analyzed by PCR to confirm the presence of T-DNA. These results were confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

The transgenic plants were then evaluated for their improved stress tolerance according to the method described in Example 5. Tolerant plants had higher seed yields, maintained their stomatal aperture and showed only slight changes in osmotic potential and proline levels, whereas the susceptible non-transgenic control plants closed their stomata and exhibited increased osmotic potential and proline levels.

Tolerance of salinity and cold were measured using methods as described in the previous example 5. Plants that had tolerance to salinity or cold had higher seed yields, photosynthesis and dry matter production than susceptible plants.

EXAMPLE 10

Engineering Stress-Tolerant Corn Plants by Over-Expressing Glutaredoxin or Thioredoxin Genes Transformation of maize (*Zea Mays* L.) is performed with a modification of the method described by Ishida et al. (1996. Nature Biotech 14745-50). Transfromation is genotype-dependent in corn and only specific genotypes are amenable to transformation and regeneration. The inbred line A188 (University of Minnesota) or hybrids with A188 as a parent are good sources of donor material for transformation (Fromm et al. 1990 Biotech 8:833-839), but other genotypes can be used successfully as well. Ears are harvested from corn plants at approximately 11 days after pollination (DAP) when the length of immature embryos is about 1 to 1.2 mm. Immature embryos are co-cultivated with *Agrobacterium tumefaciens* that carry "super binary" vectors and transgenic plants are recovered through organogenesis. The super binary vector system of Japan Tobacco is described in WO patents WO94/00977 and WO95/06722. Vectors were constructed as described. Various selection marker genes can be used including the maize gene encoding a mutated acetohydroxy acid synthase (AHAS) enzyme (U.S. Pat. No. 6,025,541). Similarly, various promoters can be used to regulate the trait gene to provide constitutive, developmental, tissue or environmental regulation of gene transcription. In this example, the 34S promoter (GenBank Accession numbers M59930 and X16673) was used to provide constitutive expression of the trait gene.

Excised embryos are grown on callus induction medium, then maize regeneration medium, containing imidazolinone as a selection agent. The Petri plates are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the imidazolinone herbicides and which are PCR positive for the transgenes.

The T1 transgenic plants were then evaluated for their improved stress tolerance according to the method described in Example 5. The T1 generation of sincle locus insertions of the the T-DNA will segregate for the transgene in a 3:1 ratio. Those progeny containing one or two copies of the transgene are tolerant of the imidazolinone herbicide, and exhibit greater tolerance of drought stress than those progeny lacking the transgenes. Tolerant plants had higher seed yields, maintained their stomatal aperture and showed only slight changes in osmotic potential and proline levels, whereas the susceptible non-transgenic control plants closed their stomata and exhibited increased osmotic potential and proline levels. Homozygous T2 plants exhibited similar phenotypes.

Tolerance of salinity and cold were measured using methods as described in the previous example 5. Plants that had tolerance to salinity or cold had higher seed yields, photosynthesis and dry matter production than susceptible plants.

EXAMPLE 11

Engineering Stress-Tolerant Wheat Plants by Over-Expressing Glutaredoxin or Thioredoxin Genes Transformation of wheat is performed with the method described by Ishida et al. (1996 Nature Biotech. 14745-50).

The cultivar Bobwhite (available from CYMMIT, Mexico) is commonly used in transformation. Immature embryos are co-cultivated with *Agrobacterium fumefaciens* that carry "super binary" vectors, and transgenic plants are recovered through organogenesis. The super binary vector system of Japan Tobacco is described in WO patents WO94/00977 and WO95/06722. Vectors were constructed as described. Various selection marker genes can be used including the maize gene encoding a mutated acetohydroxy acid synthase (AHAS) enzyme (U.S. Pat. No. 6,025,541). Similarly, various promoters can be used to regulate the trait gene to provide constitutive, developmental, tissue or environmental regulation of gene transcription. In this example, the 34S promoter (GenBank Accession numbers M59930 and X16673) was used to provide constitutive expression of the trait gene.

After incubation with *Agrobacterium*, the embryos are grown on callus induction medium, then regeneration medium, containing imidazolinone as a selection agent. The Petri plates are incubated in the light at 25° C. for 2-3 weeks, or until shoots develop. The green shoots are transferred from each embryo to rooting medium and incubated at 25° C. for 2-3 weeks, until roots develop. The rooted shoots are transplanted to soil in the greenhouse. T1 seeds are produced from plants that exhibit tolerance to the imidazolinone herbicides and which are PCR positive for the transgenes.

The T1 transgenic plants were then evaluated for their improved stress tolerance according to the method described in the previous example 5. The T1 generation of single locus insertions of the the T-DNA will segregate for the transgene in a 3:1 ratio. Those progeny containing one or two copies of the transgene are tolerant of the imidazolinone herbicide, and exhibit greater tolerance of drought stress than those progeny lacking the transgenes. Tolerant plants had higher seed yields, maintained their stomatal aperture and showed only slight changes in osmotic potential and proline levels, whereas the susceptible non-transgenic control plants closed their stomata and exhibited increased osmotic potential and proline levels. Homozygous T2 plants exhibited similar phenotypes.

The invention claimed is:

1. A method of producing a transgenic plant having an increased tolerance to an environmental stress, said method comprising the steps of:

(a) transforming plant cells with an expression cassette comprising a polynucleotide sequence which comprises a nucleotide sequence encoding an Oxidoreductase Stress-Related Protein (ORSRP) having an amino acid sequence that is at least 95% identical to the amino acid sequence set forth in SEQ ID NO: 8, and wherein the nucleotide sequence is operably linked to a promoter;

(b) regenerating transgenic plants from said transformed plant cells; and (c) selecting a transformed plant from said transgenic plants which exhibits increase in tolerance to an environmental stress as compared to an untransformed plant of the same species, and wherein said increase in environmental stress tolerance is due to the expression of said Oxidoreductase Stress-Related Protein in said selected transformed plant.

2. The method of claim 1 further comprises obtaining a transformed seed from the selected transformed plant of step (c), and wherein the transformed seed comprises said expression cassette and exhibits increase in tolerance to said environmental stress as compared to an untransformed seed of the same species.

3. The method of claim 1, wherein said polynucleotide sequence comprises the nucleotide sequence of SEQ ID NO: 7.

4. The method of claim 1, wherein said nucleotide sequence encodes the Oxidoreductase Stress-Related Protein as set forth in SEQ ID NO: 8.

5. The method of claim 1, wherein said promoter is an inducible promoter, a tissue-specific promoter, or a developmentally regulated promoter.

6. The method of claim 1, wherein the environmental stress is salinity, drought, temperature, metal, chemical, pathogenic or oxidative stresses, or any combination thereof.

7. The method of claim 1, wherein the plant cell is obtained from a monocotyledonous plant, a dicotyledonous plant, or a gymnosperm plant.

8. The method of claim 1, wherein the plant is a monocotyledonous plant, a dicotyledonous plant, or a gymnosperm plant.

* * * * *

UNITED STATES PATENT AND TRADEMARK OFFICE
CERTIFICATE OF CORRECTION

PATENT NO. : 8,552,255 B2  Page 1 of 1
APPLICATION NO. : 13/097265
DATED : October 8, 2013
INVENTOR(S) : Agnes Chardonnens et al.

It is certified that error appears in the above-identified patent and that said Letters Patent is hereby corrected as shown below:

On the Title Page of the patent:

"(75) Inventors" should read as follows:

"Agnes Chardonnens, Nn Enkhuizen (NL); Piotr Puzio, Mariakerke (Gent) (BE)"

Signed and Sealed this
Twenty-eighth Day of January, 2014

Michelle K. Lee
*Deputy Director of the United States Patent and Trademark Office*